(12) United States Patent
Ackermann et al.

(10) Patent No.: US 7,713,996 B2
(45) Date of Patent: May 11, 2010

(54) INDOLYL DERIVATIVES WHICH ARE L-CPT1 INHIBITORS

(75) Inventors: Jean Ackermann, Riehen (CH);
Konrad Bleicher, Freiburg (DE);
Simona M Ceccarelli Grenz, Basel (CH); Odile Chomienne, Altkirch (FR);
Patrizio Mattei, Riehen (CH); Tanja Schulz-Gasch, Liestal (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 749 days.

(21) Appl. No.: 11/519,485

(22) Filed: Sep. 12, 2006

(65) Prior Publication Data

US 2007/0060567 A1    Mar. 15, 2007

(30) Foreign Application Priority Data

Sep. 15, 2005    (EP)    .................................. 05108468

(51) Int. Cl.
*A61K 31/404* (2006.01)
*A61K 31/47* (2006.01)
*C07D 209/04* (2006.01)
*C07D 215/00* (2006.01)

(52) U.S. Cl. ........................ 514/312; 546/112; 546/152; 546/156; 548/469; 548/490; 548/491; 514/311; 514/415; 514/419

(58) Field of Classification Search ................. 548/469, 548/490, 491; 546/112, 152, 156; 514/311, 514/312, 415, 419
See application file for complete search history.

(56) References Cited

U.S. PATENT DOCUMENTS 6,800,645 B1 *  10/2004  Cox et al. ................... 514/314
7,329,675 B2 *  2/2008  Cox et al. ................. 546/272.1

OTHER PUBLICATIONS

*Bioorg. Med. Chem. Lett.*, 1999, 9, 1403-1408.
Jackson et al., 1999, *Biochem. J.* 341, 483-489.
Jackson et al., 2000, *J. Biol. Chem.* 275, 19560-19566.
*Helv. Chim. Acta* 1980, 37, 385.
*J Chem. Soc. (C)* 1969, 183.
*Bioorg. Med. Chem. Lett.* 1998, 8, 1867.

* cited by examiner

*Primary Examiner*—Golam M Shameem
(74) *Attorney, Agent, or Firm*—George W. Johnston; Dennis P. Tramaloni; Samuel H. Megerditchian

(57) ABSTRACT

The invention is concerned with novel heterobicyclic derivatives of formula (I):

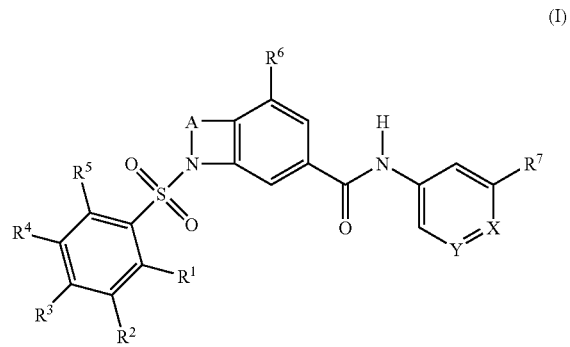

wherein $R^1$, $R^2$, $R^3$, $R^4$, $R^5$, $R^6$, $R^7$, A, X and Y are as defined in the description and in the claims, as well as physiologically acceptable salts and esters thereof. These compounds inhibit L-CPT1 and can be used as medicaments.

29 Claims, No Drawings

INDOLYL DERIVATIVES WHICH ARE L-CPT1 INHIBITORS

PRIORITY TO RELATED APPLICATIONS

This application claims the benefit of European Application No. 05108468.9, filed Sep. 15, 2005, which is hereby incorporated by reference in its entirety.

FIELD OF THE INVENTION

The invention is directed to novel heterobicyclic derivatives of the formula (I)

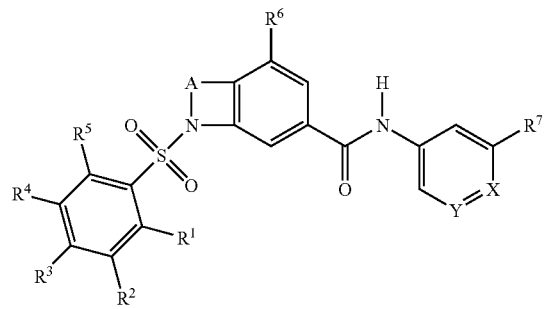

and pharmaceutically acceptable salts and esters thereof.

Further, the invention is directed to a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-ter domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit L-CPT1 reduce liver β-oxidation, consequently inhibit gluconeogenesis and therefore counteract hyperglycemia. Thus, there is a need for compounds which inhibit L-CPT1 activity.

SUMMARY OF THE INVENTION

In one embodiment of the present invention, provided is a a compound of formula (I):

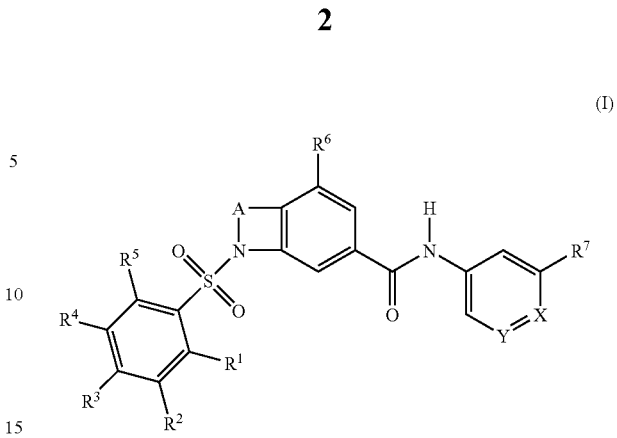

wherein

X is N or $CR^8$;

Y is N or $CR^9$;

A is —$C(R^{10}R^{11})C(R^{12}R^{13})$—, —$C(R^{10}R^{11})C(R^{12}R^{13})C(R^{14}R^{15})$—, —$C(R^{10}R^{11})C(R^{12}R^{13})C(R^{14}R^{15})C(R^{16}R^{17})$—, —$C(R^{10}R^{11})C(R^{12}R^{13})C(R^{14}R^{15})C(R^{16}R^{17})C(R^{18}R^{19})$— or —$C(R^{10})$=$C(R^{11})$—;

$R^1$, $R^2$, $R^3$, $R^4$ and $R^5$ independently from each other are hydrogen, halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$ or N(lower-alkyl)$_2$-S(O)$_2$, NH$_2$—C(O), N(H, lower-alkyl)-C(O), N(lower-alkyl)$_2$-C(O) or lower-alkoxy-C(O), wherein lower-alkyl is optionally substituted with hydroxy, lower-alkoxy, NH$_2$, N(H, lower-alkyl) or N(lower-alkyl)$_2$;

$R^6$ is hydrogen, halogen, lower-alkyl, lower-alkoxy, fluoro-lower-alkyl, fluoro-lower-alkoxy, hydroxy or hydroxy-lower-alkyl;

$R^7$ is hydrogen, halogen, hydroxy, cyano, lower-alkyl, lower-alkoxy, fluoro-lower-alkyl, fluoro-lower-alkoxy or hydroxy-lower-alkyl;

$R^8$ is hydrogen, halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$, N(lower-alkyl)$_2$-S(O)$_2$, NH$_2$—C(O), N(H, lower-alkyl)-C(O), N(lower-alkyl)$_2$-C(O), lower-alkoxy-C(O), COOH, 1H-tetrazolyl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, SO$_3$H, 3-hydroxy-isooxazolyl, 3-hydroxy-pyran-4-one-yl or P(O)(OCH$_2$CH$_3$)OH, wherein lower-alkyl is optionally substituted with hydroxy, NH$_2$, N(H, lower-alkyl) or N(lower-alkyl)$_2$, and wherein fluoro-lower-alkyl is optionally substituted with hydroxy;

$R^9$ is hydrogen, halogen, hydroxy, cyano, lower-alkyl, lower-alkoxy, fluoro-lower-alkyl, fluoro-lower-alkoxy or hydroxy-lower-alkyl;

$R^{10}$, $R^{11}$, $R^{12}$, $R^{13}$, $R^{14}$, $R^{15}$, $R^{16}$, $R^{17}$, $R^{18}$, $R^{19}$ independently from each other are hydrogen, halogen, hydroxy, lower-alkyl, lower-alkoxy, fluoro-lower-alkyl, fluoro-lower-alkoxy, hydroxy-lower-alkyl or cyano;

and pharmaceutically acceptable salts and esters thereof.

In another embodiment of the present invention, provided is a process for the manufacture of compounds of formula (I), comprising the step of:

reacting a compound of formula (IV)

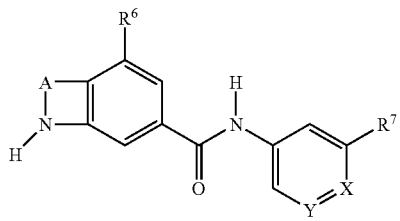

with a compound of formula (V)

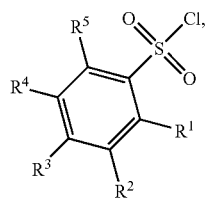

or reacting a compound of formula (VI)

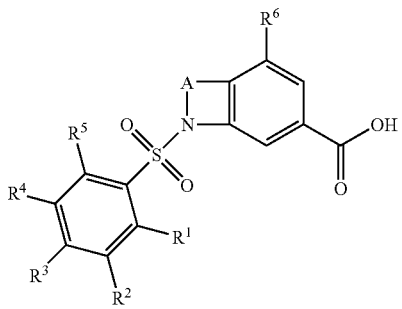

with a compound of formula (VII)

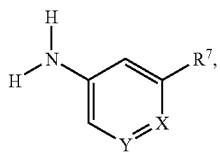

wherein $R^1$, $R^2$, $R^3$, $R^4$, $R^5$, $R^6$, $R^7$, A, X and Y are as defined above.

In a further embodiment of the present invention, provided is a pharmaceutical composition, comprising a therapeutically effective amount of a compound according to formula I and a pharmaceutically acceptable carrier and/or adjuvant.

In a yet another embodiment of the present invention, provided is a method for the therapeutic and/or prophylactic treatment of diseases which are modulated by L-CPT1 inhibitors, comprising the step of administering a therapeutically effective amount of a compound according to formula I to a human being or animal in need thereof.

DETAILED DESCRIPTION

The present invention relates to novel compounds which inhibit liver carnitine palmitoyl transferase 1 (L-CPT1) activity. The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups. Alkyl groups can optionally be substituted with hydroxy, $NH_2$, N(H, lower-alkyl) or N(lower-alkyl)$_2$ or lower-alkoxy. Unless specifically mentioned, unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted with hydroxy, $NH_2$, N(H, lower-alkyl) or N(lower-alkyl)$_2$. Unless specifically mentioned, unsubstituted lower-alkyl groups are preferred. The term "hydroxy-lower-alkyl" refers to a lower-alkyl group which is substituted with hydroxy.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "acid isostere" refers to groups which have similar steric and electronic features of a carboxylic acid, or that are known in the art to mimic the spatial arrangement and electronic properties of a carboxylic acid. Examples of acid isosteres are 1H-tetrazolyl, particularly 1H-tetrazol-5-yl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, SO$_3$H, 3-hydroxy-isooxazol, 3-hydroxy-pyran-4-one, particularly 3-hydroxy-pyran-4-one-5-yl, or P(O)(OCH$_2$CH$_3$)OH.

Compounds of formula (I) can form pharmaceutically acceptable salts with bases. Examples of such salts are alkaline, earth-alkaline and ammonium salts such as e.g. Na—, K—, Ca— and trimethylammoniumsalt.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

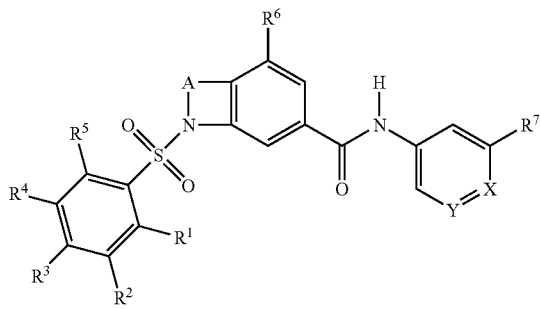

(I)

wherein

X is N or CR$^8$;

Y is N or CR$^9$;

A is —C(R$^{10}$R$^{11}$)C(R$^{12}$R$^{13}$)—, —C(R$^{10}$R$^{11}$)C(R$^{12}$R$^{13}$)C(R$^{14}$R$^{15}$)—, —C(R$^{10}$R$^{11}$)C(R$^{12}$R$^{13}$)C(R$^{14}$R$^{15}$)C(R$^{16}$R$^{17}$)—, —C(R$^{10}$R$^{11}$)C(R$^{12}$R$^{13}$)C(R$^{14}$R$^{15}$)C(R$^{16}$R$^{17}$)C(R$^{18}$R$^{19}$)— or —C(R$^{10}$)=C(R$^{11}$)—;

R$^1$, R$^2$, R$^3$, R$^4$ and R$^5$ independently from each other are hydrogen, halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$ or N(lower-alkyl)$_2$-S(O)$_2$, NH$_2$—C(O), N(H, lower-alkyl)-C(O), N(lower-alkyl)$_2$-C(O) or lower-alkoxy-C(O), wherein lower-alkyl is optionally substituted with hydroxy, lower alkoxy, NH$_2$, N(H, lower-alkyl) or N(lower-alkyl)$_2$;

R$^6$ is hydrogen, halogen, lower-alkyl, lower-alkoxy, fluoro-lower-alkyl, fluoro-lower-alkoxy, hydroxy or hydroxy-lower-alkyl;

R$^7$ is hydrogen, halogen, hydroxy, cyano, lower-alkyl, lower-alkoxy, fluoro-lower-alkyl, fluoro-lower-alkoxy or hydroxy-lower-alkyl;

R$^8$ is hydrogen, halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$, N(lower-alkyl)$_2$-S(O)$_2$, NH$_2$—C(O), N(H, lower-alkyl)-C(O), N(lower-alkyl)$_2$-C(O), lower-alkoxy-C(O), COOH, 1H-tetrazolyl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, SO$_3$H, 3-hydroxy-isooxazolyl, 3-hydroxy-pyran-4-one-yl or P(O)(OCH$_2$CH$_3$)OH, wherein lower-alkyl is optionally substituted with hydroxy, NH$_2$, N(H, lower-alkyl) or N(lower-alkyl)$_2$, and wherein fluoro-lower-alkyl is optionally substituted with hydroxy;

R$^9$ is hydrogen, halogen, hydroxy, cyano, lower-alkyl, lower-alkoxy, fluoro-lower-alkyl, fluoro-lower-alkoxy or hydroxy-lower-alkyl;

R$^{10}$, R$^{11}$, R$^{12}$, R$^{13}$, R$^{14}$, R$^{15}$, R$^{16}$, R$^{17}$, R$^{18}$, R$^{19}$ independently from each other are hydrogen, halogen, hydroxy, lower-alkyl, lower-alkoxy, fluoro-lower-alkyl, fluoro-lower-alkoxy, hydroxy-lower-alkyl or cyano;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

Preferred compounds of formula (I) as described above are those, wherein R$^8$ is hydrogen, halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$, N(lower-alkyl)$_2$-S(O)$_2$, NH$_2$—C(O), N(H, lower-alkyl)-C(O), N(lower-alkyl)$_2$-C(O), lower-alkoxy-C(O), COOH, 1H-tetrazol-2-yl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, SO$_3$H, 3-hydroxy-isooxazol, 3-hydroxy-pyran-4-one or P(O)(OCH$_2$CH$_3$)OH, wherein lower-alkyl is optionally substituted with hydroxy, NH$_2$, N(H, lower-alkyl) or N(lower-alkyl)$_2$, and wherein fluoro-lower-alkyl is optionally substituted with hydroxy;

Preferred compounds of compounds of formula (I) as described above are those, wherein R$^1$, R$^2$, R$^3$, R$^4$ and R$^5$ independently from each other are hydrogen, halogen, lower-alkyl, fluoro-lower-alkyl, lower-alkoxy or fluoro-lower-alkoxy. More preferably, R$^1$, R$^2$, R$^3$, R$^4$ and R$^5$ independently from each other are hydrogen, halogen, lower-alkyl, fluoro-lower-alkyl or lower-alkoxy.

In a preferred embodiment, R$^1$ is hydrogen or lower-alkoxy, more preferably hydrogen or methoxy. Hydrogen and methoxy individually constitute separate preferred embodiments. In another preferred embodiment, R$^2$ is hydrogen, halogen, lower-alkyl or fluoro-lower-alkyl, more preferably hydrogen, Cl, CH$_3$ or CF$_3$. Hydrogen, Cl, CH$_3$ and CF$_3$ individually constitute separate preferred embodiments. In a further preferred embodiment, R$^3$ is hydrogen or halogen, more preferably hydrogen or Cl. Hydrogen and Cl individually constitute separate preferred embodiments. In another preferred embodiment, $R^4$ is hydrogen, halogen, lower-alkyl or fluoro-lower-alkyl, more preferably hydrogen, Cl, $CH_3$ or $CF_3$. Hydrogen, Cl, $CH_3$ and $CF_3$ individually constitute separate preferred embodiments. In still another preferred embodiment, $R^5$ is hydrogen or lower-alkoxy, preferably hydrogen or methoxy. Hydrogen and methoxy individually constitute separate preferred embodiments.

Other preferred compounds of the present invention are those, wherein $R^6$ is hydrogen, lower-alkyl or lower-alkoxy, preferably wherein $R^6$ is hydrogen or lower-alkoxy, more preferably wherein $R^6$ is hydrogen. Another preferred embodiment of the present invention relates to compounds of formula (I) as defined above, wherein $R^7$ is hydrogen, halogen or fluoro-lower-alkyl, preferably wherein $R^7$ is hydrogen or halogen, more preferably hydrogen, F or Cl. Hydrogen, F and Cl individually constitute separate preferred embodiments.

Another preferred embodiment of the present invention is related to compounds of formula (I) as defined above, wherein X is $CR^8$ and $R^8$ is as defined above. Preferably, $R^8$ is hydrogen, halogen, COOH, 1H-tetrazolyl, 4H-[1,2,4]oxadiazol-3-yl-5-one or fluoro-lower-alkyl which is substituted with hydroxy. Preferably, $R^8$ is hydrogen, halogen, COOH, 1H-tetrazol-5-yl, 4H-[1,2,4]oxadiazol-3-yl-5-one or fluoro-lower-alkyl which is substituted with hydroxy. Preferably, $R^8$ is hydrogen, halogen, COOH, 1H-tetrazol-2-yl, 4H-[1,2,4]oxadiazol-3-yl-5-one or fluoro-lower-alkyl which is substituted with hydroxy. More preferably, $R^8$ is COOH or 4H-[1,2,4]oxadiazol-3-yl-5-one. COOH and 4H-[1,2,4]oxadiazol-3-yl-5-one individually constitute separate preferred embodiments.

Other preferred compounds of the present invention are those, wherein Y is $CR^9$ and $R^9$ is as defined above. Preferably. $R^9$ is hydrogen, halogen or fluoro-lower-alkyl. More preferably, $R^9$ is hydrogen or halogen, even more preferably hydrogen, F or Cl. Hydrogen, F and Cl individually constitute separate preferred embodiments.

Preferred compounds as described above are those, wherein A is —C($R^{10}R^{11}$)C($R^{12}R^{13}$)—, —C($R^{10}R^{11}$)C($R^{12}R^{13}$)C($R^{14}R^{15}$)—, —C($R^{10}R^{11}$)C($R^{12}R^{13}$)C($R^{14}R^{15}$)C($R^{16}R^{17}$)— or —C($R^{10}$)=C($R^{11}$)—, and $R^{10}$, $R^{11}$, $R^{12}$, $R^{13}$, $R^{14}$, $R^{15}$, $R^{16}$ and $R^{17}$ are as defined above. Preferably, $R^{10}$, $R^{11}$, $R^{12}$, $R^{13}$, $R^{14}$ $R^{15}$, $R^{16}$ and $R^{17}$ independently from each other are hydrogen or lower-alkyl. Compounds of formula (I) as defined above, wherein A is —C($R^{10}R^{11}$)C($R^{12}R^{13}$)—, —C($R^{10}R^{11}$)C($R^{12}R^{13}$)C($R^{14}R^{15}$)—or —C($R^{10}$)=C($R^{11}$)—, and $R^{10}$, $R^{11}$, $R^{12}$, $R^{13}$, $R^{14}$ and $R^{15}$ are as defined above are preferred. Preferably, $R^{10}$, $R^{11}$, $R^{12}$, $R^{13}$, $R^{14}$ and $R^{15}$ are hydrogen. —C($R^{10}R^{11}$)C($R^{12}R^{13}$)—, —C($R^{10}R^{11}$)C($R^{12}R^{13}$)C($R^{14}R^{15}$)—, —C($R^{10}R^{11}$)C($R^{12}R^{13}$)C($R^{14}R^{15}$)C($R^{16}R^{17}$)— and —C($R^{10}$)=C($R^{11}$)— individually constitute separate preferred embodiments.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:

2-Chloro-4-{[1-(3-chloro-benzenesulfonyl)-2,3-dihydro-1H-indole-6-carbonyl]-amino}-benzoic acid;
2-Chloro-4-{[1-(5-chloro-2-methoxy-benzenesulfonyl)-2,3-dihydro-1H-indole-6-carbonyl]-amino}-benzoic acid;
2-Chloro-4-{[1-(3-trifluoromethyl-benzenesulfonyl)-2,3-dihydro-1H-indole-6-carbonyl]-amino}-benzoic acid;
2-Chloro-4-{[1-(3,4-dichloro-benzenesulfonyl)-2,3-dihydro-1H-indole-6-carbonyl]-amino}-benzoic acid;
2-Chloro-4-{[1-(3,5-dichloro-benzenesulfonyl)-2,3-dihydro-1H-indole-6-carbonyl]-amino}-benzoic acid;
2-Chloro-4-{[1-(3-fluoro-benzenesulfonyl)-2,3-dihydro-1H-indole-6-carbonyl]-amino}-benzoic acid;
2-Chloro-4-{[1-(2-methoxy-5-methyl-benzenesulfonyl)-2,3-dihydro-1H-indole-6-carbonyl]-amino}-benzoic acid;
2-Chloro-4-{[1-(4-difluoromethoxy-benzenesulfonyl)-2,3-dihydro-1H-indole-6-carbonyl]-amino}-benzoic acid;
4-{[1-(3-Chloro-benzenesulfonyl)-2,3-dihydro-1H-indole-6-carbonyl]-amino}-2-fluoro-benzoic acid;
2-Fluoro-4-{[1-(3-trifluoromethyl-benzenesulfonyl)-2,3-dihydro-1H-indole-6-carbonyl]-amino}-benzoic acid;
4-{[1-(3,4-Dichloro-benzenesulfonyl)-2,3-dihydro-1H-indole-6-carbonyl]-amino}-2-fluoro-benzoic acid;
4-{[1-(5-Chloro-2-methoxy-benzenesulfonyl)-2,3-dihydro-1H-indole-6-carbonyl]-amino}-2-fluoro-benzoic acid;
1-(3-Chloro-benzenesulfonyl)-2,3-dihydro-1H-indole-6-carboxylic acid [4-(1H-tetrazol-5-yl)-3-trifluoromethyl-phenyl]-amide;
2-Fluoro-4-{[4-methoxy-1-(3-trifluoromethyl-benzenesulfonyl)-2,3-dihydro-1H-indole-6-carbonyl]-amino}-benzoic acid;
4-{[1-(3-Chloro-benzenesulfonyl)-4-methoxy-2,3-dihydro-1H-indole-6-carbonyl]-amino}-2-fluoro-benzoic acid;
4-{[1-(3,4-Dichloro-benzenesulfonyl)-4-methoxy-2,3-dihydro-1H-indole-6-carbonyl]-amino}-2-fluoro-benzoic acid;
4-{[1-(5-Chloro-2-methoxy-benzenesulfonyl)-4-methoxy-2,3-dihydro-1H-indole-6-carbonyl]-amino}-2-fluoro-benzoic acid;
4-{[1-(3,5-Dichloro-benzenesulfonyl)-4-methoxy-2,3-dihydro-1H-indole-6-carbonyl]-amino}-2-fluoro-benzoic acid;
2-Fluoro-4-{[1-(3-fluoro-benzenesulfonyl)-4-methoxy-2,3-dihydro-1H-indole-6-carbonyl]-amino}-benzoic acid;
2-Fluoro-4-{[4-methoxy-1-(2-methoxy-5-methyl-benzenesulfonyl)-2,3-dihydro-1H-indole-6-carbonyl]-amino}-benzoic acid;
2-Chloro-4-{[4-methoxy-1-(3-trifluoromethyl-benzenesulfonyl)-2,3-dihydro-1H-indole-6-carbonyl]-amino}-benzoic acid;
2-Chloro-4-{[1-(5-chloro-2-methoxy-benzenesulfonyl)-4-methoxy-2,3-dihydro-1H-indole-6-carbonyl]-amino}-benzoic acid;
2-Chloro-4-{[1-(3,5-dichloro-benzenesulfonyl)-4-methoxy-2,3-dihydro-1H-indole-6-carbonyl]-amino}-benzoic acid;
2-Chloro-4-{[1-(3-fluoro-benzenesulfonyl)-4-methoxy-2,3-dihydro-1H-indole-6-carbonyl]-amino}-benzoic acid;
2-Chloro-4-{[1-(3-chloro-benzenesulfonyl)-4-methoxy-2,3-dihydro-1H-indole-6-carbonyl]-amino}-benzoic acid;
4-{[1-(3-Chloro-benzenesulfonyl)-4-methoxy-2,3-dihydro-1H-indole-6-carbonyl]-amino}-benzoic acid;
4-{[1-(5-Chloro-2-methoxy-benzenesulfonyl)-4-methoxy-2,3-dihydro-1H-indole-6-carbonyl]-amino}-benzoic acid;
4-{[4-Methoxy-1-(2-methoxy-5-methyl-benzenesulfonyl)-2,3-dihydro-1H-indole-6-carbonyl]-amino}-benzoic acid;
4-{[1-(3-Fluoro-benzenesulfonyl)-4-methoxy-2,3-dihydro-1H-indole-6-carbonyl]-amino}-benzoic acid;
4-{[1-(3,5-Dichloro-benzenesulfonyl)-2,3-dihydro-1H-indole-6-carbonyl]-amino}-benzoic acid;
4-{[1-(5-Chloro-2-methoxy-benzenesulfonyl)-2,3-dihydro-1H-indole-6-carbonyl]-amino}-benzoic acid;
4-{[1-(3-Trifluoromethoxy-benzenesulfonyl)-2,3-dihydro-1H-indole-6-carbonyl]-amino}-benzoic acid;
4-{[1-(3-Fluoro-benzenesulfonyl)-2,3-dihydro-1H-indole-6-carbonyl]-amino}-benzoic acid;
1-(5-Chloro-2-methoxy-benzenesulfonyl)-2,3-dihydro-1H-indole-6-carboxylic acid (4-chloro-phenyl)-amide;

1-(5-Chloro-2-methoxy-benzenesulfonyl)-2,3-dihydro-1H-indole-6-carboxylic acid phenylamide;
4-[(1-Benzenesulfonyl-2,3-dihydro-1H-indole-6-carbonyl)-amino]-benzoic acid;
1-(5-Chloro-2-methoxy-benzenesulfonyl)-2,3-dihydro-1H-indole-6-carboxylic acid [4-(1H-tetrazol-5-yl)-phenyl]-amide;
1-(5-Chloro-2-methoxy-benzenesulfonyl)-2,3-dihydro-1H-indole-6-carboxylic acid [4-(5-oxo-4,5-dihydro-[1,2,4]oxadiazol-3-yl)-phenyl]-amide;
1-(5-Chloro-2-methoxy-benzenesulfonyl)-2,3-dihydro-1H-indole-6-carboxylic acid [4-(2,2,2-trifluoro-1-hydroxy-ethyl)-phenyl]-amide;
2-Chloro-4-{[1-(3-fluoro-benzenesulfonyl)-1,2,3,4-tetrahydro-quinoline-7-carbonyl]-amino}-benzoic acid;
2-Chloro-4-{[1-(3,4-dichloro-benzenesulfonyl)-1,2,3,4-tetrahydro-quinoline-7-carbonyl]-amino}-benzoic acid;
2-Chloro-4-{[1-(3,5-dichloro-benzenesulfonyl)-1,2,3,4-tetrahydro-quinoline-7-carbonyl]-amino}-benzoic acid;
2-Chloro-4-{[1-(3-trifluoromethyl-benzenesulfonyl)-1,2,3,4-tetrahydro-quinoline-7-carbonyl]-amino}-benzoic acid;
2-Chloro-4-{[1-(4-difluoromethoxy-benzenesulfonyl)-1,2,3,4-tetrahydro-quinoline-7-carbonyl]-amino}-benzoic acid;
2-Chloro-4-{[1-(5-chloro-2-methoxy-benzenesulfonyl)-1,2,3,4-tetrahydro-quinoline-7-carbonyl]-amino}-benzoic acid;
2-Chloro-4-{[1-(2-methoxy-5-methyl-benzenesulfonyl)-1,2,3,4-tetrahydro-quinoline-7-carbonyl]-amino}-benzoic acid;
2-Chloro-4-{[1-(3-chloro-benzenesulfonyl)-1,2,3,4-tetrahydro-quinoline-7-carbonyl]-amino}-benzoic acid;
2-Fluoro-4-{[1-(3-fluoro-benzenesulfonyl)-1,2,3,4-tetrahydro-quinoline-7-carbonyl]-amino}-benzoic acid;
4-{[1-(3-Chloro-benzenesulfonyl)-1,2,3,4-tetrahydro-quinoline-7-carbonyl]-amino}-2-fluoro-benzoic acid;
2-Fluoro-4-{[1-(2-methoxy-5-methyl-benzenesulfonyl)-1,2,3,4-tetrahydro-quinoline-7-carbonyl]-amino}-benzoic acid;
4-{[1-(5-Chloro-2-methoxy-benzenesulfonyl)-1,2,3,4-tetrahydro-quinoline-7-carbonyl]-amino}-2-fluoro-benzoic acid;
4-{[1-(4-Difluoromethoxy-benzenesulfonyl)-1,2,3,4-tetrahydro-quinoline-7-carbonyl]-amino}-2-fluoro-benzoic acid;
4-{[1-(3,5-Dichloro-benzenesulfonyl)-1,2,3,4-tetrahydro-quinoline-7-carbonyl]-amino}-2-fluoro-benzoic acid;
2-Fluoro-4-{[1-(3-trifluoromethyl-benzenesulfonyl)-1,2,3,4-tetrahydro-quinoline-7-carbonyl]-amino}-benzoic acid;
4-{[1-(3,4-Dichloro-benzenesulfonyl)-1,2,3,4-tetrahydro-quinoline-7-carbonyl]-amino}-2-fluoro-benzoic acid;
1-(3-Chloro-benzenesulfonyl)-1,2,3,4-tetrahydro-quinoline-7-carboxylic acid [4-(1H-tetrazol-5-yl)-3-trifluoromethyl-phenyl]-amide;
4-{[1-(5-Chloro-2-methoxy-benzenesulfonyl)-1,2,3,4-tetrahydro-quinoline-7-carbonyl]-amino}-benzoic acid;
4-{[1-(3-Chloro-benzenesulfonyl)-1,2,3,4-tetrahydro-quinoline-7-carbonyl]-amino}-benzoic acid;
4-{[1-(3-Trifluoromethyl-benzenesulfonyl)-1,2,3,4-tetrahydro-quinoline-7-carbonyl]-amino}-benzoic acid;
4-{[1-(3-Fluoro-benzenesulfonyl)-1,2,3,4-tetrahydro-quinoline-7-carbonyl]-amino}-benzoic acid; and
4-{[1-(5-Chloro-2-methoxy-benzenesulfonyl)-1H-indole-6-carbonyl]-amino}-benzoic acid;

and pharmaceutically acceptable salts and esters thereof.

Particularly preferred compounds of formula (I) are those selected from the group consisting of:

2-Chloro-4-{[1-(3,4-dichloro-benzenesulfonyl)-2,3-dihydro-1H-indole-6-carbonyl]-amino}-benzoic acid;
2-Chloro-4-{[1-(3,5-dichloro-benzenesulfonyl)-2,3-dihydro-1H-indole-6-carbonyl]-amino}-benzoic acid;
2-Fluoro-4-{[1-(3-trifluoromethyl-benzenesulfonyl)-2,3-dihydro-1H-indole-6-carbonyl]-amino}-benzoic acid;
4-{[1-(5-Chloro-2-methoxy-benzenesulfonyl)-2,3-dihydro-1H-indole-6-carbonyl]-amino}-benzoic acid;
1-(5-Chloro-2-methoxy-benzenesulfonyl)-2,3-dihydro-1H-indole-6-carboxylic acid [4-(1H-tetrazol-5-yl)-phenyl]-amide;
2-Chloro-4-{[1-(5-chloro-2-methoxy-benzenesulfonyl)-1,2,3,4-tetrahydro-quinoline-7-carbonyl]-amino}-benzoic acid;
2-Fluoro-4-{[1-(2-methoxy-5-methyl-benzenesulfonyl)-1,2,3,4-tetrahydro-quinoline-7-carbonyl]-amino}-benzoic acid;
4-{[1-(5-Chloro-2-methoxy-benzenesulfonyl)-1,2,3,4-tetrahydro-quinoline-7-carbonyl]-amino}-2-fluoro-benzoic acid;
4-{[1-(3,5-Dichloro-benzenesulfonyl)-1,2,3,4-tetrahydro-quinoline-7-carbonyl]-amino}-2-fluoro-benzoic acid;
4-{[1-(5-Chloro-2-methoxy-benzenesulfonyl)-1,2,3,4-tetrahydro-quinoline-7-carbonyl]-amino}-benzoic acid; and
4-{[1-(5-Chloro-2-methoxy-benzenesulfonyl)-1H-indole-6-carbonyl]-amino}-benzoic acid;

and pharmaceutically acceptable salts and esters thereof.

Other preferred compounds of formula (I) are those selected from the group consisting of:

4-{[1-(5-Chloro-2-methoxy-benzenesulfonyl)-4-methyl-2,3-dihydro-1H-indole-6-carbonyl]-amino}-benzoic acid;
4-{[1-(5-Chloro-2-methoxy-benzenesulfonyl)-4-methyl-2,3-dihydro-1H-indole-6-carbonyl]-amino}-2-fluoro-benzoic acid;
2-Chloro-4-{[1-(5-chloro-2-methoxy-benzenesulfonyl)-4-methyl-2,3-dihydro-1H-indole-6-carbonyl]-amino}-benzoic acid;
4-{[1-(5-Chloro-2-methoxy-benzenesulfonyl)-2,3,4,5-tetrahydro-1H-benzo[b]azepine-8-carbonyl]-amino}-benzoic acid;
4-{[1-(5-Chloro-2-methoxy-benzenesulfonyl)-2,3,4,5-tetrahydro-1H-benzo[b]azepine-8-carbonyl]-amino}-2-fluoro-benzoic acid;
2-Chloro-4-{[1-(5-chloro-2-methoxy-benzenesulfonyl)-2,3,4,5-tetrahydro-1H-benzo[b]azepine-8-carbonyl]-amino}benzoic acid;
4-{[1-(5-Chloro-2-methoxy-benzenesulfonyl)-3-methyl-2,3-dihydro-1H-indole-6-carbonyl]-amino}-benzoic acid;
4-{[1-(5-Chloro-2-methoxy-benzenesulfonyl)-3-methyl-2,3-dihydro-1H-indole-6-carbonyl]-amino}-2-fluoro-benzoic acid;
2-Chloro-4-{[1-(5-chloro-2-methoxy-benzenesulfonyl)-3-methyl-2,3-dihydro-1H-indole-6-carbonyl]-amino}-benzoic acid;
4-{[1-(2-Methoxy-5-methyl-benzenesulfonyl)-1H-indole-6-carbonyl]-amino}benzoic acid;
4-{[1-(3-Chloro-benzenesulfonyl)-1H-indole-6-carbonyl]-amino}-benzoic acid; and
4-{[1-(3,5-Dimethyl-benzenesulfonyl)-1H-indole-6-carbonyl]-amino}benzoic acid;

and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (IV)

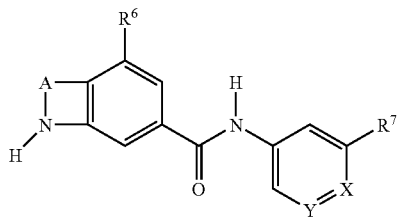

(IV)

with a compound of formula (V)

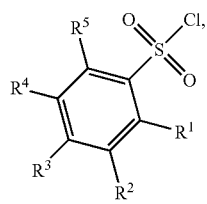

(V)

or reacting a compound of formula (VI)

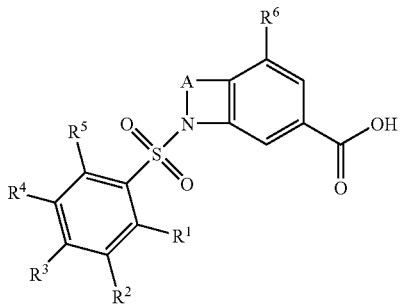

(VI)

with a compound of formula (VII)

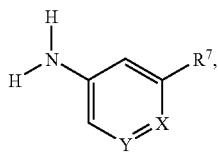

(VII)

wherein $R^1$, $R^2$, $R^3$, $R^4$, $R^5$, $R^6$, $R^7$, A, X and Y are as defined above.

The reaction of a compound of formula (IV) with a compound of formula (V) can be carried out under conditions well known to the person skilled in the art. Such reactions of a compound of formula (IV) can conveniently be carried out for example by mixing a compound of formula (IV) with a compound of formula (V) in anhydrous solvents such as e.g. dichloromethane, tetrahydrofuran, acetonitrile, toluene and mixtures thereof at appropriate temperatures between 0° C. and 110° C., optionally in the presence of a base, as for example triethylamine, diisopropylethylamine or pyridine.

The reaction of a compound of formula (VI) with a compound of formula (VII) can be carried out under conditions well known to the person skilled in the art. Such reactions can conveniently be carried out for example by mixing a compound of formula (VI) with a compound of formula (VII) in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N-diisopropylethylamine, and a condensing agent, and optionally in the presence of an acylation catalyst such as 4-(dimethylamino)pyridine. Appropriate condensing agents can be for example O-(7-benzotriazol-1-yl)-N,N,N',N'-tetramethyluronium-tetrafluoroborate (TBTU), O-(7-azabenzotriazol-1-yl)-N,N,N',N'-tetramethyluronium-hexaflurophophate (HATU), N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluorophosphate, bromo-tris-pyrrolidino-phosphonium hexafluorophosphate or others well known to the person skilled in the art. Alternatively, such reaction can be performed in two steps involving first formation of the acyl halide derivative of the compound of formula (VI) and subsequent coupling reaction with an amine of formula (VII) in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropyl ethyl amine or N-methyl morpholine. The obtained acyl chloride can be isolated or reacted as such with an appropriate amine of formula (VII) in an aprotic solvent, like dichloromethane, tetrahydrofuran or acetone, in the presence of a base. Typical bases are triethylamine, N-methylmorpholine, pyridine, diisopropyl ethyl amine or dimethylaminopyridine or mixtures thereof.

The present invention also relates to compounds of formula (I) as defined above, when prepared by a process as described above.

The compounds of formula (I), (IV), (V), (VI) and (VII) can be prepared by methods known in the art or as described below or in analogy thereto. Unless otherwise indicated, $R^1$, $R^2$, $R^3$, $R^4$, $R^5$, $R^6$, $R^7$, A, X and Y are as described above.

Compounds of formula (I), wherein A is —CH$_2$—CH$_2$— can be represented by formula (II)

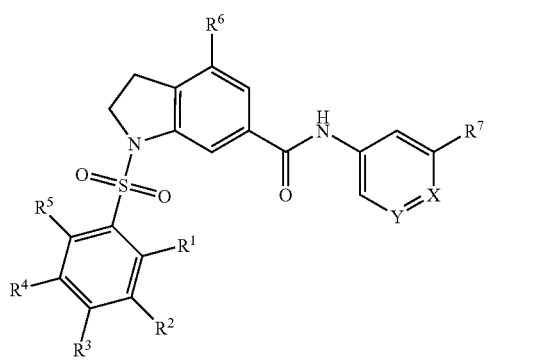

(II)

Compounds of formula (II) can be prepared according to the following general scheme (Scheme 1):

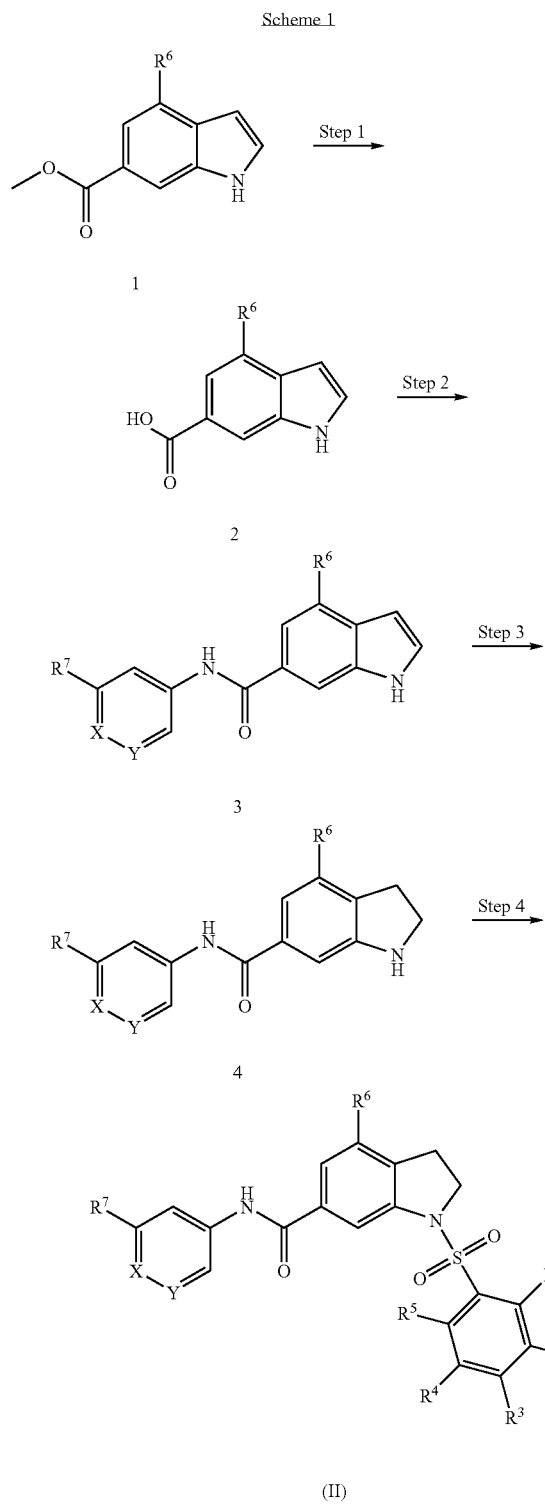

In step 1, substituted indole-6-carboxylic acid methyl ester 1 is converted into the corresponding carboxylic acid 2, using methods well known to someone skilled in the art, e.g. base mediated ester hydrolysis. The reaction is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate. In step 2, the carboxylic acid derivative 2 is converted, with the appropriate amine derivatives, into the corresponding amides of formula 3, using methods well known to someone skilled in the art, e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or diisopropylethylamine, and optionally in the presence of an acylation catalyst such as 4-(dimethylamino)-pyridine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. In step 3, scheme 1, the obtained compound of formula 3 is converted into the corresponding 2,3-dihydroindole of formula 4, using methods well known to someone skilled in the art, e.g. indole reduction. The reaction is typically carried out in protic solvents such as acetic acid, trifluoroacetic acid, and mixtures thereof at temperatures between 0° C. and 30° C. Typically used reducing reagents are sodium cyanoborohydride, sodium triacetoxyborohydride and sodium borohydride. In step 4 the obtained compounds of general formula 4 are converted into their corresponding sulphonamides of general formula 5, using methods well known to someone skilled in the art, e.g. sulphonylation of amines with sulphonyl chlorides. The reaction is typically carried out in anhydrous solvents such as dichloromethane, tetrahydrofuran, acetonitrile, toluene and mixtures thereof at temperatures between 0° C. and 110° C., optionally in the presence of a base like triethylamine, diisopropylethylamine or pyridine.

In a variation of scheme 1, intermediates of general formula 3 can be also accessed by aminolysis of the indole carboxylic acid methyl ester 1 according to scheme 2:

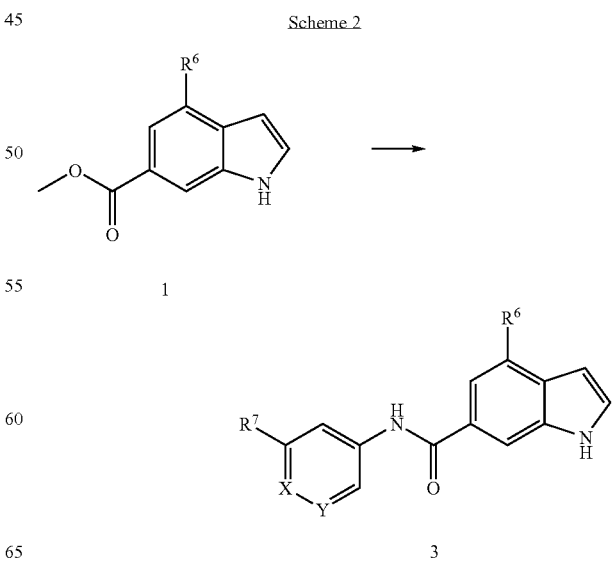

The reaction is typically carried out in aprotic solvents such as tetrahydrofuran, dioxane, dichloromethane and mixtures thereof at temperatures between −20° C. and 150° C., eventually with the use of microwave irradiation. Typical reagents are trimethylaluminum, triethylaluminum and tripropylaluminum.

In a further variation of scheme 1, compounds of general formula 4 can also be accessed by the pathway illustrated in scheme 3.

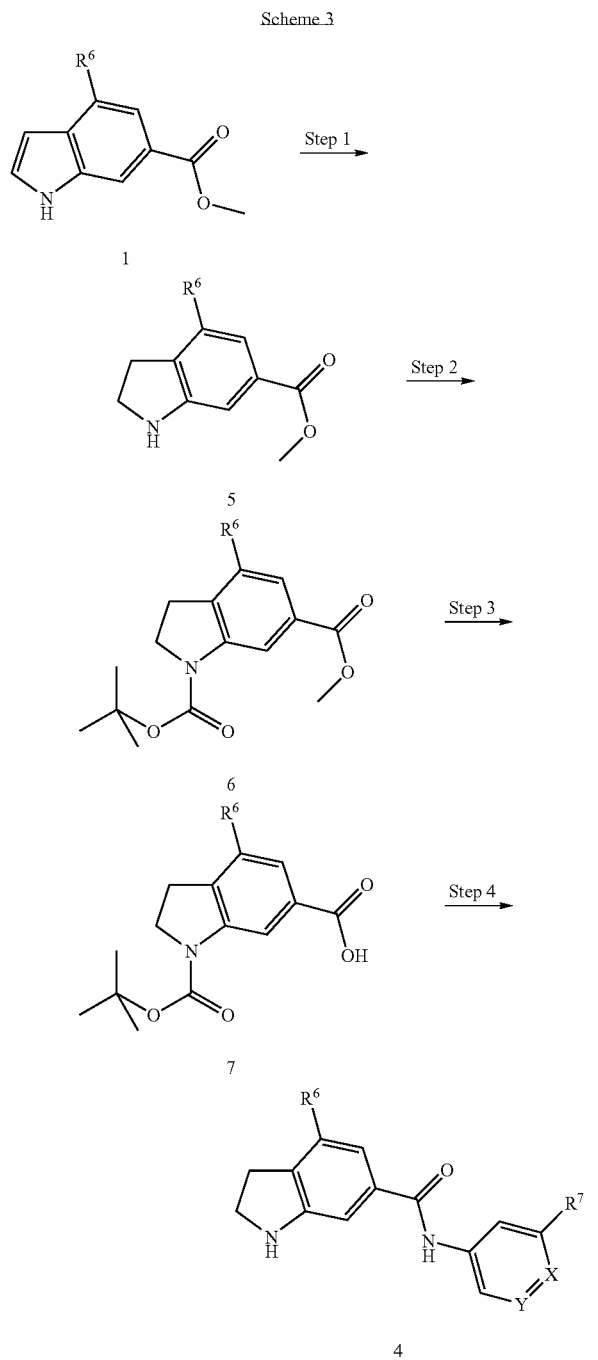

In step 1, scheme 3, substituted indole-6-carboxylic acid methyl ester 1 is converted into the corresponding 2,3-dihydroindole of formula 5, using methods well known to someone skilled in the art, e.g. indole reduction. The reaction is typically carried out in protic solvents such as acetic acid, trifluoroacetic acid, and mixtures thereof at temperatures between 0° C. and 30° C. Typically used reducing reagents are sodium cyanoborohydride, sodium triacetoxyborohydride and sodium borohydride. In step 2, scheme 3, the obtained compound of formula 5 is converted into the corresponding tert-butylcarbamate of formula 6, using methods well known to someone skilled in the art, e.g. tert-butylcarbamate protection under basic conditions. The reaction is typically carried out in aprotic solvents such as acetone, acetonitrile, tetrahydrofuran, N,N-dimethylformamide, N-methylpyrrolidinone, dioxane and mixtures thereof at temperatures between 20° C. and 100° C. Typically used bases are sodium hydride, potassium hydride, sodium methoxide, potassium tert-butoxide, triethylamine, N,N-diisopropylethylamine, pyridine and potassium carbonate. In step 3, scheme 3, the obtained compound of the formula 6 is converted into the corresponding carboxylic acid of the formula 7, using methods well known to someone skilled in the art, e.g. base mediated ester hydrolysis. The reaction is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate. Step 4, scheme 3, is a two step process in which the carboxylic acid derivative of the formula 7 is converted, with the appropriate amine derivatives, into the corresponding amide and the tert-butylcarbamate group is removed to give the compounds of formula 4, using methods well known to someone skilled in the art, e.g. amide formation using a coupling reagent and acid mediated tert-butylcarbamate deprotection. The first step (amide formation) is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N-diisopropylethylamine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. The second step (tert-butylcarbamate deprotection) is typically carried out with or without solvents such as dichloromethane, dioxane and tetrahydrofuran and mixtures thereof at temperature between 0° C. and 60° C. Typically used acids are hydrogen chloride, concentrated hydrochloric acid and trifluoroacetic acid. The obtained compounds of the formula 4 are converted into compounds of general formula II according to what illustrated in scheme 1.

Alternatively, compounds of formula (II) can be accessed as illustrated in scheme 4.

Scheme 4

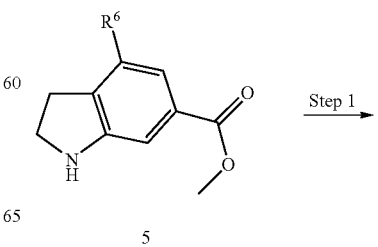

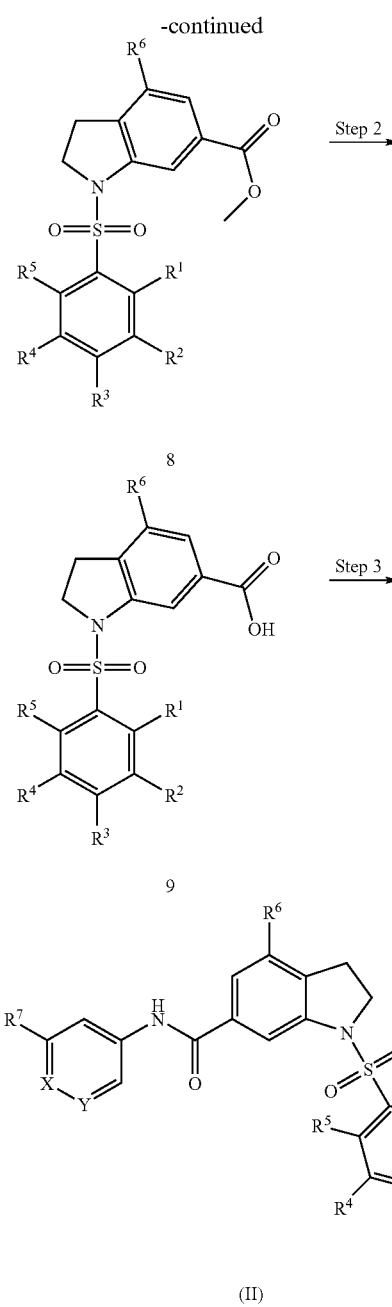

potassium hydroxide, sodium hydrogen carbonate, sodium carbonate, potassium hydrogen carbonate and potassium carbonate. In step 3, scheme 4, the carboxylic acid derivatives of the formula 9 are converted, with the appropriate amine derivatives, into the corresponding amide using methods well known to someone skilled in the art, e.g. amide formation using a coupling reagent. This is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N-diisopropylethylamine, and optionally in the presence of an acylation catalyst such as 4-(dimethylamino)pyridine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. Alternatively, such reaction can be performed in two steps involving first formation of the acyl halide derivative of 9 and subsequent coupling reaction with an appropriate amine in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropyl ethyl amine or N-methyl morpholine. The obtained acyl chloride can be isolated or reacted as such with an appropriate amine in an aprotic solvent, like dichloromethane, tetrahydrofuran or acetone, in the presence of a base. Typical bases are triethylamine, N-methylmorpholine, pyridine, diisopropyl ethyl amine or dimethylaminopyridine or mixtures thereof.

Compounds of formula (I), wherein A is —CH$_2$CH$_2$CH$_2$— can be represented by formula (III)

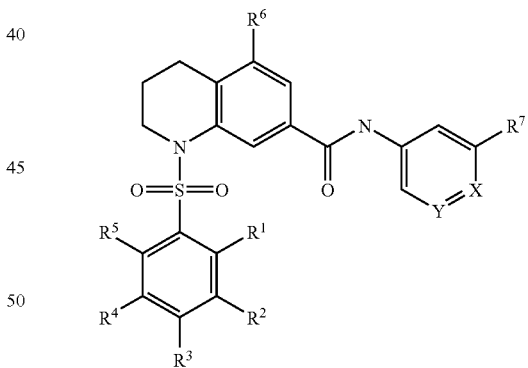

In step 1, Scheme 4, the 2,3-dihydroindoles of formula 5 are converted into their corresponding sulphonamides of general formula 8, using methods well known to someone skilled in the art, e.g. sulphonylation of amines with sulphonyl chlorides. The reaction is typically carried out in anhydrous solvents such as dichloromethane, tetrahydrofuran, acetonitrile, toluene and mixtures thereof at temperatures between 0° C. and 110° C., optionally in the presence of a base like triethylamine, diisopropylethylamine or pyridine. In step 2, scheme 4, the obtained compound of the formula 8 is converted into the corresponding carboxylic acid of the formula 9, using methods well known to someone skilled in the art, e.g. base mediated ester hydrolysis. The reaction is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, Compounds of general formula (III) can be accessed according to the following general scheme (Scheme 5):

Scheme 5

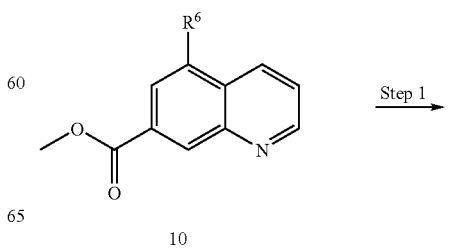

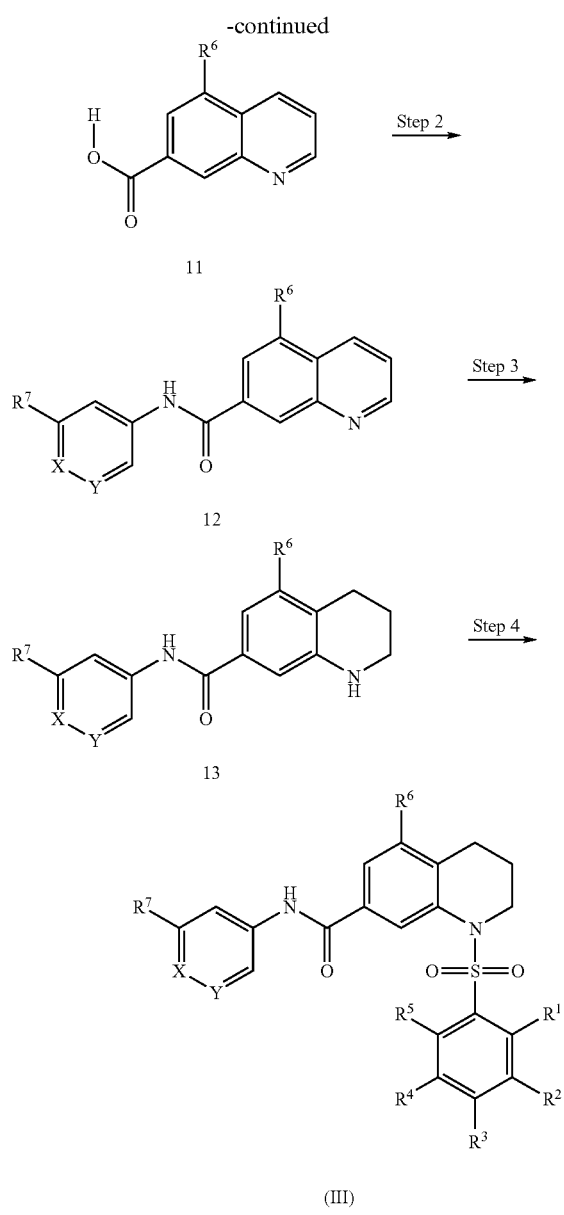

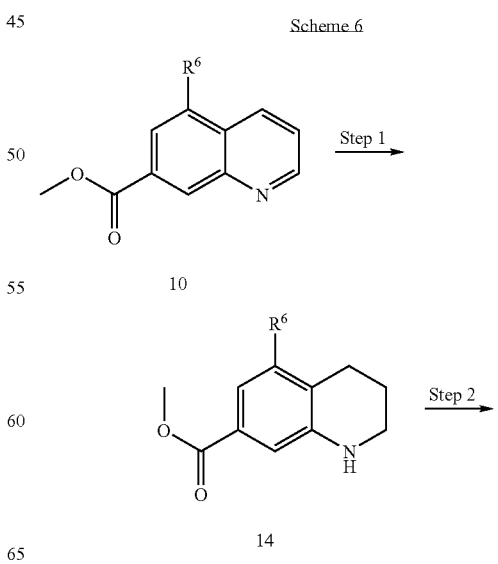

tives, into the corresponding amides of formula 12, using methods well known to someone skilled in the art e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or diisopropylethylamine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluorophosphate, O-(7-azabenzotriazol-1-yl)-N,N,N',N'-tetramethyluronium hexafluoro-phosphate and bromo-tris-pyrrolidino-phosphonium hexafluorophosphate. In step 3, scheme 5, the obtained compounds of the formula 12 are converted into their corresponding 1,2,3,4-tetrahydroquinolines of the formula 13, using methods well known to someone skilled in the art, e.g. quinoline reduction. The reaction is typically carried out in solvents such as water, isopropanol, ethylene glycol, trifluoroacetic acid, tetrahydrofuran and mixtures thereof at temperatures between 20° C. and 160° C. with hydrogen or a hydrogen transfer reagent such as isopropanol in the presence or absence of a mineral acid such as perchloric acid or HCl. Typically used catalysts are polymer encapsulated palladium, pentamethylcycloopentadienyliridium(III) chloride dimer, Raney nickel, platinum oxide and other transition metal catalysts. In step 4, scheme 5, the obtained compounds of the formula 13 are converted into their corresponding sulphonamides of the general formula (III), using methods well known to someone skilled in the art, e.g. sulphonylation of amines with sulphonyl chlorides. The reaction is typically carried out in anhydrous solvents such as dichloromethane, tetrahydrofuran, acetonitrile, toluene and mixtures thereof at temperatures between 0° C. and 110° C., optionally in the presence of a base like triethylamine, diisopropylethylamine or pyridine.

Alternatively, compounds of general formula (III) can be accessed as described in the general scheme 6:

The method for the synthesis of the compounds of formula (III) starts from quinoline-7-carboxylic acid methyl esters 10. In step 1, scheme 5, quinoline-7-carboxylic acid methyl esters of the formula 10 are converted into the corresponding carboxylic acid of the formula 11, using methods well known to someone skilled in the art, e.g. base mediated ester hydrolysis. Quinoline-7-carboxylic acid methyl ester 10 can readily be prepared by someone skilled in the art using the literature procedure detailed in: *Bioorg. Med. Chem. Lett.*, 1999, 9, 1403-1408. The reaction is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate.

In step 2, scheme 5, the carboxylic acid derivatives of the formula 11 are converted, with the appropriate amine deriva-

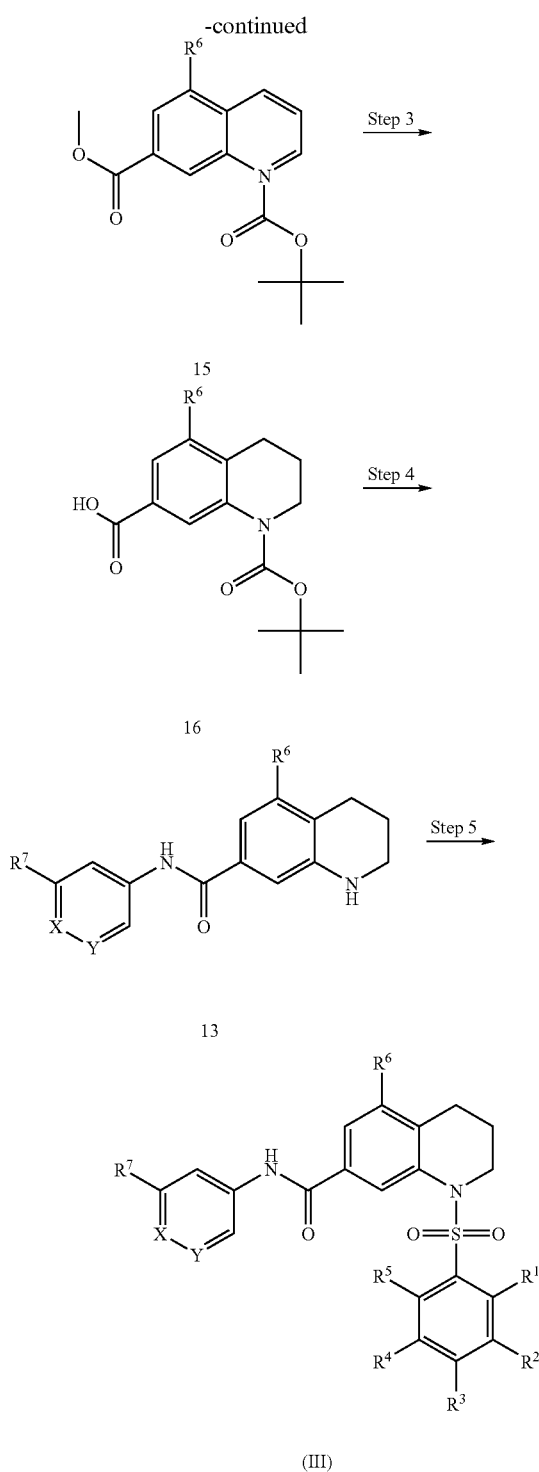

In step 1, scheme 6, quinoline-7-carboxylic acid methyl esters 10 are converted into their corresponding 1,2,3,4-tetrahydroquinolines of the formula 14, using methods well known to someone skilled in the art, e.g. quinoline reduction. The reaction is typically carried out in solvents such as water, isopropanol, ethylene glycol, trifluoro acetic acid, tetrahydrofuran and mixtures thereof at temperatures between 20° C. and 160° C. with hydrogen or a hydrogen transfer reagent such as isopropanol in the presence or absence of a mineral acid such as perchloric acid or HCl. Typically used catalysts are polymer encapsulated palladium, pentamethylcyclopentadienyliridium(III) chloride dimer, Raney nickel, platinum oxide and other transition metal catalysts. In step 2, scheme 6, the obtained compounds of the formula 14 is converted into the corresponding tert-butylcarbamate of formula 15, using methods well known to someone skilled in the art, e.g. tert-butylcarbamate protection under basic conditions. The reaction is typically carried out in aprotic solvents such as acetone, acetonitrile, tetrahydrofuran, N,N-dimethylformamide, N-methylpyrrolidinone, dioxane and mixtures thereof at temperatures between 20° C. and 100° C. Typically used bases are sodium hydride, potassium hydride, sodium methoxide, potassium tert-butoxide, triethylamine, N,N-diisopropylethylamine, pyridine and potassium carbonate. In step 3, scheme 6, the obtained compound of the formula 15 is converted into the corresponding carboxylic acid of the formula 16, using methods well known to someone skilled in the art, e.g. base mediated ester hydrolysis. The reaction is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate. Step 4, scheme 6, is a two step process in which the carboxylic acid derivative of the formula 16 is converted, with the appropriate amine derivatives, into the corresponding amide and the tert-butylcarbamate group is removed to give the compounds of formula 13, using methods well known to someone skilled in the art, e.g. amide formation using a coupling reagent and acid mediated tert-butylcarbamate deprotection. The first step (amide formation) is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N-diisopropylethylamine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. The second step (tert-butylcarbamate deprotection) is typically carried out with or without solvents such as dichloromethane, dioxane and tetrahydrofuran and mixtures thereof at temperature between 0° C. and 60° C. Typically used acids are hydrogen chloride, concentrated hydrochloric acid and trifluoroacetic acid. The obtained compounds of the formula 13 are converted into compounds of general formula (II) according to what illustrated in scheme 5.

Compounds of general formula (I) wherein X is $CR^8$ and $R^8$ is COOH are represented by the general formula (Ia).

(Ia)

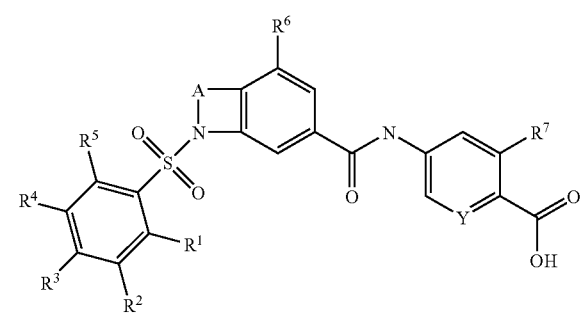

Compounds of formula (Ia) are synthesised starting from the esters 17, as illustrated in scheme 7.

Scheme 7

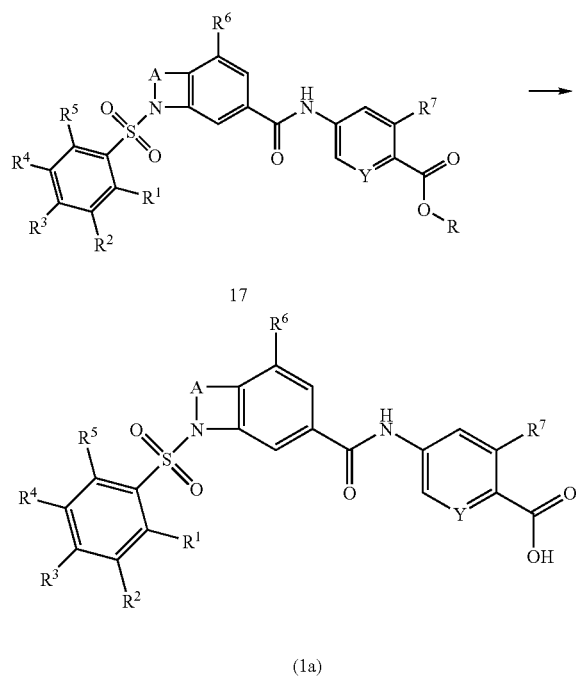

17

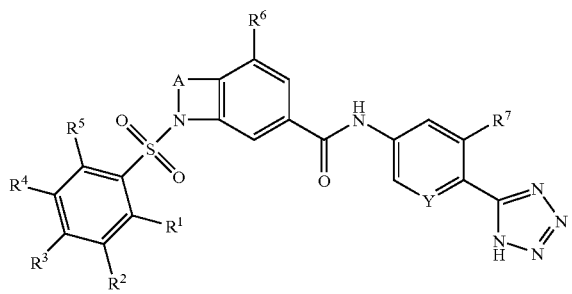

(Ia)
(R = Me, Et, etc.)

Esters 17 are obtained as described above in schemes 1-6 by employing an appropriate 4-(alkoxycarbonyl)-phenylamine in the amide formation steps. Esters 17 are converted into their corresponding carboxylic acids of the formula Ia, using methods well known to someone skilled in the art, e.g. acid- or base-mediated ester hydrolysis. The reaction is typically carried out in solvents such as water, methanol, tetrahydrofuran, 1,4-dioxane and mixtures thereof at temperatures between −20° C. and 120° C. Typical reagents for base-mediated ester hydrolysis are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate. Preferred reagents for acid-mediated ester hydrolysis are formic acid, hydrogen chloride, and trifluoroacetic acid.

Compounds of general formula (I) wherein X is $CR^8$ and $R^8$ is an acid isostere such as 1H-tetrazol-5-yl are represented by the general formula (Ib).

(Ib)

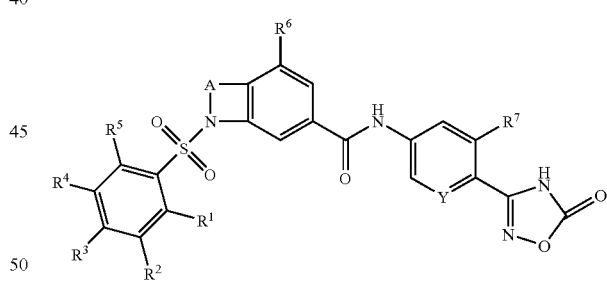

Compounds of general formula (Ib) can be prepared for example starting from nitriles 18, as illustrated in scheme 8.

Scheme 8

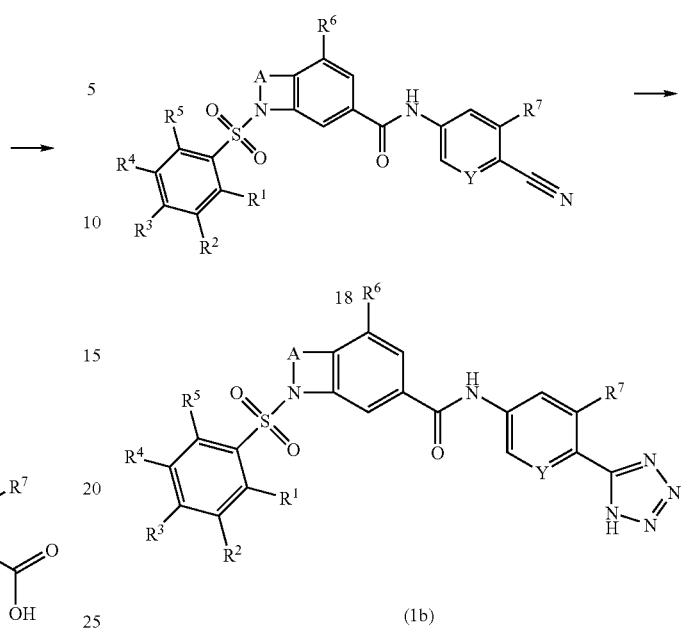

(1b)

Nitriles 18 are obtained as described above in schemes 1-6 by employing an appropriate 4-aminobenzonitrile in the amide formation steps. Nitriles 18 are converted to the corresponding 1H-tetrazoles using methods well known to somebody skilled in the art, e.g. dipolar cycloaddition with azides. The reaction is typically carried out in an aprotic solvent like dimethylformamide, dimethylsulfoxide, tetrahydrofuran at temperatures between 25° C. and 200° C., optionally under microwave irradiation, using an azide source like ammonium azide, sodium azide or trialkyltin azide.

Compounds of general formula (I) wherein X is $CR^8$ and $R^8$ is an acid isostere such as 4H-[1,2,4]oxadiazol-3-yl-5-one are represented by the general formula (Ic).

(Ic)

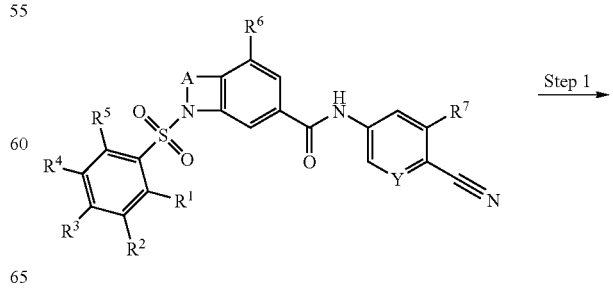

Compounds of general formula (Ic) can be prepared for example starting from nitriles 18, as illustrated in scheme 9.

Scheme 9

18

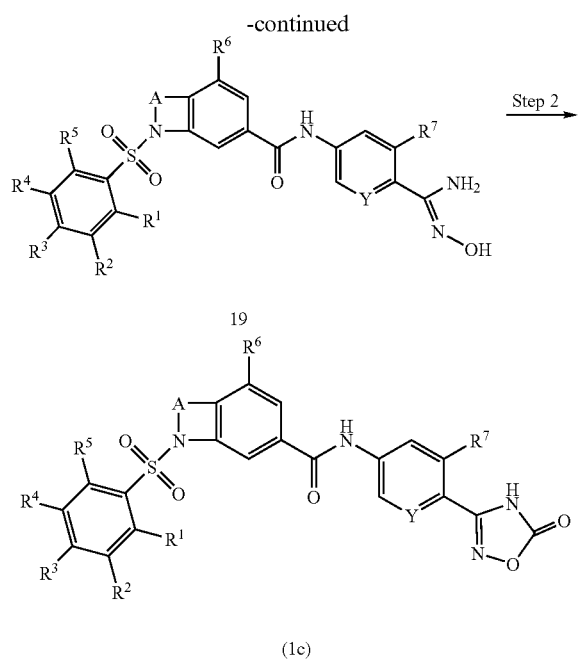

(1c)

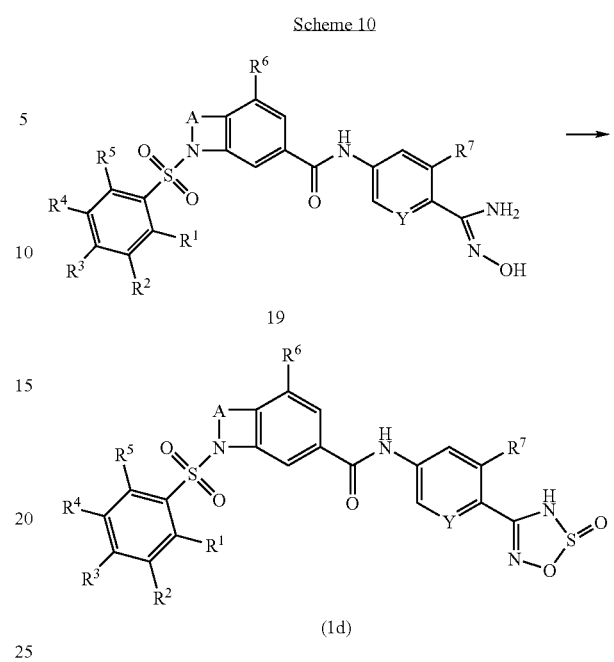

(1d)

In step 1, scheme 9, benzonitriles of general formula 18 are converted to N-hydroxy-benzamidines 19 using methods well known to somebody skilled in the art, e.g. nucleophilic addition with hydroxylamine. The reactions is typically carried out in an aprotic solvent like dimethylformamide, dimethylsulfoxide, tetrahydrofuran, acetonitrile, at temperatures between 0° C. and 150° C. in the presence of a base like triethylamine, diisopropylethylamine, N-methylmorpholine or pyridine. The obtained N-hydroxybenzamidines 19 can be converted to compounds of general formula (Ic) using methods well known to somebody skilled in the art, e.g. intramolecular carbamate formation. The reaction is typically carried out in an aprotic solvent like benzene, toluene, xylene, dimethylformamide, dimethylsulfoxide or mixtures thereof at temperatures between 0° C. and 200° C. in the presence of a base. Typical reagents for the formations of the carbamate are phosgene, triphosgene, carbonyldiimidazole, cholorformic acid alkyl esters, and the like. Typical bases are triethylamine, diisopropylethylamine, N-methylmorpholine or pyridine.

Compounds of general formula (I) wherein X is $CR^8$ and $R^8$ is an acid isostere such as 3H-[1,2,3,5]oxathiadiazol-4-yl-2-oxide are represented by the general formula (Id).

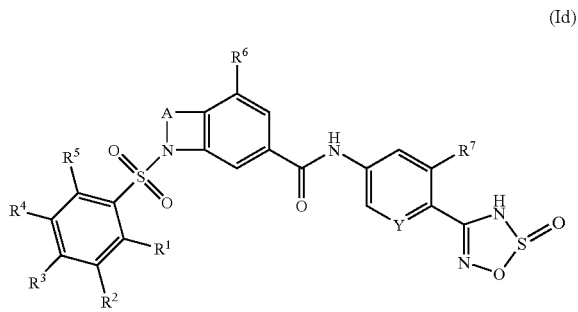

(Id)

Compounds of general formula (Id) can be prepared for example starting from N-hydroxy-benzamidines 19, as illustrated in scheme 10.

N-Hydroxy-benzamidines 19 can be converted to compounds of general formula Id using methods well known to somebody skilled in the art, e.g. intramolecular sulfinamidate formation. The reaction is typically carried out in an aprotic solvent like dimethylformamide, dimethylsulfoxide, acetonitrile, tetrahydrofuran or dichloromethane or mixtures thereof in the presence of a base. A typically used reagent is thionyl chloride and typical bases are triethylamine, disopropylethylamine, N-methylmorpholine or pyridine.

Compounds of general formula (I) where X is $CR^8$ and $R^8$ is an acid isostere such as 4H-[1,2,4]oxadiazol-3-yl-5-thione are represented by the general formula (Ie).

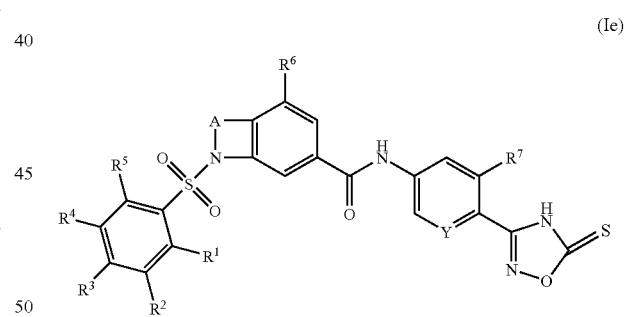

(Ie)

Compounds of general formula (Ie) can be prepared for example starting from N-hydroxy-benzamidines 19, as illustrated in scheme 11.

Scheme 11

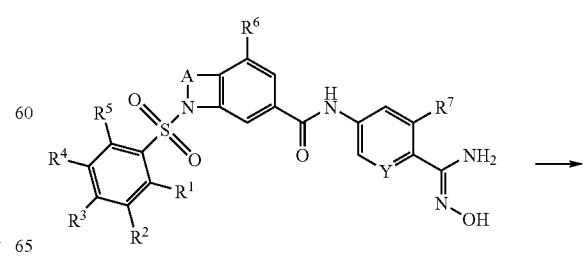

19

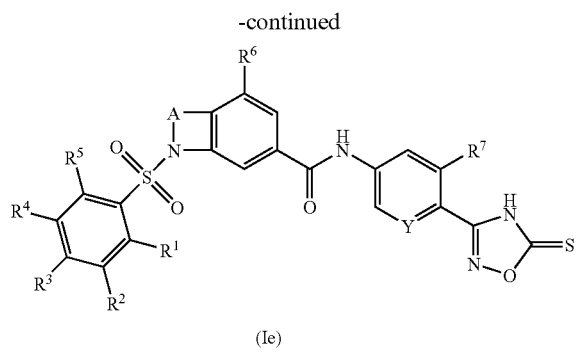

(Ie)

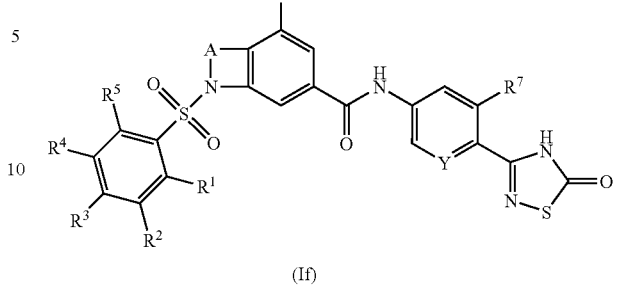

(If)

N-Hydroxy-benzamidines 19 can be converted to compounds of general formula (Ie) using methods well known to somebody skilled in the art, e.g. intramolecular thiocarbamate formation. The reaction is typically carried out in an aprotic solvent like dimethylformamide, dimethylsulfoxide, acetonitrile, tetrahydrofuran or dichloromethane or mixtures thereof in the presence of a base. A typically used reagent is 1,1'-thiocarbonyldiimidazole and typical bases are triethylamine, diisopropylethylamine, N-methylmorpholine, 1,8-diazabicyclo[5.4.0]undec-7-ene (DBU), 1,5-diazabicyclo[4.3.0]non-5-ene and the like or pyridine.

Compounds of general formula (I) wherein X is $CR^8$ and $R^8$ is an acid isostere such as 4H-[1,2,4]thiadiazol-3-yl-5-one, are represented by the general formula (If).

N-Hydroxy-benzamidines 19 can be converted to compounds of general formula (If) using methods well known to somebody skilled in the art, e.g. intramolecular thiocarbamate formation. The reaction is typically carried out in an aprotic solvent like dimethylformamide, dimethylsulfoxide, acetonitrile, tetrahydrofuran or dichloromethane or mixtures thereof in the presence of a Lewis acid. A typically used reagent is 1,1'-thiocarbonyldiimidazole and a typical acid is boron trifluoride.

Compounds of general formula (I) where X is $CR^8$ and $R^8$ is 1-hydroxy-lower-alkyl are represented by the general formula (Ig).

(If)

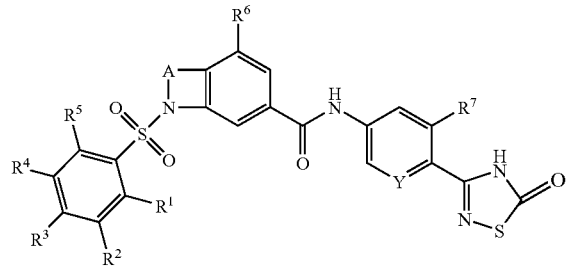

Compounds of general formula (If) can be prepared for example starting from N-hydroxy-benzamidines 19, as illustrated in scheme 12.

(Ig)

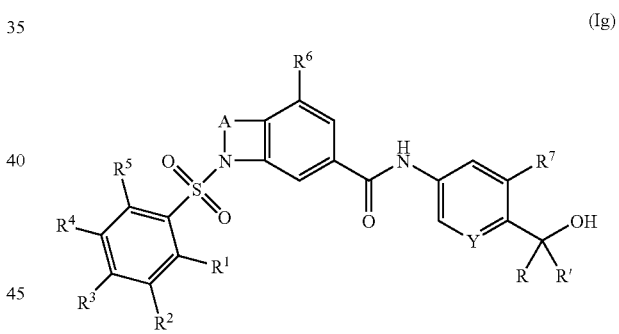

Compounds of general formula (Ig) can be prepared for example starting from ketones of general formula 20, as illustrated in scheme 13.

Scheme 12

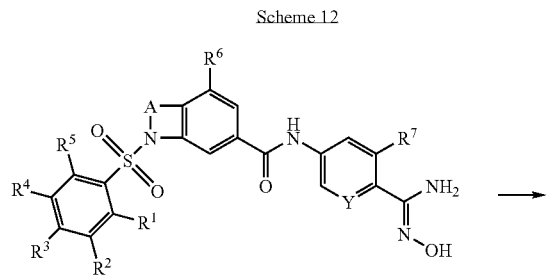

19

Scheme 13

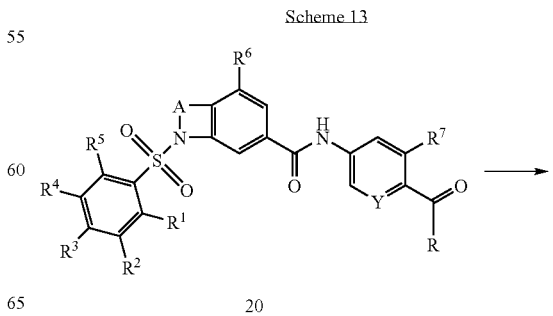

20

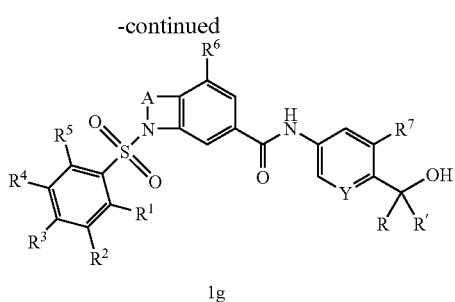

1g

Ketones 20 are obtained as described above in schemes 1-6 by employing an appropriate 4-alkylcarbonyl phenyl amine in the amide formation steps. Ketones 20 can be converted to compounds of general formula Ig using methods well known to somebody skilled in the art, e.g. Grignard addition or addition of other organometallic reagents, or reagents capable of generating a nucleophilic carbon under the reaction conditions. The reaction is typically carried out in an aprotic solvent like tetrahydrofuran, ether or dichloromethane or mixtures thereof at temperatures between −80° C. and 25° C. under anhydrous conditions.

Compounds of general formula (I) wherein A is —C($R^{10}R^{11}$)C($R^{12}R^{13}$)C($R^{14}R^{15}$)C($R^{16}R^{17}$)— can be prepared starting from commercially available α-tetralone using methods well known to somebody skilled in the art. The aromatic ketone is brominated to 7-bromo-3,4-dihydro-2H-naphthalen-1-one using methods well known to somebody skilled in the art, i.e. aromatic electrophilic bromination. The reaction is carried out in a solvent, for example dichloromethane, at temperatures between 25° C. and 150° C. using elemental bromine as bromine source in the presence of a Lewis acid. Typically used Lewis acids are aluminum trichloride or aluminum tribromide. The obtained 7-bromo-3,4-dihydro-2H-naphthalen-1-one is converted to 8-bromo-1,3,4,5-tetrahydro-benzo[b]azepin-2-one using methods well known to somebody skilled in the art, i.e. Schmidt rearrangement. The reaction is carried out in a protic solvent, like for example acetic acid, in the presence of a nitrogen source, like for example ammonium azide, and an acid, like for example sulfuric acid. The obtained 8-bromo-1,3,4,5-tetrahydro-benzo[b]azepin-2-one is then reduced to 8-bromo-2,3,4,5-tetrahydro-1H-benzo[b]azepine using methods well known to somebody skilled in the art, i.e. amide reduction. The reaction is typically carried out in an ethereal solvent, like for example ether or tetrahydrofuran, using lithium aluminium hydride or diborane as reducing agents. The amino group of the obtained 8-bromo-2,3,4,5-tetrahydro-1H-benzo[b]azepine is then reacted with a sulfonyl chloride to form the corresponding sulfonamides, in analogy to what described above. The obtained 1-arylsulfonyl-8-bromo-2,3,4,5-tetrahydro-1H-benzo[b]azepines are converted to the corresponding 1-arylsulfonyl-2,3,4,5-tetrahydro-1H-benzo[b]azepine-8-carboxylic acid alkyl esters using methods well known to somebody skilled in the art, i.e. palladium catalyzed alkoxycarbonylation. The reaction is typically carried out in an alcoholic solvent, like for example methanol, or in a mixture of an alcoholic solvent with an aprotic solvent, like toluene, at temperatures between 25° C. and 150° C. under an atmosphere of carbon monoxide at pressures between 1 atm and 100 atm or in the presence of an agent capable of liberating carbon monoxide under the reaction conditions, like for example molybdenum hexacarbonyl. Typically used palladium catalysts are palladium dichloride, palladium acetate, palladium tetrakis(triphenylphosphine) or palladium bis(dibenzylideneacetone) dichloride. The obtained 1-arylsulfonyl-2,3,4,5-tetrahydro-1H-benzo[b]azepine-8-carboxylic acid alkyl esters are elaborated to final products of formula (I) through hydrolysis and amide formation, in analogy to what described above.

Compounds of general formula (I) wherein A is —C($R^{10}R^{11}$)C($R^{12}R^{13}$)C($R^{14}R^{15}$)C($R^{16}R^{17}$)C($R^{18}R^{19}$)— can be prepared starting from 1-benzosuberone in an analogous way.

Compounds of formula (I) where X is an acid or an acid isostere can form salts with physiologically compatible bases. Examples of such salts are alkaline, earth-alkaline and ammonium salts such as e.g. Na—, K—, Ca— and trimethylammonium salt. One method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, *Biochem. J.* 341, 483-489 and Jackson et al., 2000, *J. Biol. Chem.* 275, 19560-19566.

Human liver and muscle CPT1 cDNAs and rat CPT2 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 µM) and palmitoyl-CoA (80 µM) reduced DTNB (300 µM) forming 5-mercapto-(2-nitrobenzoic acid) which absorbed at 410 nm with a molar coefficient extinction of 13600 $M^{-1} \cdot cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an $IC_{50}$ value below 10 µM, preferably 10 nM to 10 µM, more preferably 10 nM to 5 µM. The following table shows data for some examples.

| Example | L-CPT1 inhibition $IC_{50}$ [µmol/l] |
| --- | --- |
| 1 | 0.1601 |
| 12 | 0.0722 |
| 31 | 0.0206 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspension of infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert therapeutically compatible solid or liquid carrier materials and, if desired, usual pharmaceutical adjuvants.

Suitable carrier materials are not only inorganic carrier materials, but also organic carrier material. Thus, for example, lactose, corn starch or derivatives thereof, talc, stearic acid or its salt can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner.

EXAMPLES

Example 1

2-Chloro-4-{[1-(3-chloro-benzenesulfonyl)-2,3-dihydro-1H-indole-6-carbonyl]-amino}-benzoic acid The title compound was prepared as illustrated in schemes 1 and 7.

Step 1:

Lithium hydroxide (0.72 g, 17.2 mmol, 3 equiv.) in water (10 mL) was added to methyl indole-6-carboxylate (1 g, 5.7 mmol, 1 equiv.) in tetrahydrofuran (10 mL) and the mixture stirred at 80° C. for 16 hours. The solution was concentrated under vacuum then diluted with dichloromethane (10 mL) and the organic layer extracted with water (3×10 mL). The aqueous phase was acidified to pH<1 with concentrated HCl forming a precipitate. The precipitate was filtered and washed with 1 M aqueous HCl (3×10 mL) to afford 1H-indole-6-carboxylic acid as a white solid, 0.807 g (88% yield). LC @215 nm; Rt 1.02: 100%, m/z (ES+): 162 (M+H$^+$.); $\delta_H$ (400 MHz; MeOD) 8.15 (1H, d), 7.72 (1H, m), 7.67 (1H, m), 7.45 (1H, m), 6.53 (1H, m).

Step 2:

Bromo-tris-pyrrolidino-phosphonium hexafluorophosphate (8.3 g, 17.8 mmol, 1.1 equiv.) and diisopropyl ethyl amine (4.4 ml, 33.9 mmol, 2.1 equiv.) were added to 1H-indole-6-carboxylic acid (2.6 g, 16.2 mmol, 1 equiv.) in tetrahydrofuran (30 mL) and the mixture was shaken for 5 minutes at room temperature. 4-Amino-2-chlorobenzoic acid methyl ester (3.3 g, 17.9 mmol, 1.1 equiv.) was added and the resultant mixture was shaken at room temperature for 16 hours. The solvent was removed under vacuum and the residue triturated with dichloromethane (10 mL). The solid was filtered to afford 2-chloro-4-[(1H-indole-6-carbonyl)-amino]-benzoic acid methyl ester, 1.4 g (26% yield). LC @215 nm; Rt 1.36: 90%, m/z (M+H$^+$.): 329 (M+H$^+$.); $\delta_H$ (400 MHz; d6-DMSO) 11.65 (1H, s), 10.59 (1H, s), 8.16 (1H, s), 8.10 (1H, s), 7.93 (2H, m), 7.65 (2H, s), 7.59 (1H, m), 6.62 (1H, s), 3.85 (3H, s).

Step 3:

Sodium cyanoborohydride (2.6 g, 41.6 mmol, 3 equiv.) was added to a stirred solution of 2-chloro-4-[(1H-indole-6-carbonyl)-amino]-benzoic acid methyl ester (1.4 g, 4.2 mmol, 1 equiv.) in acetic acid (25 mL) over 5 minutes at room temperature. The mixture was stirred for 30 minutes then cooled to 0° C. and poured onto concentrated ammonium hydroxide (78 mL, d=0.880) at 0° C. The mixture was diluted with water (25 mL) and dichloromethane (25 mL), the organic layer was separated and the aqueous layer extracted with dichloromethane (2×25 mL). The combined organic layers were dried over Na$_2$SO$_4$ and the solvent removed under vacuum to afford crude 2-chloro-4-[(2,3-dihydro-1H-indole-6-carbonyl)-amino]-benzoic acid methyl ester, 0.75 g, this material was taken onto the next step without further purification. LC @215 nm; Rt 1.04: 71%, m/z (ES+): 331 (M+H$^+$.).

Step 4:

3-Chlorobenzenesulphonyl chloride (71 mg, 0.3 mmol, 1.1 equiv.) was added to a mixture of crude 2-chloro-4-[(2,3-dihydro-1H-indole-6-carbonyl)-amino]-benzoic acid methyl ester (100 mg, 0.3 mmol, 1 equiv.) and pyridine (0.2 mL, 2.4 mmol, 8 equiv.) in dichloromethane (2 ml) and the mixture was stirred at room temperature for 16 hours. The solvent was removed under a stream of N$_2$ and the residue purified by column chromatography (SiO$_2$, dichloromethane). The fractions were combined to afford crude 2-chloro-4-{[1-(3-chloro-benzenesulfonyl)-2,3-dihydro-1H-indole-6-carbonyl]-amino}-benzoic acid methyl ester, 101 mg. This material was taken onto the next step without further purification. LC @215 nm; Rt 2.52: 84%, m/z (ES+): 505 (M+H$^+$.).

Step 5:

A 3 N aqueous KOH solution (2 mL) was added to a mixture of crude 2-chloro-4-{[1-(3-chloro-benzenesulfonyl)-2,3-dihydro-1H-indole-6-carbonyl]-amino}-benzoic acid methyl ester (67 mg, 0.13 mmol, 1 equiv.) in tetrahydrofuran (2 mL) and methanol (1 mL) and the mixture was shaken at room temperature for 16 hours. The mixture was concentrated under a stream of N$_2$ and the solution adjusted to pH 7 with 3 N aqueous HCl solution (2 mL), forming a precipitate. The precipitate was filtered to afford 2-chloro-4-{[1-(3-chloro-benzenesulfonyl)-2,3-dihydro-H-indole-6-carbonyl]-amino}-benzoic acid, 63 mg (90% yield). LC @215 nm; Rt 1.53: 96%, m/z (ES+): 491.19 (M+H$^+$.); $\delta_H$ (400 MHz; d6-DMSO) 10.67 (1H, br.s), 8.11 (1H, s), 8.03 (1H, s), 7.80-7.94 (5H, m), 7.71 (1H, d), 7.66 (1H, t), 7.39 (1H, d), 4.07 (2H, t), 3.04 (2H, t).

Example 2

2-Chloro-4-{[1-(5-chloro-2-methoxy-benzenesulfonyl)-2,3-dihydro-1H-indole-6-carbonyl]-amino}-benzoic acid 2-Chloro-4-{[1-(5-chloro-2-methoxy-benzenesulfonyl)-2,3-dihydro-1H-indole-6-carbonyl]-amino}-benzoic acid, m/z (ES+): 521.18 (M+H$^+$.), was prepared in analogy to example 1, steps 1 to 5. Step 4 was performed using 5-chloro-2-methoxy-benzenesulfonyl chloride and yielded 2-chloro-4-{[1-(5-chloro-2-methoxy-benzenesulfonyl)-2,3-dihydro-1H-indole-6-carbonyl]-amino}-benzoic acid methyl ester, which was hydrolyzed in step 5.

Example 3

2-Chloro-4-{[1-(3-trifluoromethyl-benzenesulfonyl)-2,3-dihydro-1H-indole-6-carbonyl]-amino}-benzoic acid 2-Chloro-4-{[1-(3-trifluoromethyl-benzenesulfonyl)-2,3-dihydro-1H-indole-6-carbonyl]-amino}-benzoic acid, m/z (ES+): 525.23 (M+H$^+$.), was prepared in analogy to example 1, steps 1 to 5. Step 4 was performed using 3-trifluoromethyl-benzenesulfonyl chloride and yielded 2-chloro-4-{[1-(3-trifluoromethyl-benzenesulfonyl)-2,3-dihydro-1H-indole-6-carbonyl]-amino}-benzoic acid methyl ester, which was hydrolyzed in step 5.

Example 4

2-Chloro-4-{[1-(3,4-dichloro-benzenesulfonyl)-2,3-dihydro-1H-indole-6-carbonyl]-amino}-benzoic acid 2-Chloro-4-{[1-(3,4-dichloro-benzenesulfonyl)-2,3-dihydro-1H-indole-6-carbonyl]-amino}-benzoic acid, m/z (ES+): 525.18 (M+H$^+$.), was prepared in analogy to example 1, steps 1 to 5. Step 4 was performed using 3,4-dichloro-benzene-sulfonyl chloride and yielded 2-chloro-4-{[1-(3,4-dichloro-benzenesulfonyl)-2,3-dihydro-1H-indole-6-carbonyl]-amino}-benzoic acid methyl ester, which was hydrolyzed in step 5.

Example 5

2-Chloro-4-{[1-(3,5-dichloro-benzenesulfonyl)-2,3-dihydro-1H-indole-6-carbonyl]-amino}-benzoic acid 2-Chloro-4-{[1-(3,5-dichloro-benzenesulfonyl)-2,3-dihydro-1H-indole-6-carbonyl]-amino}-benzoic acid, m/z (ES+): 525.21 (M+H$^+$.), was prepared in analogy to example 1, steps 1 to 5. Step 4 was performed using 3,5-dichloro-benzene-sulfonyl chloride and yielded 2-chloro-4-{[1-(3,5-dichloro-benzenesulfonyl)-2,3-dihydro-1H-indole-6-carbonyl]-amino}-benzoic acid methyl ester, which was hydrolyzed in step 5.

Example 6

2-Chloro-4-{[1-(3-fluoro-benzenesulfonyl)-2,3-dihydro-1H-indole-6-carbonyl]-amino}-benzoic acid 2-Chloro-4-{[1-(3-fluoro-benzenesulfonyl)-2,3-dihydro-1H-indole-6-carbonyl]-amino}-benzoic acid, m/z (ES+): 475.22 (M+H$^+$.), was prepared in analogy to example 1, steps 1 to 5. Step 4 was performed using 3-fluoro-benzenesulfonyl chloride and yielded 2-chloro-4-{[1-(3-fluoro-benzenesulfonyl)-2,3-dihydro-1H-indole-6-carbonyl]-amino}-benzoic acid methyl ester, which was hydrolyzed in step 5.

Example 7

2-Chloro-4-{[1-(2-methoxy-5-methyl-benzenesulfonyl)-2,3-dihydro-1H-indole-6-carbonyl]-amino}-benzoic acid 2-Chloro-4-{[1-(2-methoxy-5-methyl-benzenesulfonyl)-2,3-dihydro-1H-indole-6-carbonyl]-amino}-benzoic acid, m/z (ES+): 501.26 (M+H$^+$.), was prepared in analogy to example 1, steps 1 to 5. Step 4 was performed using 2-methoxy-5-methyl-benzenesulfonyl chloride and yielded 2-chloro-4-{[1-(2-methoxy-5-methyl-benzenesulfonyl)-2,3-dihydro-1H-indole-6-carbonyl]-amino}-benzoic acid methyl ester, which was hydrolyzed in step 5.

Example 8

2-Chloro-4-{[1-(4-difluoromethoxy-benzenesulfonyl)-2,3-dihydro-1H-indole-6-carbonyl]-amino}-benzoic acid 2-Chloro-4-{[1-(4-difluoromethoxy-benzenesulfonyl)-2,3-dihydro-1H-indole-6-carbonyl]-amino}-benzoic acid, m/z (ES+): 523.23 (M+H$^+$.), was prepared in analogy to example 1, steps 1 to 5. Step 4 was performed using 4-difluoromethoxy-benzenesulfonyl chloride and yielded 2-chloro-4-{[1-(4-difluoromethoxy-benzenesulfonyl)-2,3-dihydro-1H-indole-6-carbonyl]-amino}-benzoic acid methyl ester, which was hydrolyzed in step 5.

Example 9

4-{[1-(3-Chloro-benzenesulfonyl)-2,3-dihydro-1H-indole-6-carbonyl]-amino}-2-fluoro-benzoic acid 4-{[1-(3-Chloro-benzenesulfonyl)-2,3-dihydro-1H-indole-6-carbonyl]-amino}-2-fluoro-benzoic acid, m/z (ES+): 475.18 (M+H$^+$.), was prepared in analogy to example 1, steps 1 to 5. Step 2 was performed using 4-amino-2-fluorobenzoic acid ethyl ester and yielded 2-fluoro-4-[(1H-indole-6-carbonyl)-amino]-benzoic acid ethyl ester. This was reduced to 4-[(2,3-dihydro-1H-indole-6-carbonyl)-amino]-2-fluoro-benzoic acid ethyl ester in step 3. Step 4 was performed using 3-chloro-benzenesulfonyl chloride, yielding 4-{[1-(3-chloro-benzenesulfonyl)-2,3-dihydro-1H-indole-6-carbonyl]-amino}-2-fluoro-benzoic acid ethyl ester, which was hydrolyzed in step 5.

Preparation of 4-amino-2-fluorobenzoic acid ethyl ester:

4-Amino-2-fluorobenzoic acid ethyl ester was prepared as illustrated in scheme 14:

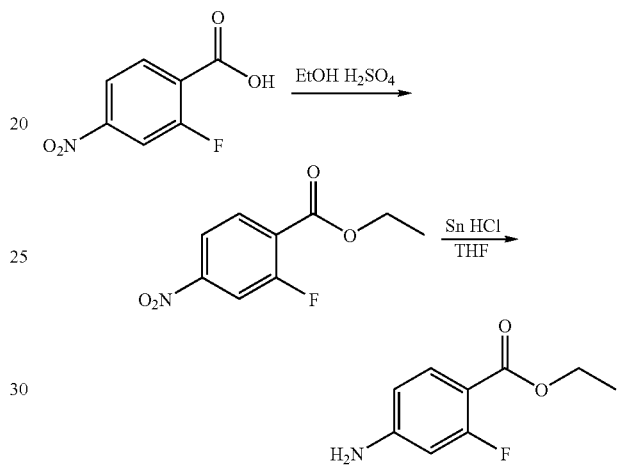

Scheme 14

Step 1:

A solution of 2-fluoro-4-nitro-benzoic acid (1.0 g, 5.4 mmol) in ethanol (10 ml) was treated with concentrated sulphuric acid (0.3 ml) and stirred at reflux overnight. Upon cooling to room temperature, a crystalline precipitate started to form. Precipitation was completed at 0° C., the solid was filtered, washing with ethanol/water 2:1, and dried under high vacuum, yielding 750 mg (65% yield) 2-fluoro-4-nitro-benzoic acid ethyl ester as a white solid. This was used as such in the following reaction.

Step 2:

A solution of 2-fluoro-4-nitro-benzoic acid ethyl ester (725 mg, 3.4 mmol) in tetrahydrofuran (11 ml) was treated with tin metal (807 mg, 6.8 mmol, 2 equiv.) and 6N HCl (5.4 ml). The mixture was warmed to 50° C. and stirred for 30 min. After cooling to room temperature, the solvent was evaporated. The residue was cooled to 0° C. and treated with 10% NaOH (20 ml). After stirring for a few minutes, the suspension was filtered, washing with water. The solid was dissolved in tetrahydrofuran and treated with Na$_2$SO$_4$. Filtration and evaporation of the solvent yielded a light yellow solid, which was purified by trituration in diisopropylether. 4-Amino-2-fluorobenzoic acid ethyl ester was obtained as a light yellow solid, 554 mg (89% yield), MS (ISP): m/e=184.1 (M+H$^+$).

Example 10

2-Fluoro-4-{[1-(3-trifluoromethyl-benzenesulfonyl)-2,3-dihydro-1H-indole-6-carbonyl]-amino}-benzoic acid 2-Fluoro-4-{[1-(3-trifluoromethyl-benzenesulfonyl)-2,3-dihydro-1H-indole-6-carbonyl]-amino}benzoic acid, m/z (ES+): 509.2 (M+H$^+$.), was prepared in analogy to example 9,

Example 11

4-{[1-(3,4-Dichloro-benzenesulfonyl)-2,3-dihydro-1H-indole-6-carbonyl]-amino}-2-fluoro-benzoic acid 4-{[1-(3,4-Dichloro-benzenesulfonyl)-2,3-dihydro-1H-indole-6-carbonyl]-amino}-2-fluoro-benzoic acid, m/z (ES+): 509.15 (M+H$^+$.), was prepared in analogy to example 9, steps 1 to 5. Step 4 was performed using 3,4-dichloro-benzenesulfonyl chloride and yielded 4-{[1-(3,4-dichloro-benzenesulfonyl)-2,3-dihydro-1H-indole-6-carbonyl]-amino}-2-fluoro-benzoic acid ethyl ester, which was hydrolyzed in step 5.

Example 12

4-{[1-(5-Chloro-2-methoxy-benzenesulfonyl)-2,3-dihydro-1H-indole-6-carbonyl]-amino}-2-fluoro-benzoic acid 4-{[1-(5-Chloro-2-methoxy-benzenesulfonyl)-2,3-dihydro-1H-indole-6-carbonyl]-amino}-2-fluoro-benzoic acid, m/z (ES+): 505.18 (M+H$^+$.), was prepared in analogy to example 9, steps 1 to 5. Step 4 was performed using 5-chloro-2-methoxy-benzenesulfonyl chloride and yielded 4-{[1-(5-chloro-2-methoxy-benzenesulfonyl)-2,3-dihydro-1H-indole-6-carbonyl]-amino}-2-fluoro-benzoic acid ethyl ester, which was hydrolyzed in step 5.

Example 13

1-(3-Chloro-benzenesulfonyl)-2,3-dihydro-1H-indole-6-carboxylic acid [4-(1H-tetrazol-5-yl)-3-trifluoromethyl-phenyl]-amide The title compound was prepared as illustrated in schemes 2, 1 and 8.

Step 1:
A 2 N trimethylaluminium solution in heptane (30.8 mmol, 15.41 mL, 3 equiv.) was added dropwise over 10 minutes to a solution of 4-amino-2-trifluoromethylbenzonitrile (30.8 mmol, 5.7 g, 3 equiv.) in dry dioxane (20 mL). The reaction mixture was stirred for a further 30 minutes then a solution of 1H-indole-6-carboxylic acid methyl ester (10.3 mmol, 1.8 g, 1 equiv.) in dioxane was added portionwise over 5 minutes and the reaction mixture was stirred at 106° C. for 16 hours. The solution was poured onto a 1M aqueous sodium tartrate solution (100 mL) and diluted with dichloromethane (50 mL). The organic layer was separated, dried over Na$_2$SO$_4$ and the solvent was removed under vacuum. The residue was dissolved in dichloromethane (10 mL) and sonicated for 5 minutes. The resultant solid was filtered to afford 1H-indole-6-carboxylic acid (4-cyano-3-trifluoromethyl-phenyl)-amide, 2.4 g (71% yield). LC @215 nm; Rt 1.50: 97%, m/z (ES+): 330 (M+H$^+$.); δ$_H$ (250 MHz; d6-DMSO) 10.89 (1H, s), 8.54 (1H, s), 8.32 (2H, m), 8.17 (1H, s), 8.13 (1H, s), 7.70 (2H, m), 7.62 (1H, t), 6.57 (1H, s).

Step 2:
Sodium cyanoborohydride (4.6 g, 73.8 mmol, 3 equiv.) was carefully added to a stirred solution of 1H-indole-6-carboxylic acid (4-cyano-3-trifluoromethyl-phenyl)-amide (2.4 g, 7.38 mmol, 1 equiv.) in acetic acid (25 mL) over 5 minutes at room temperature. The reaction mixture was stirred for 30 minutes then cooled down to 0° C. and slowly poured onto concentrated ammonium hydroxide (78 mL, d=0.880) at 0° C. The mixture was diluted with water (25 mL) and dichloromethane (25 mL), the organic layer was separated and the aqueous layer was extracted with dichloromethane (2×25 mL). The organic layers were combined, dried over Na$_2$SO$_4$ and the solvent was removed under vacuum to afford crude 2,3-dihydro-1H-indole-6-carboxylic acid (4-cyano-3-trifluoromethyl-phenyl)-amide, 1.8 g (73% yield), this material was taken onto the next step without further purification. LC @215 nm; Rt 1.13: 80%, m/z (ES+): 372 (M+H+MeCN).

Step 3:
3-Chloro-benzenesulphonyl chloride (55 mg, 0.26 mmol, 1.1 equiv.) was added to a mixture of crude 2,3-dihydro-1H-indole-6-carboxylic acid (4-cyano-3-trifluoromethyl-phenyl)-amide (70 mg, 0.24 mmol, 1 equiv.) in dichloromethane (2 ml) and pyridine (0.15 mL, 1.9 mmol, 8 equiv.) and the mixture stirred at room temperature for 16 hours. The solvent was removed under a stream of N$_2$ and the residue purified by column chromatography (SiO$_2$, dichloromethane). Fractions were combined to afford 1-(3-chloro-benzenesulfonyl)-2,3-dihydro-1H-indole-6-carboxylic acid (4-cyano-3-trifluoromethyl-phenyl)-amide, 81 mg (67% yield). LC @215 nm; Rt 1.74: 94%, m/z (ES+): 547 (M+H$^+$.), δ$_H$ (400 MHz; d6-DMSO) 11.04 (1H, s), 8.55 (1H, s), 8.36 (1H, d), 8.12-8.26 (5H, m), 7.92 (1H, t), 7.79 (1H, d), 7.45 (1H, d), 4.15 (2H, t), 3.07 (2H, t).

Step 4:
A solution of 1-(3-chloro-benzenesulfonyl)-2,3-dihydro-1H-indole-6-carboxylic acid (4-cyano-3-trifluoromethyl-phenyl)-amide (30 mg, 0.06 mmol) in dimethylformamide (0.8 ml) was treated with sodium azide (71 mg, 1.1 mmol, 18 equiv.) and ammonium chloride (58 mg, 1.1 mmol, 18 equiv.). The solution was flushed with argon, then sealed and irradiated in microwave oven at 170° C. for 1 hour. The mixture was diluted with concentrated NaHCO$_3$ and washed with ethyl acetate. The aqueous phase was acidified with HCl 1N to pH 1, then extracted twice with ethyl acetate. The combined organic phases were dried with Na$_2$SO$_4$ and the solvent evaporated to yield 15 mg (46% yield) of 1-(3-chloro-benzenesulfonyl)-2,3-dihydro-1H-indole-6-carboxylic acid [4-(1H-tetrazol-5-yl)-3-trifluoromethyl-phenyl]-amide as an orange foam, MS (ISP): m/e=547.2 (M–H), δ$_H$ (300 MHz; d6-DMSO) 10.75 (1H, s), 8.41 (1H, s), 8.21 (1H, d), 7.97 (1H, s), 7.61-7.84 (5H, m), 7.56 (1H, t), 7.32 (1H, d), 3.98 (2H, t), 2.95 (2H, t).

Example 14

2-Fluoro-4-{[4-methoxy-1-(3-trifluoromethyl-benzenesulfonyl)-2,3-dihydro-1H-indole-6-carbonyl]-amino}-benzoic acid The title compound was prepared as illustrated in schemes 3, 1 and 7.

Step 1:
Sodium cyanoborohydride (3.6 g, 57.8 mmol, 3 equiv.) was added to a stirred solution of 4-methoxy-1H-indole-6-carboxylic acid methyl ester (3.96 g, 19.3 mmol, 1 equiv.) in acetic acid (40 mL) at room temperature over 5 minutes. The mixture was stirred for 30 minutes, then cooled to 0° C. and slowly poured onto concentrated ammonium hydroxide (78 mL, d=0.880) at 0° C. The mixture was diluted with water (20 mL) extracted with dichloromethane (4×25 mL). The organic layers were combined, dried over $Na_2SO_4$ and the solvent was removed under vacuum. The crude mixture was purified by flash column chromatography ($SiO_2$, dichloromethane) and the fractions combined to afford 4-methoxy-2,3-dihydro-1H-indole-6-carboxylic acid methyl ester, 2.8 g (70% yield). LC @215 nm; Rt 0.85: 97%, m/z (ES+): 208 (M+H$^+$.); $\delta_H$ (400 MHz; d6-DMSO) 6.90 (1H, s), 6.86 (1H, s), 3.80 (3H, s), 3.79 (3H, s), 3.49 (2H, t), 2.89 (2H, t).

Step 2:

Di-tert-butyl carbonate (2.9 g, 13.5 mmol, 1 equiv.) was added to a stirred mixture of 4-methoxy-2,3-dihydro-1H-indole-6-carboxylic acid methyl ester (2.8 g 13.5 mmol, 1 equiv.) and diisopropyl ethyl amine (4.7 mL, 27 mmol, 2 equiv.) in tetrahydrofuran (30 mL) and the mixture was heated at reflux for 16 hours. The solvent was evaporated under vacuum and the residue purified by column chromatography ($SiO_2$, 1:8 EtOAc:heptane). The fractions were combined to afford 4-methoxy-2,3-dihydro-indole-1,6-dicarboxylic acid 1-tert-butyl ester 6-methyl ester, 1.96 g (47% yield). $\delta_H$ (250 MHz; d6-DMSO) 7.80 (1H, s), 7.10 (1H, s), 3.96 (2H, t), 3.78 (6H, s), 3.03 (2H, t), 1.45 (9H, m).

Step 3:

A 3 N aqueous KOH solution (6.5 mL, 19.5 mmol, 3 equiv.) was added to a solution of 4-methoxy-2,3-dihydro-indole-1,6-dicarboxylic acid 1-tert-butyl ester 6-methyl ester (2 g, 6.5 mmol, 1 equiv.) in a 1:4 MeOH:tetrahydrofuran solution (20 mL) and the mixture was shaken for 16 hours. The methanol was removed under vacuum and the pH was adjusted to 3 with 3 N aqueous HCl solution. The resulting slurry was diluted with ethyl acetate (20 mL), the organic layer was separated and the aqueous phase was extracted with EtOAc (2×20 mL). The organic layers were combined, dried over $Na_2SO_4$ and the solvent was removed under vacuum to afford 4-methoxy-2,3-dihydro-indole-1,6-dicarboxylic acid 1-tert-butyl ester, 1.68 g (88% yield). LC @215 nm; Rt 1.44: 83%, m/z (ES+): 238 (M-Boc+MeCN+H$^+$.); $\delta_H$ (400 MHz; d6-DMSO) 12.58 (1H, br.s) 7.97 (1H, br.s), 6.94 (1H, d), 3.70 (2H, t), 3.61 (3H, s), 2.75 (2H, t), 1.28 (9H, s).

Step 4:

Bromo-tris-pyrrolidino-phosphonium hexafluorophosphate (0.874 g, 1.88 mmol, 1.1 equiv.) and diisopropyl ethyl amine (0.46 mL, 3.58 mmol, 2.1 equiv.) were added to a solution of 4-methoxy-2,3-dihydro-indole-1,6-dicarboxylic acid 1-tert-butyl ester (0.500 g, 1.7 mmol, 1 equiv.) in tetrahydrofuran (10 mL) and the mixture was shaken for 5 minutes at room temperature. 4-Amino-2-fluorobenzoic acid ethyl ester (3.433 g 1.88 mmol, 1.1 equiv.) was added and the mixture shaken at room temperature for 16 hours. The solvent was removed under vacuum and the residue dissolved in trifluoroacetic acid (10 mL) and shaken for 1 hour at room temperature. The solvent was removed under vacuum and the residue was purified by column chromatography ($SiO_2$, 1:1 Hept/EtOAc to EtOAc). The fractions were combined to afford crude 2-fluoro-4-[(4-methoxy-2,3-dihydro-1H-indole-6-carbonyl)-amino]-benzoic acid ethyl ester, 0.476 g (27% yield), this material was taken onto the next step without further purification. LC @215 nm; Rt 1.17: 46%, m/z (ES+): 359 (M+H$^+$.).

Step 5:

3-Trifluoromethylbenzenesulphonyl chloride (45.1 mg, 0.18 mmol, 1.1 equiv.) was added to a mixture of crude 2-fluoro-4-[(4-methoxy-2,3-dihydro-1H-indole-6-carbonyl)-amino]-benzoic acid ethyl ester (60 mg, 0.24 mmol, 1 equiv.) and pyridine (0.11 mL, 1.34 mmol, 8 equiv.) in dichloromethane (2 mL) and the mixture was stirred at room temperature for 16 hours. The solvent was removed under a stream of $N_2$ and the residue purified by preparative HPLC to afford 2-fluoro-4-{[4-methoxy-1-(3-trifluoromethyl-benzenesulfonyl)-2,3-dihydro-1H-indole-6-carbonyl]-amino}-benzoic acid ethyl ester, 14.4 mg (33% yield). LC @215 nm; Rt 1.73: 100%, m/z (ES+): 567 (M+H$^+$.).

Step 6:

A 3 N aqueous KOH solution (2 mL) was added to a solution of 2-fluoro-4-{[4-methoxy-1-(3-trifluoromethyl-benzenesulfonyl)-2,3-dihydro-1H-indole-6-carbonyl]-amino}-benzoic acid ethyl ester (14.4 mg, 0.03 mmol, 1 equiv.) in 2:1 tetrahydrofuran:methanol (3 mL) and the mixture was shaken for 16 hours. The mixture was concentrated under a stream of $N_2$ and the pH adjusted to 1 with 3 N aqueous HCl solution (2 mL). The mixture was extracted with 1:1 $CHCl_3$:IPA (3×1 mL). The organic layers were combined, dried over $Na_2SO_4$ and the solvent was removed under reduced pressure to afford 2-fluoro-4-{[4-methoxy-1-(3-trifluoromethyl-benzenesulfonyl)-2,3-dihydro-1H-indole-6-carbonyl]-amino}-benzoic acid, 12 mg (86% yield). LC @215 nm; Rt 2.27: 98%, m/z (ES+): 539 (M+H$^+$.); $\delta_H$ (400 MHz; d6-Acetone) 10.69 (1H, br. s), 8.03 (2H, m), 7.90 (1H, d), 7.86-7.81 (3H, m), 7.82-7.72 (2H, m), 7.50 (1H, d), 7.21 (1H, s), 3.98 (2H, t), 3.74 (3H, s), 2.82 (2H, t).

Preparation of 4-methoxy-1H-indole-6-carboxylic acid methyl ester:

Methyl iodide (0.72 mL, 11.5 mmol, 1.1 equiv.) was added dropwise, over 10 minutes, to a stirred solution of 4-hydroxy-1H-indole-6-carboxylic acid methyl ester (2 g, 10.5 mmol, 1 equiv.) and potassium carbonate (1.3 g, 15.7 mmol, 1.5 equiv.) in acetone (20 mL) at room temperature and the mixture was heated at reflux for 16 hours. The solvent was removed under vacuum, the residue dissolved in ethyl acetate (20 mL) and washed with saturated aqueous solution of $NaHCO_3$ (20 mL) and water (20 mL). The organic layer was dried over $Na_2SO_4$ and the solvent removed under vacuum to afford 4-methoxy-1H-indole-6-carboxylic acid methyl ester, 1.1 g (49% yield). LC @215 nm; Rt 1.23: 91%, m/z (ES+): 206 (M+H$^+$.); $\delta_H$ (400 MHz; MeOD) 7.74 (1H, s), 7.15 (1H, m), 7.03 (1H, d), 6.46 (1H, m), 3.86 (3H, s), 3.80 (3H, s).

Example 15

4-{[1-(3-Chloro-benzenesulfonyl)-4-methoxy-2,3-dihydro-1H-indole-6-carbonyl]-amino}-2-fluoro-benzoic acid 4-{[1-(3-Chloro-benzenesulfonyl)-4-methoxy-2,3-dihydro-1H-indole-6-carbonyl]-amino}-2-fluoro-benzoic acid, m/z (ES+): 505.29 (M+H$^+$.), was prepared in analogy to example 14, steps 1 to 6. Step 5 was performed using 3-chloro-benzenesulfonyl chloride and yielded 4-{[1-(3-chloro-benzenesulfonyl)-4-methoxy-2,3-dihydro-1H-indole-6-carbonyl]-amino}-2-fluoro-benzoic acid ethyl ester, which was hydrolyzed in step 6.

Example 16

4-{[1-(3,4-Dichloro-benzenesulfonyl)-4-methoxy-2,3-dihydro-1H-indole-6-carbonyl]-amino}-2-fluoro-benzoic acid 4-{[1-(3,4-Dichloro-benzenesulfonyl)-4-methoxy-2,3-dihydro-1H-indole-6-carbonyl]-amino}-2-fluoro-benzoic acid, m/z (ES+): 539.27 (M+H⁺.), was prepared in analogy to example 14, steps 1 to 6. Step 5 was performed using 3,4-dichloro-benzenesulfonyl chloride and yielded 4-{[1-(3,4-dichloro-benzenesulfonyl)-4-methoxy-2,3-dihydro-1H-indole-6-carbonyl]-amino}-2-fluoro-benzoic acid ethyl ester, which was hydrolyzed in step 6.

Example 17

4-{[1-(5-Chloro-2-methoxy-benzenesulfonyl)-4-methoxy-2,3-dihydro-1H-indole-6-carbonyl]-amino}-2-fluoro-benzoic acid 4-{[1-(5-Chloro-2-methoxy-benzenesulfonyl)-4-methoxy-2,3-dihydro-1H-indole-6-carbonyl]-amino}-2-fluoro-benzoic acid, m/z (ES+): 535.33 (M+H⁺.), was prepared in analogy to example 14, steps 1 to 6. Step 5 was performed using 5-chloro-2-methoxy-benzenesulfonyl chloride and yielded 4-{[1-(5-chloro-2-methoxy-benzenesulfonyl)-4-methoxy-2,3-dihydro-1H-indole-6-carbonyl]-amino}-2-fluoro-benzoic acid ethyl ester, which was hydrolyzed in step 6.

Example 18

4-{[1-(3,5-Dichloro-benzenesulfonyl)-4-methoxy-2,3-dihydro-1H-indole-6-carbonyl]-amino}-2-fluoro-benzoic acid 4-{[1-(3,5-Dichloro-benzenesulfonyl)-4-methoxy-2,3-dihydro-1H-indole-6-carbonyl]-amino}-2-fluoro-benzoic acid, m/z (ES+): 539.26 (M+H⁺.), was prepared in analogy to example 14, steps 1 to 6. Step 5 was performed using 3,5-dichloro-benzenesulfonyl chloride and yielded 4-{[1-(3,5-dichloro-benzenesulfonyl)-4-methoxy-2,3-dihydro-1H-indole-6-carbonyl]-amino}-2-fluoro-benzoic acid ethyl ester, which was hydrolyzed in step 6.

Example 19

2-Fluoro-4-{[1-(3-fluoro-benzenesulfonyl)-4-methoxy-2,3-dihydro-1H-indole-6-carbonyl]-amino}-benzoic acid 2-Fluoro-4-{[1-(3-fluoro-benzenesulfonyl)-4-methoxy-2,3-dihydro-1H-indole-6-carbonyl]-amino}-benzoic acid, m/z (ES+): 489.08 (M+H⁺.), was prepared in analogy to example 14, steps 1 to 6. Step 5 was performed using 3-fluoro-benzenesulfonyl chloride and yielded 2-fluoro-4-{[1-(3-fluoro-benzenesulfonyl)-4-methoxy-2,3-dihydro-1H-indole-6-carbonyl]-amino}-benzoic acid ethyl ester, which was hydrolyzed in step 6.

Example 20

2-Fluoro-4-{[4-methoxy-1-(2-methoxy-5-methyl-benzenesulfonyl)-2,3-dihydro-1H-indole-6-carbonyl]-amino}-benzoic acid 2-Fluoro-4-{[4-methoxy-1-(2-methoxy-5-methyl-benzenesulfonyl)-2,3-dihydro-1H-indole-6-carbonyl]-amino}-benzoic acid, m/z (ES+): 515.37 (M+H⁺.), was prepared in analogy to example 14, steps 1 to 6. Step 5 was performed using 2-methoxy-5-methyl-benzenesulfonyl chloride and yielded 2-fluoro-4-{[4-methoxy-1-(2-methoxy-5-methyl-benzenesulfonyl)-2,3-dihydro-1H-indole-6-carbonyl]-amino}-benzoic acid ethyl ester, which was hydrolyzed in step 6.

Example 21

2-Chloro-4-{[4-methoxy-1-(3-trifluoromethyl-benzenesulfonyl)-2,3-dihydro-1H-indole-6-carbonyl]-amino}-benzoic acid 2-Chloro-4-{[4-methoxy-1-(3-trifluoromethyl-benzenesulfonyl)-2,3-dihydro-1H-indole-6-carbonyl]-amino}-benzoic acid, m/z (ES+): 555.3 (M+H⁺.), was prepared in analogy to example 14, steps 1 to 6. Step 4 was performed using 4-amino-2-chlorobenzoic acid methyl ester, yielding 2-chloro-4-[(4-methoxy-2,3-dihydro-1H-indole-6-carbonyl)-amino]-benzoic acid methyl ester. This was reacted with 3-trifluoromethyl-benzenesulfonyl chloride in step 5, yielding 2-chloro-4-{[4-methoxy-1-(3-trifluoromethyl-benzenesulfonyl)-2,3-dihydro-1H-indole-6-carbonyl]-amino}-benzoic acid methyl ester, which was hydrolyzed in step 6.

Example 22

2-Chloro-4-{[1-(5-chloro-2-methoxy-benzenesulfonyl)-4-methoxy-2,3-dihydro-1H-indole-6-carbonyl]-amino}-benzoic acid 2-Chloro-4-{[1-(5-chloro-2-methoxy-benzenesulfonyl)-4-methoxy-2,3-dihydro-1H-indole-6-carbonyl]-amino}-benzoic acid, m/z (ES+): 551.28 (M+H⁺.), was prepared in analogy to example 21, steps 1 to 6. Step 5 was performed using 5-chloro-2-methoxy-benzenesulfonyl chloride, yielding 2-chloro-4-{[1-(5-chloro-2-methoxy-benzenesulfonyl)-4-methoxy-2,3-dihydro-1H-indole-6-carbonyl]-amino}-benzoic acid methyl ester, which was hydrolyzed in step 6.

Example 23

2-Chloro-4-{[1-(3,5-dichloro-benzenesulfonyl)-4-methoxy-2,3-dihydro-1H-indole-6-carbonyl]-amino}-benzoic acid 2-Chloro-4-{[1-(3,5-dichloro-benzenesulfonyl)-4-methoxy-2,3-dihydro-1H-indole-6-carbonyl]-amino}-benzoic acid, m/z (ES+): 555.25 (M+H⁺.), was prepared in analogy to example 21, steps 1 to 6. Step 5 was performed using 3,5-dichloro-benzenesulfonyl chloride, yielding 2-chloro-4-{[1-(3,5-dichloro-benzenesulfonyl)-4-methoxy-2,3-dihydro-1H-indole-6-carbonyl]-amino}-benzoic acid methyl ester, which was hydrolyzed in step 6.

Example 24

2-Chloro-4-{[1-(3-fluoro-benzenesulfonyl)-4-methoxy-2,3-dihydro-1H-indole-6-carbonyl]-amino}-benzoic acid 2-Chloro-4-{[1-(3-fluoro-benzenesulfonyl)-4-methoxy-2,3-dihydro-1H-indole-6-carbonyl]-amino}-benzoic acid, m/z (ES+): 505.29 (M+H⁺.), was prepared in analogy to example 21, steps 1 to 6. Step 5 was performed using 3-fluoro-benzenesulfonyl chloride, yielding 2-chloro-4-{[1-(3-fluoro-benzenesulfonyl)-4-methoxy-2,3-dihydro-1H-indole-6-carbonyl]-amino}-benzoic acid methyl ester, which was hydrolyzed in step 6.

Example 25

2-Chloro-4-{[1-(3-chloro-benzenesulfonyl)-4-methoxy-2,3-dihydro-1H-indole-6-carbonyl]-amino}-benzoic acid 2-Chloro-4-{[1-(3-chloro-benzenesulfonyl)-4-methoxy-2,3-dihydro-1H-indole-6-carbonyl]-amino}-benzoic acid, m/z (ES+): 521.1 (M+H$^+$.), was prepared in analogy to example 21, steps 1 to 6. Step 5 was performed using 3-chloro-benzenesulfonyl chloride, yielding 2-chloro-4-{[1-(3-chloro-benzenesulfonyl)-4-methoxy-2,3-dihydro-1H-indole-6-carbonyl]-amino}-benzoic acid methyl ester, which was hydrolyzed in step 6.

Example 26

4-{[1-(3-Chloro-benzenesulfonyl)-4-methoxy-2,3-dihydro-1H-indole-6-carbonyl]-amino}-benzoic acid 4-{[1-(3-Chloro-benzenesulfonyl)-4-methoxy-2,3-dihydro-1H-indole-6-carbonyl]-amino}-benzoic acid, m/z (ES+): 487.29 (M+H$^+$.), was prepared in analogy to example 14, steps 1 to 6. Step 4 was performed using 4-amino-benzoic acid ethyl ester, yielding 4-[(4-methoxy-2,3-dihydro-1H-indole-6-carbonyl)-amino]-benzoic acid ethyl ester. This was reacted with 3-chloro-benzenesulfonyl chloride in step 5, yielding 4-{[1-(3-chloro-benzenesulfonyl)-4-methoxy-2,3-dihydro-1H-indole-6-carbonyl]-amino}-benzoic acid ethyl ester, which was hydrolyzed in step 6.

Example 27

4-{[1-(5-Chloro-2-methoxy-benzenesulfonyl)-4-methoxy-2,3-dihydro-1H-indole-6-carbonyl]-amino}-benzoic acid 4-{[1-(5-Chloro-2-methoxy-benzenesulfonyl)-4-methoxy-2,3-dihydro-1H-indole-6-carbonyl]-amino}benzoic acid, m/z (ES+): 517.32 (M+H$^+$.), was prepared in analogy to example 26, steps 1 to 6. Step 5 was performed using 5-chloro-2-methoxy-benzenesulfonyl chloride, yielding 4-{[1-(5-chloro-2-methoxy-benzenesulfonyl)-4-methoxy-2,3-dihydro-1H-indole-6-carbonyl]-amino}-benzoic acid ethyl ester, which was hydrolyzed in step 6.

Example 28

4-{[4-Methoxy-1-(2-methoxy-5-methyl-benzenesulfonyl)-2,3-dihydro-1H-indole-6-carbonyl]-amino}-benzoic acid 4-{[4-Methoxy-1-(2-methoxy-5-methyl-benzenesulfonyl)-2,3-dihydro-1H-indole-6-carbonyl]-amino}-benzoic acid, m/z (ES+): 497.35 (M+H$^+$.), was prepared in analogy to example 26, steps 1 to 6. Step 5 was performed using 2-methoxy-5-methyl-benzenesulfonyl chloride, yielding 4-{[4-methoxy-1-(2-methoxy-5-methyl-benzenesulfonyl)-2,3-dihydro-1H-indole-6-carbonyl]-amino}-benzoic acid ethyl ester, which was hydrolyzed in step 6.

Example 29

4-{[1-(3-Fluoro-benzenesulfonyl)-4-methoxy-2,3-dihydro-1H-indole-6-carbonyl]-amino}-benzoic acid 4-{[1-(3-Fluoro-benzenesulfonyl)-4-methoxy-2,3-dihydro-1H-indole-6-carbonyl]-amino}-benzoic acid, m/z (ES+): 471.15 (M+H$^+$.), was prepared in analogy to example 26, steps 1 to 6. Step 5 was performed using 3-fluoro-benzenesulfonyl chloride, yielding 4-{[1-(3-fluoro-benzenesulfonyl)-4-methoxy-2,3-dihydro-1H-indole-6-carbonyl]-amino}-benzoic acid ethyl ester, which was hydrolyzed in step 6.

Example 30

4-{[1-(3,5-Dichloro-benzenesulfonyl)-2,3-dihydro-1H-indole-6-carbonyl]-amino}-benzoic acid 4-{[1-(3,5-Dichloro-benzenesulfonyl)-2,3-dihydro-1H-indole-6-carbonyl]-amino}-benzoic acid, MS (ISP): m/e=488.9 (M−H), was prepared in analogy to example 14, steps 1 to 6. Step 1 was performed starting from 1H-indole-6-carboxylic acid methyl ester, which was reduced to 2,3-dihydro-1H-indole-6-carboxylic acid methyl ester (see also example 34). This was protected in step 2 to 2,3-dihydro-indole-1,6-dicarboxylic acid 1-tert-butyl ester 6-methyl ester, which was then hydrolyzed to 2,3-dihydro-indole-1,6-dicarboxylic acid 1-tert-butyl ester in step 3. Step 4 was performed using 4-amino-benzoic acid ethyl ester, yielding 4-[(2,3-dihydro-1H-indole-6-carbonyl)-amino]-benzoic acid ethyl ester. This was reacted with 3,5-dichloro-benzenesulfonyl chloride in step 5, yielding 4-{[1-(3,5-dichloro-benzenesulfonyl)-2,3-dihydro-1H-indole-6-carbonyl]-amino}-benzoic acid, which was hydrolyzed in step 6.

Example 31

4-{[1-(5-Chloro-2-methoxy-benzenesulfonyl)-2,3-dihydro-1H-indole-6-carbonyl]-amino}-benzoic acid 4-{[1-(5-Chloro-2-methoxy-benzenesulfonyl)-2,3-dihydro-1H-indole-6-carbonyl]-amino}-benzoic acid, MS (ISP): m/e=485.2 (M−H), was prepared in analogy to example 30, steps 1 to 6. Step 5 was performed using 5-chloro-2-methoxy-benzenesulfonyl chloride, yielding 4-{[1-(5-chloro-2-methoxy-benzenesulfonyl)-2,3-dihydro-1H-indole-6-carbonyl]-amino}-benzoic acid ethyl ester, which was hydrolyzed in step 6.

Example 32

4-{[1-(3-Trifluoromethoxy-benzenesulfonyl)-2,3-dihydro-1H-indole-6-carbonyl]-amino}-benzoic acid 4-{[1-(3-Trifluoromethoxy-benzenesulfonyl)-2,3-dihydro-1H-indole-6-carbonyl]-amino}-benzoic acid, MS (ISP): m/e=505.1 (M−H), was prepared in analogy to example 30, steps 1 to 6. Step 5 was performed using 3-trifluoromethoxy-benzenesulfonyl chloride, yielding 4-{[1-(3-trifluoromethoxy-benzenesulfonyl)-2,3-dihydro-1H-indole-6-carbonyl]-amino}-benzoic acid ethyl ester, which was hydrolyzed in step 6.

Example 33

4-{[1-(3-Fluoro-benzenesulfonyl)-2,3-dihydro-1H-indole-6-carbonyl]-amino}-benzoic acid 4-{[1-(3-Fluoro-benzenesulfonyl)-2,3-dihydro-1H-indole-6-carbonyl]-amino}-benzoic acid, MS (ISP): m/e=439.3 (M−H), was prepared in analogy to example 30, steps 1 to 6. Step 5 was performed using 3-fluoro-benzenesulfonyl chloride, yielding 4-{[1-(3-fluoro-benzenesulfonyl)-2,3-dihydro-1H-indole-6-carbonyl]-amino}-benzoic acid ethyl ester, which was hydrolyzed in step 6.

Example 34

1-(5-Chloro-2-methoxy-benzenesulfonyl)-2,3-dihydro-1H-indole-6-carboxylic acid (4-chloro-phenyl)-amide The title compound was prepared as illustrated in scheme 4.

Step 1:

A solution of indole-6-carboxylic acid methyl ester (534 mg, 3.05 mmol) in acetic acid (7.5 ml) was cooled to 0° C. Sodium cyanoborohydride (580 mg, 9.2 mmol, 3 equiv.) was added and the mixture stirred at 15° C. for 40 min. A further aliquot of sodium cyanoborohydride (193 mg, 3.05 mmol, 1 equiv.) was added, and the reaction mixture was stirred for 30 min. at room temperature. The solvent was then evaporated, and the residue dissolved in dichloromethane and washed with 1N NaOH. The organic phase was dried with $Na_2SO_4$ and evaporated, yielding 2,3-dihydro-1H-indole-6-carboxylic acid methyl ester as a light yellow solid, 494 mg (77%). This was used as such in the following reaction.

Step 2:

A solution of 2,3-dihydro-1H-indole-6-carboxylic acid methyl ester (1.34 g, 7.6 mmol) in dichloromethane (66 ml) and pyridine (1.6 ml) was treated with 5-chloro-2-methoxy-benzenesulfonyl chloride (1.83 g, 7.6 mmol, 1 equiv.). The mixture was stirred at room temperature overnight, then diluted with dichloromethane and washed with water. The organic phase was dried with $Na_2SO_4$ and evaporated. The residue was purified by flash chromatography (heptane/ethyl acetate gradient), yielding 1-(5-chloro-2-methoxy-benzenesulfonyl)-2,3-dihydro-1H-indole-6-carboxylic acid methyl ester, 2.2 g (77% yield). MS (ISP): m/e=382.1 (M+H$^+$.), $\delta_H$ (300 MHz; CDCl$_3$) 7.99 (1H, d), 7.93 (1H, s), 7.61 (1H, d), 7.37 (1H, dd), 7.11 (1H, d), 6.77 (1H, d), 4.04 (2H, t), 3.83 (3H, s), 3.56 (3H, s), 3.02 (2H, t).

Step 3:

A suspension of 1-(5-chloro-2-methoxy-benzenesulfonyl)-2,3-dihydro-1H-indole-6-carboxylic acid methyl ester (2.2 g, 5.8 mmol) in methanol (6 ml) and tetrahydrofuran (6 ml) was treated with 3N KOH (6 ml, 3 equiv.) and stirred at room temperature for 24 hours. The organic solvents were evaporated and the aqueous slurry treated with HCl 3N so as to reach pH 3. The white precipitate was filtered washing with methanol and water and dried under high vacuum to yield 1-(5-chloro-2-methoxy-benzenesulfonyl)-2,3-dihydro-1H-indole-6-carboxylic acid as an off-white solid, 1.9 g (88%). This was used as such in the following reaction.

Step 4:

A solution of 1-(5-chloro-2-methoxy-benzenesulfonyl)-2,3-dihydro-1H-indole-6-carboxylic acid (30 mg, 0.082 mmol) in acetone (0.9 ml) was treated with N-methylmorpholine (0.025 ml, 2.4 equiv.) and cyanuric chloride (18 mg, 0.098 mmol, 1.2 equiv.) and stirred at room temperature for 2 hours. 4-Chloro-phenyl-amine (12 mg, 0.098 mol, 1.2 equiv.) was then added, and the mixture was stirred for 12 hours at room temperature. The solvent was evaporated, and the residue dissolved in methanol (2.5 ml) and purified by preparative HPLC (ZORBAX Eclipse XDB-C18, 21.2×50 mm, 5 μm, gradient acetonitrile/water+0.1% formic acid). 1-(5-Chloro-2-methoxy-benzenesulfonyl)-2,3-dihydro-1H-indole-6-carboxylic acid (4-chloro-phenyl)-amide was obtained as a white solid, 10.6 mg (27%). MS (ISP): m/e=474.9, 477.8 (M−H), $\delta_H$ (300 MHz; d6-DMSO) 10.33 (1H, s), 7.86 (1H, d), 7.79 (2H, d), 7.71 (1H, s), 7.69 (1H, d), 7.60 (1H, d), 7.40 (2H, d), 7.35 (1H, d), 7.21 (1H, d), 4.10 (2H, t), 3.66 (3H, s), 3.12 (2H, t).

Example 35

1-(5-Chloro-2-methoxy-benzenesulfonyl)-2,3-dihydro-1H-indole-6-carboxylic acid phenylamide 1-(5-Chloro-2-methoxy-benzenesulfonyl)-2,3-dihydro-1H-indole-6-carboxylic acid phenylamide, MS (ISP): m/e=441.0 (M−H), was prepared in analogy to example 34, steps 1 to 4. Step 4 was performed using aniline.

Example 36

4-[(1-Benzenesulfonyl-2,3-dihydro-1H-indole-6-carbonyl)-amino]-benzoic acid

4-[(1-Benzenesulfonyl-2,3-dihydro-1H-indole-6-carbonyl)-amino]-benzoic acid, MS (ISP), m/e=421.1 (M−H), was prepared in analogy to example 34, steps 1 to 4. Step 2 was performed using benzenesulfonyl chloride, yielding 1-benzenesulfonyl-2,3-dihydro-1H-indole-6-carboxylic acid methyl ester, which was hydrolyzed to 1-benzenesulfonyl-2,3-dihydro-1H-indole-6-carboxylic acid in step 3.

Step 4 was performed as follows:

Benzenesulfonyl-2,3-dihydro-1H-indole-6-carboxylic acid (40 mg, 0.13 mmol) was added to a solution of thionyl chloride (63 mg, 0.53 mmol, 4 equiv.) in dichloromethane (5 ml) and DMF (1 ml). The reaction mixture was stirred for 2 hours, then the solvent was removed. The crude acyl chloride was redissolved in dichloromethane (5 ml) and treated with 4-amino benzoic acid methyl ester (80 mg, 0.53 mmol, 4 equiv.). The mixture was stirred for 30 min. at room temperature, then the solvent was removed. The residue was purified by flash chromatography, yielding 4-[(1-benzenesulfonyl-2,3-dihydro-1H-indole-6-carbonyl)-amino]-benzoic acid methyl ester as a white solid, 42 mg (73%). MS (ISP): m/e=437.3 (M+H$^+$.), $\delta_H$ (300 MHz; CDCl$_3$) 8.02-8.09 (4H, m), 7.82 (2H, d), 7.77 (2H, d), 7.45-7.61 (4H, m), 7.21 (2H, d), 3.98 (2H, t), 3.92 (3H, s), 2.97 (2H, t).

4-[(1-benzenesulfonyl-2,3-dihydro-1H-indole-6-carbonyl)-amino]-benzoic acid methyl ester was then hydrolyzed to 4-[(1-benzenesulfonyl-2,3-dihydro-1H-indole-6-carbonyl)-amino]-benzoic acid in step 5, in analogy to example 14.

Example 37

1-(5-Chloro-2-methoxy-benzenesulfonyl)-2,3-dihydro-1H-indole-6-carboxylic acid [4-(1H-tetrazol-5-yl)-phenyl]-amide 1-(5-Chloro-2-methoxy-benzenesulfonyl)-2,3-dihydro-1H-indole-6-carboxylic acid [4-(1H-tetrazol-5-yl)-phenyl]-amide, MS (ISP), m/e=509.1 (M−H), was prepared in analogy to example 13, steps 1 to 4. Step 1 was performed using 4-amino-benzonitrile and yielded 1H-indole-6-carboxylic acid (4-cyano-phenyl)-amide which was reduced to 2,3-dihydro-1H-indole-6-carboxylic acid (4-cyano-phenyl)-amide in step 2. This was coupled with 5-chloro-2-methoxy benzenesulfonyl chloride in step 3, yielding 1-(5-chloro-2-methoxy-benzenesulfonyl)-2,3-dihydro-1H-indole-6-carboxylic acid (4-cyano-phenyl)-amide, which was converted to 1-(5-chloro-2-methoxy-benzenesulfonyl)-2,3-dihydro-1H-indole-6-carboxylic acid [4-(1H-tetrazol-5-yl)-phenyl]-amide by reaction with ammonium azide in step 4.

Example 38

1-(5-Chloro-2-methoxy-benzenesulfonyl)-2,3-dihydro-1H-indole-6-carboxylic acid [4-(5-oxo-4,5-dihydro-[1,2,4]oxadiazol-3-yl)-phenyl]-amide 1-(5-Chloro-2-methoxy-benzenesulfonyl)-2,3-dihydro-1H-indole-6-carboxylic acid [4-(5-oxo-4,5-dihydro-[1,2,4]oxadiazol-3-yl)-phenyl]-amide was prepared as illustrated in scheme 9.

Step 1:

A solution of hydroxylamine hydrochloride (223 mg, 3.21 mmol, 5 equiv.) in dimethyl sulfoxide (3 ml) was treated with triethylamine (0.45 ml, 3.21 mmol, 5 equiv.) and stirred at room temperature for 5 min. The white precipitate was filtered off and to the filtrate, 1-(5-chloro-2-methoxy-benzenesulfonyl)-2,3-dihydro-1H-indole-6-carboxylic acid (4-cyano-phenyl)-amide (300 mg, 0.64 mmol, 1 equiv.) (prepared as illustrated in example 37, steps 1 to 3) was added. The mixture was stirred at 75° C. for 1 hour and 15 min. The reaction mixture was then cooled to room temperature, diluted with water and extracted with ethyl acetate. The organic phase was extracted three times with 0.5 N HCl. The combined aqueous phase was adjusted to pH 9-10 with NaOH 1N and extracted three times with ethyl acetate. The combined organic phases were dried with $Na_2SO_4$ and the solvent was evaporated. Crude 1-(5-chloro-2-methoxy-benzenesulfonyl)-2,3-dihydro-1H-indole-6-carboxylic acid [4-(N-hydroxycarbamimidoyl)-phenyl]-amide was obtained as a white solid, 261 mg (81%), which was used as such in the following reaction. MS (ISP): m/e=501.3 (M+H$^+$.), $\delta_H$ (300 MHz; d6-DMSO) 10.25 (1H, s), 9.50 (1H, s), 7.80 (1H, s), 7.55-7.71 (7H, m), 7.28 (1H, d), 7.16 (1H, d), 5.69 (2H, s), 4.04 (2H, t), 3.60 (3H, s), 3.06 (2H, t).

Step 2:

A solution of 1-(5-chloro-2-methoxy-benzenesulfonyl)-2,3-dihydro-1H-indole-6-carboxylic acid [4-(N-hydroxycarbamimidoyl)-phenyl]-amide (254 mg, 0.51 mmol) in dimethylformamide (3.5 ml) was treated with pyridine (0.04 ml, 1 equiv.) and the mixture was cooled to 0° C. Chloroformic acid 2-ethylhexyl ester (98 mg, 0.51 mmol, 1 equiv.) was added dropwise. The reaction mixture was stirred at 0° C. for 30 min, then quenched with water. The slurry was extracted three times with ethyl acetate. The combined organic layers were dried with $Na_2SO_4$ and the solvent was evaporated. The crude compound was suspended in xylene and heated at reflux for 2 hours. After cooling to room temperature, the solid was filtered and dried under high vacuum, yielding 1-(5-chloro-2-methoxy-benzenesulfonyl)-2,3-dihydro-1H-indole-6-carboxylic acid [4-(5-oxo-4,5-dihydro-[1,2,4]oxadiazol-3-yl)-phenyl]-amide as a white solid, 114 mg (43%). MS (ISP): m/e=525.2 (M−H), $\delta_H$ (300 MHz; d6-DMSO) 10.31 (1H, s), 7.55-7.80 (8H, m), 7.28 (1H, d), 7.16 (1H, d), 4.04 (2H, t), 3.60 (3H, s), 3.06 (2H, t).

Example 39

1-(5-Chloro-2-methoxy-benzenesulfonyl)-2,3-dihydro-1H-indole-6-carboxylic acid [4-(2,2,2-trifluoro-1-hydroxy-ethyl)-phenyl]-amide 1-(5-Chloro-2-methoxy-benzenesulfonyl)-2,3-dihydro-1H-indole-6-carboxylic acid [4-(2,2,2-trifluoro-1-hydroxy-ethyl)-phenyl]-amide, MS (ISP), m/e=539.0 (M−H), was prepared in analogy to example 34, steps 1 to 4. Step 4 was performed using 1-(4-amino-phenyl)-2,2,2-trifluoro-ethanol.

1-(4-Amino-phenyl)-2,2,2-trifluoro-ethanol was prepared as illustrated in scheme 15.

Scheme 15

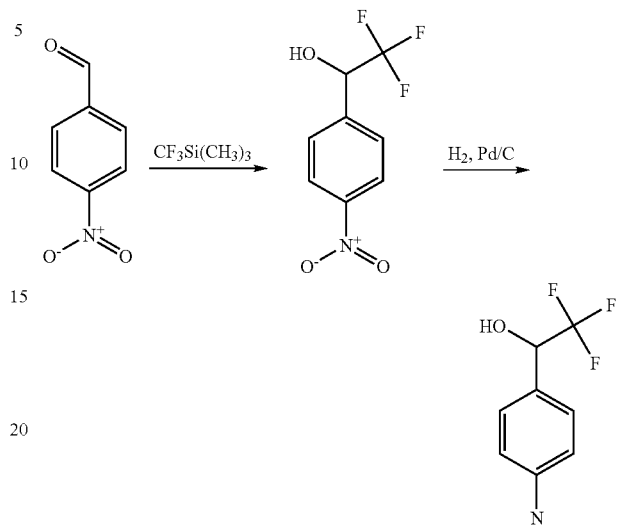

Step 1:

A solution of 4-nitro-benzaldehyde (2.5 g, 17 mmol) in tetrahydrofuran (35 ml) was treated with trimethyl-trifluoromethyl-silane (2N in tetrahydrofuran, 10 ml, 20 mmol, 1.2 equiv.) and cooled to 0° C. A solution of tetrabutylammonium fluoride (1N in tetrahydrofuran, 1.70 ml, 2 mmol) was added, upon which the solution turned bright orange and then black. The mixture was stirred at 0° C. for 10 min, then at room temperature for 1 hour. The mixture was quenched with HCl 3N (6 ml), and stirred at room temperature overnight. The reaction was then diluted with ethyl acetate and brine and the two phases separated. The organic phase was washed with water, dried with $Na_2SO_4$ and the solvent was evaporated. The residue was purified by flash chromatography (heptane/ethyl acetate gradient), yielding 2,2,2-trifluoro-1-(4-nitro-phenyl)-ethanol as a yellow solid, 2.1 g (57%). MS (ISP): m/e=220.1 (M−H), $\delta_H$ (300 MHz; CDCl$_3$) 8.28 (2H, d), 7.70 (2H, d), 5.19 (1H, m), 2.84 (1H, d).

Step 2:

A solution of 2,2,2-trifluoro-1-(4-nitro-phenyl)-ethanol (2.0 g, 9 mmol) in ethanol (100 ml) and tetrahydrofuran (37 ml) was treated under argon with Pd/C (250 mg) and hydrazine hydrate (80% in water, 6.15 ml, 127 mmol, 14 equiv.) The mixture was stirred at room temperature for 30 min, then the black solid was filtered and the solvent evaporated. 1-(4-Amino-phenyl)-2,2,2-trifluoro-ethanol was obtained as a light yellow deliquescent solid, 1.8 g (100%). $\delta_H$ (300 MHz; CDCl$_3$) 7.24 (2H, d), 6.67 (2H, d), 4.87 (1H, m), 3.72 (2H, bs), 3.32 (1H, bs).

Example 40

Chloro-4-{[1-(3-fluoro-benzenesulfonyl)-1,2,3,4-tetrahydro-quinoline-7-carbonyl]-amino}-benzoic acid Chloro-4-{[1-(3-fluoro-benzenesulfonyl)-1,2,3,4-tetrahydro-quinoline-7-carbonyl]-amino}-benzoic acid was prepared as illustrated in schemes 5 and 7.

Step 1:

Lithium hydroxide monohydrate (5.42 g, 141 mmol, 3 equiv.) in water (50 ml) was added to a solution of quinoline-7-carboxylic acid methyl ester (8.8 g, 47 mmol) in tetrahydrofuran (200 ml) and the solution was stirred at room temperature for 16 hours. The tetrahydrofuran was evaporated under reduced pressure and the solution adjusted to pH 7 with 1N HCl (aq) (141 ml), forming a white precipitate. The precipitate was filtered and washed with water and heptane. The solid was dried in a vacuum oven at 50° C. to give quinoline-7-carboxylic acid, 8.4 g (100% yield) as a white solid. LC @215 nm; Rt 0.66: 100%, m/z (ES$^+$): 174 (M+H$^+$.); $\delta_H$ (400 MHz; d6-DMSO) 9.02 (1H, dd), 8.58 (1H, s), 8.48 (1H, d), 8.09 (2H, m), 7.66 (1H, dd).

Step 2:

Bromo-tris-pyrrolidino-phosphonium hexafluorophosphate (6.03 g, 12.9 mmol, 1.1 equiv.) and diisopropyl ethyl amine (3.19 g, 12.9 mmol, 1.1 equiv.) were added to a solution of quinoline-7-carboxylic acid (2.03 g, 11.75 mmol) in tetrahydrofuran (100 ml) and the resultant mixture stirred for 10 minutes. 4-Amino-2-chlorobenzoic acid methyl ester (2.40 g, 12.9 mmol, 1.1 equiv.) in tetrahydrofuran (20 ml) was added and the mixture refluxed for 16 hours. Additional Bromo-tris-pyrrolidino-phosphonium hexafluorophosphate (1.10 g, 2.36 mmol, 0.2 equiv.) and diisopropyl ethyl amine (0.61 g, 4.7 mmol, 0.4 equiv.) were added and the mixture refluxed for a further 16 hours. The mixture was evaporated then dissolved in isopropanol (100 ml). Water (5 ml) and 60% aqueous perchloric acid (0.5 ml) were added and the mixture was refluxed for 24 hours. The mixture was filtered while hot then left to cool to room temperature whereupon a crystalline solid was formed. The solid was filtered and washed with cold isopropanol (20 ml) and dichloromethane (20 ml) to give 2-chloro-4-[(quinoline-7-carbonyl)-amino]-benzoic acid methyl ester, 1.42 g (35% yield), as a tan solid. LC @215 nm; Rt 1.11: 100%, m/z (ES$^+$): 341 (M+H$^+$.); $\delta_H$ (400 MHz; d6-DMSO) 10.96 (1H, br.s), 9.05 (1H, m), 8.73 (1H, s), 8.49 (1H, d), 8.18-8.10 (3H, m), 7.94 (2H, s), 7.68 (1H, dd), 3.86 (3H, s).

Step 3:

Water (1.5 ml), 60% aqueous perchloric acid (0.01 ml) and pentamethylcyclopentadienyliridium(III) chloride dimer) (116 mg, 0.145 mmol, 0.05 equiv.) were added to 2-chloro-4-[(quinoline-7-carbonyl)-amino]-benzoic acid methyl ester (1.42 g, 4.17 mmol) in degassed isopropanol (100 ml) under a nitrogen atmosphere and the mixture was refluxed for 48 hours. The mixture was evaporated to give a tan solid. The solid was purified by flash chromatography (SiO$_2$, 1:9 tert-butyl-methyl ether:dichloromethane to 1:1:8 tert-butyl-methyl ether:methanol:dichloromethane). The fractions were combined to afford 2-chloro-4-[(1,2,3,4-tetrahydro-quinoline-7-carbonyl)-amino]-benzoic acid methyl ester, 0.434 g (30% yield) as a tan solid. LC @215 nm; Rt 1.15: 98%, m/z (ES$^+$): 345 (M+H$^+$.); $\delta_H$ (250 MHz; d6-DMSO) 10.39 (1H, br.s), 8.07 (1H, m), 7.91-7.80 (2H, m), 7.05-6.90 (3H, m), 5.95 (1H, br.s), 3.82 (3H, s), 3.19 (2H, m), 2.70 (2H, m), 1.79 (2H, m).

Step 4:

3-Fluorobenzenesulphonyl chloride (0.027 g, 0.137 mmol, 1.05 equiv.) was added to a mixture of 2-chloro-4-[(1,2,3,4-tetrahydro-quinoline-7-carbonyl)-amino]-benzoic acid methyl ester (0.045 g, 0.130 mmol) and pyridine (0.1 ml) in dichloromethane (2 ml) and the mixture shaken for 16 hours. The solution was washed with saturated sodium hydrogen carbonate (2 ml) and 1M aqueous HCl (2 ml) then dried over magnesium sulphate. The solution was evaporated to afford the crude 2-chloro-4-{[1-(3-fluoro-benzenesulfonyl)-1,2,3,4-tetrahydro-quinoline-7-carbonyl]-amino}-benzoic acid methyl ester, 0.097 g, as a red oil. This material was taken onto the next step without further purification. LC @215 nm; Rt 1.64: 100%, m/z (ES$^+$): 502 (M+H).

Step 5:

3 M Potassium hydroxide solution (2 ml) was added to a solution of crude 2-chloro-4-{[1-(3-fluoro-benzenesulfonyl)-1,2,3,4-tetrahydro-quinoline-7-carbonyl]-amino}-benzoic acid methyl ester (0.097 g, 0.13 mmol) in MeOH (2 ml) and tetrahydrofuran (1 ml) and the mixture stirred for 16 hours. The organic solvent was evaporated and the solution neutralized with 3 M HCl solution (3 ml) forming a white precipitate. The precipitate was filtered and washed with heptane. The solid was then dried under vacuum to give 2-chloro-4-{[1-(3-fluoro-benzenesulfonyl)-1,2,3,4-tetrahydro-quinoline-7-carbonyl]-amino}-benzoic acid, 0.037 g, as a red solid. LC @215 nm; Rt 2.06: 98%, m/z (ES$^+$): 489.23 (M+H$^+$.); $\delta_H$ (400 MHz; d6-DMSO) 13.18 (1H, br.s), 10.63 (1H, s), 8.22 (1H, d), 8.08 (1H, d), 7.83-7.91 (2H, m), 7.76 (1H, dd), 7.55-7.67 (2H, m), 7.43-7.48 (2H, m), 7.30 (1H, d), 3.84 (2H, m), 2.52 (2H, m), 1.62 (2H, m).

Example 41

2-Chloro-4-{[1-(3,4-dichloro-benzenesulfonyl)-1,2,3,4-tetrahydro-quinoline-7-carbonyl]-amino}-benzoic acid 2-Chloro-4-{[1-(3,4-dichloro-benzenesulfonyl)-1,2,3,4-tetrahydro-quinoline-7-carbonyl]-amino}-benzoic acid, m/z (ES+): 539.18 (M+H$^+$.), was prepared in analogy to example 40, steps 1 to 5. Step 4 was performed using 3,4-dichloro-benzenesulfonyl chloride, yielding 2-chloro-4-{[1-(3,4-dichloro-benzenesulfonyl)-1,2,3,4-tetrahydro-quinoline-7-carbonyl]-amino}-benzoic acid methyl ester, which was hydrolyzed in step 5.

Example 42

2-Chloro-4-{[1-(3,5-dichloro-benzenesulfonyl)-1,2,3,4-tetrahydro-quinoline-7-carbonyl]-amino}-benzoic acid 2-Chloro-4-{[1-(3,5-dichloro-benzenesulfonyl)-1,2,3,4-tetrahydro-quinoline-7-carbonyl]-amino}-benzoic acid, m/z (ES+): 539.17 (M+H$^+$.), was prepared in analogy to example 40, steps 1 to 5. Step 4 was performed using 3,5-dichloro-benzenesulfonyl chloride, yielding 2-chloro-4-{[1-(3,5-dichloro-benzenesulfonyl)-1,2,3,4-tetrahydro-quinoline-7-carbonyl]-amino}-benzoic acid methyl ester, which was hydrolyzed in step 5.

Example 43

2-Chloro-4-{[1-(3-trifluoromethyl-benzenesulfonyl)-1,2,3,4-tetrahydro-quinoline-7-carbonyl]-amino}-benzoic acid 2-Chloro-4-{[1-(3-trifluoromethyl-benzenesulfonyl)-1,2,3,4-tetrahydro-quinoline-7-carbonyl]-amino}-benzoic acid, m/z (ES+): 539.24 (M+H$^+$.), was prepared in analogy to example 40, steps 1 to 5. Step 4 was performed using 3-trifluoromethyl-benzenesulfonyl chloride, yielding 2-chloro-4-{[1-(3-trifluoromethyl-benzenesulfonyl)-1,2,3,4-tetrahydro-

Example 44

2-Chloro-4-{[1-(4-difluoromethoxy-benzenesulfonyl)-1,2,3,4-tetrahydro-quinoline-7-carbonyl]-amino}-benzoic acid 2-Chloro-4-{[1-(4-difluoromethoxy-benzenesulfonyl)-1,2,3,4-tetrahydro-quinoline-7-carbonyl]-amino}-benzoic acid, m/z (ES+): 537.24 (M+H$^+$.), was prepared in analogy to example 40, steps 1 to 5. Step 4 was performed using 4-difluoromethoxy-benzenesulfonyl chloride, yielding 2-chloro-4-{[1-(4-difluoromethoxy-benzenesulfonyl)-1,2,3,4-tetrahydro-quinoline-7-carbonyl]-amino}-benzoic acid methyl ester, which was hydrolyzed in step 5.

Example 45

2-Chloro-4-{[1-(5-chloro-2-methoxy-benzenesulfonyl)-1,2,3,4-tetrahydro-quinoline-7-carbonyl]-amino}-benzoic acid 2-Chloro-4-{[1-(5-chloro-2-methoxy-benzenesulfonyl)-1,2,3,4-tetrahydro-quinoline-7-carbonyl]-amino}-benzoic acid, m/z (ES+): 535.25 (M+H$^+$.), was prepared in analogy to example 40, steps 1 to 5. Step 4 was performed using 5-chloro-2-methoxy-benzenesulfonyl chloride, yielding 2-chloro-4-{[1-(5-chloro-2-methoxy-benzenesulfonyl)-1,2,3,4-tetrahydro-quinoline-7-carbonyl]-amino}-benzoic acid methyl ester, which was hydrolyzed in step 5.

Example 46

2-Chloro-4-{[1-(2-methoxy-5-methyl-benzenesulfonyl)-1,2,3,4-tetrahydro-quinoline-7-carbonyl]-amino}-benzoic acid 2-Chloro-4-{[1-(2-methoxy-5-methyl-benzenesulfonyl)-1,2,3,4-tetrahydro-quinoline-7-carbonyl]-amino}-benzoic acid, m/z (ES+): 515.29 (M+H$^+$.), was prepared in analogy to example 40, steps 1 to 5. Step 4 was performed using 2-methoxy-5-methyl-benzenesulfonyl chloride, yielding 2-Chloro-4-{[1-(2-methoxy-5-methyl-benzenesulfonyl)-1,2,3,4-tetrahydro-quinoline-7-carbonyl]-amino}-benzoic acid methyl ester, which was hydrolyzed in step 5.

Example 47

2-Chloro-4-{[1-(3-chloro-benzenesulfonyl)-1,2,3,4-tetrahydro-quinoline-7-carbonyl]-amino}-benzoic acid 2-Chloro-4-{[1-(3-chloro-benzenesulfonyl)-1,2,3,4-tetrahydro-quinoline-7-carbonyl]-amino}-benzoic acid, m/z (ES+): 505.23 (M+H$^+$.), was prepared in analogy to example 40, steps 1 to 5. Step 4 was performed using 3-chloro-benzenesulfonyl chloride, yielding 2-chloro-4-{[1-(3-chloro-benzenesulfonyl)-1,2,3,4-tetrahydro-quinoline-7-carbonyl]-amino}-benzoic acid methyl ester, which was hydrolyzed in step 5.

Example 48

2-Fluoro-4-{[1-(3-fluoro-benzenesulfonyl)-1,2,3,4-tetrahydro-quinoline-7-carbonyl]-amino}-benzoic acid 2-Fluoro-4-{[1-(3-fluoro-benzenesulfonyl)-1,2,3,4-tetrahydro-quinoline-7-carbonyl]-amino}-benzoic acid, m/z (ES+): 473.24 (M+H$^+$.), was prepared in analogy to example 40, steps 1 to 5. Step 2 was performed using 4-amino-2-fluorobenzoic acid ethyl ester and yielded 2-fluoro-4-[(quinoline-7-carbonyl)-amino]-benzoic acid ethyl ester, which was reduced to 2-fluoro-4-[(1,2,3,4-tetrahydro-quinoline-7-carbonyl)-amino]-benzoic acid ethyl ester in step 3. Step 4 was performed using 3-fluoro-benzenesulfonyl chloride, yielding 2-fluoro-4-{[1-(3-fluoro-benzenesulfonyl)-1,2,3,4-tetrahydro-quinoline-7-carbonyl]-amino}-benzoic acid ethyl ester, which was hydrolyzed in step 5.

Example 49

4-{[1-(3-Chloro-benzenesulfonyl)-1,2,3,4-tetrahydro-quinoline-7-carbonyl]-amino}-2-fluoro-benzoic acid 4-{[1-(3-Chloro-benzenesulfonyl)-1,2,3,4-tetrahydro-quinoline-7-carbonyl]-amino}-2-fluoro-benzoic acid, m/z (ES+): 489.23 (M+H$^+$.), was prepared in analogy to example 48, steps 1 to 5. Step 4 was performed using 3-chloro-benzenesulfonyl chloride, yielding 4-{[1-(3-chloro-benzenesulfonyl)-1,2,3,4-tetrahydro-quinoline-7-carbonyl]-amino}-2-fluoro-benzoic acid ethyl ester, which was hydrolyzed in step 5.

Example 50

2-Fluoro-4-{[1-(2-methoxy-5-methyl-benzenesulfonyl)-1,2,3,4-tetrahydro-quinoline-7-carbonyl]-amino}-benzoic acid 2-Fluoro-4-{[1-(2-methoxy-5-methyl-benzenesulfonyl)-1,2,3,4-tetrahydro-quinoline-7-carbonyl]-amino}benzoic acid, m/z (ES+): 499.31 (M+H$^+$.), was prepared in analogy to example 48, steps 1 to 5. Step 4 was performed using 2-methoxy-5-methyl-benzenesulfonyl chloride, yielding 2-fluoro-4-{[1-(2-methoxy-5-methyl-benzenesulfonyl)-1,2,3,4-tetrahydro-quinoline-7-carbonyl]-amino}-benzoic acid ethyl ester, which was hydrolyzed in step 5.

Example 51

4-{[1-(5-Chloro-2-methoxy-benzenesulfonyl)-1,2,3,4-tetrahydro-quinoline-7-carbonyl]-amino}-2-fluoro-benzoic acid 4-{[1-(5-Chloro-2-methoxy-benzenesulfonyl)-1,2,3,4-tetrahydro-quinoline-7-carbonyl]-amino}-2-fluoro-benzoic acid, m/z (ES+): 519.26 (M+H$^+$.), was prepared in analogy to example 48, steps 1 to 5. Step 4 was performed using 5-chloro-2-methoxy-benzenesulfonyl chloride, yielding 4-{[1-(5-chloro-2-methoxy-benzenesulfonyl)-1,2,3,4-tetrahydro-quinoline-7-carbonyl]-amino}-2-fluoro-benzoic acid ethyl ester, which was hydrolyzed in step 5.

Example 52

4-{[1-(4-Difluoromethoxy-benzenesulfonyl)-1,2,3,4-tetrahydro-quinoline-7-carbonyl]-amino}-2-fluoro-benzoic acid 4-{[1-(4-Difluoromethoxy-benzenesulfonyl)-1,2,3,4-tetrahydro-quinoline-7-carbonyl]-amino}-2-fluoro-benzoic acid, m/z (ES+): 521.17 (M+H$^+$.), was prepared in analogy to example 48, steps 1 to 5. Step 4 was performed using 4-difluoromethoxy-benzenesulfonyl chloride, yielding 4-{[1-(4-difluoromethoxy-benzenesulfonyl)-1,2,3,4-tetrahydro-quinoline-7-carbonyl]-amino}-2-fluoro-benzoic acid ethyl ester, which was hydrolyzed in step 5.

Example 53

4-{[1-(3,5-Dichloro-benzenesulfonyl)-1,2,3,4-tetrahydro-quinoline-7-carbonyl]-amino}-2-fluorobenzoic acid 4-{[1-(3,5-Dichloro-benzenesulfonyl)-1,2,3,4-tetrahydro-quinoline-7-carbonyl]-amino}-2-fluoro-benzoic acid, m/z (ES+): 523.18 (M+H$^+$.), was prepared in analogy to example 48, steps 1 to 5. Step 4 was performed using 3,5-dichloro-benzenesulfonyl chloride, yielding 4-{[1-(3,5-dichloro-benzenesulfonyl)-1,2,3,4-tetrahydro-quinoline-7-carbonyl]-amino}-2-fluoro-benzoic acid ethyl ester, which was hydrolyzed in step 5.

Example 54

2-Fluoro-4-{[1-(3-trifluoromethyl-benzenesulfonyl)-1,2,3,4-tetrahydro-quinoline-7-carbonyl]-amino}-benzoic acid 2-Fluoro-4-{[1-(3-trifluoromethyl-benzenesulfonyl)-1,2,3,4-tetrahydro-quinoline-7-carbonyl]-amino}-benzoic acid, m/z (ES+): 523.29 (M+H$^+$.), was prepared in analogy to example 48, steps 1 to 5. Step 4 was performed using 3-trifluoromethyl-benzenesulfonyl chloride, yielding 2-fluoro-4-{[1-(3-trifluoromethyl-benzenesulfonyl)-1,2,3,4-tetrahydro-quinoline-7-carbonyl]-amino}-benzoic acid ethyl ester, which was hydrolyzed in step 5.

Example 55

4-{[1-(3,4-Dichloro-benzenesulfonyl)-1,2,3,4-tetrahydro-quinoline-7-carbonyl]-amino}-2-fluorobenzoic acid 4-{[1-(3,4-Dichloro-benzenesulfonyl)-1,2,3,4-tetrahydro-quinoline-7-carbonyl]-amino}-2-fluoro-benzoic acid, m/z (ES+): 523.22 (M+H$^+$.), was prepared in analogy to example 48, steps 1 to 5. Step 4 was performed using 3,4-dichloro-benzenesulfonyl chloride, yielding 4-{[1-(3,4-dichloro-benzenesulfonyl)-1,2,3,4-tetrahydro-quinoline-7-carbonyl]-amino}-2-fluoro-benzoic acid ethyl ester, which was hydrolyzed in step 5.

Example 56

1-(3-Chloro-benzenesulfonyl)-1,2,3,4-tetrahydroquinoline-7-carboxylic acid [4-(1H-tetrazol-5-yl)-3-trifluoromethyl-phenyl]-amide 1-(3-Chloro-benzenesulfonyl)-1,2,3,4-tetrahydro-quinoline-7-carboxylic acid [4-(1H-tetrazol-5-yl)-3-trifluoromethyl-phenyl]-amide, MS (ISP): m/e=561.1 (M−H) was prepared in analogy to example 40, steps 1 to 4, and example 13, step 4.

In analogy to example 40, quinoline-7-carboxylic acid was reacted with 4-amino-2-trifluoromethyl-benzonitrile in step 2, and the resulting quinoline-7-carboxylic acid (4-cyano-3-trifluoromethyl-phenyl)-amide was reduced to 1,2,3,4-tetrahydro-quinoline-7-carboxylic acid (4-cyano-3-trifluoromethyl-phenyl)-amide in step 3. This was coupled with 3-chloro-benzenesulfonyl chloride in step 4, yielding 1-(3-chloro-benzenesulfonyl)-1,2,3,4-tetrahydro-quinoline-7-carboxylic acid (4-cyano-3-trifluoromethyl-phenyl)-amide.

In analogy to example 13, step 4, 1-(3-chloro-benzenesulfonyl)-1,2,3,4-tetrahydro-quinoline-7-carboxylic acid (4-cyano-3-trifluoromethyl-phenyl)-amide was then converted to 1-(3-chloro-benzenesulfonyl)-1,2,3,4-tetrahydro-quinoline-7-carboxylic acid [4-(1H-tetrazol-5-yl)-3-trifluoromethyl-phenyl]-amide by reaction with ammonium chloride and sodium azide.

Example 57

4-{[1-(5-Chloro-2-methoxy-benzenesulfonyl)-1,2,3,4-tetrahydro-quinoline-7-carbonyl]-amino}-benzoic acid 4-{[1-(5-Chloro-2-methoxy-benzenesulfonyl)-1,2,3,4-tetrahydro-quinoline-7-carbonyl]-amino}-benzoic acid was prepared as illustrated in scheme 6.

Step 1:

To a solution of bis (pentamethyl-cyclopentadiene iridium dichloride) (32 mg, 0.02 equiv.) in a degassed mixture of isopropanol (9.5 ml) and water (0.5 ml) was added quinoline-7-carboxylic acid methyl ester (374 mg, 2.00 mmol) and perchloric acid (70% in water, 0.02 ml, 0.1 equiv.). The mixture was stirred at 85° C. for 17 hours, then the solvents were evaporated. The residue was purified by flash chromatography (heptane/ethyl acetate gradient), yielding 1,2,3,4-tetrahydro-quinoline-7-carboxylic acid methyl ester as a white solid, 305 mg (80%). MS (ISP): m/e=192.4 (M+H$^+$); $\delta_H$ (300 MHz; CDCl$_3$) 7.23 (1H, d), 7.13 (1H, s), 6.98 (1H, d), 3.86 (3H, s), 2.52 (2H, m), 3.32 (2H, t), 2.79 (2H, t), 1.94 (2H, m).

Step 2:

A solution of 1,2,3,4-tetrahydro-quinoline-7-carboxylic acid methyl ester (1.7 g, 9.3 mmol) in tetrahydrofuran (20 ml) was treated with diisopropylethyl amine (1.19 g, 9.3 mmol, 1 equiv.) and di-tertbutyl-dicarbonate (2.02 g, 9.3 mmol, 1 equiv.). The mixture was heated at reflux overnight, then the solvent was removed. 3,4-Dihydro-2H-quinoline-1,7-dicarboxylic acid 1-tert-butyl ester 7-methyl ester was used crude in the following reaction.

Step 3:

A solution of crude 3,4-dihydro-2H-quinoline-1,7-dicarboxylic acid 1-tert-butyl ester 7-methyl ester (2.7 g, 9.2 mmol) in methanol (30 ml) was treated with 3N NaOH (10 ml, 30 mmol, 3.3 equiv.) and stirred at room temperature for 5 h. The methanol was evaporated and the residual slurry was treated with 3N HCl (10 ml). The white precipitate was filtered, washing with water, and dried under high vacuum to afford 3,4-dihydro-2H-quinoline-1,7-dicarboxylic acid 1-tert-butyl ester as a white solid, 2.5 g (97%). MS (ISP): m/e=276.1 (M−H); $\delta_H$ (300 MHz; CDCl$_3$) 8.40 (0.25H, s), 8.33 (0.75H, s), 7.70 (0.25H, d), 7.64 (0.75H, d), 7.14 (1H, m), 3.75 (2H, m), 2.82 (2H, m), 1.94 (2H, m), 1.54 (9H, s).

Step 4:

A solution of 3,4-dihydro-2H-quinoline-1,7-dicarboxylic acid 1-tert-butyl ester (1.0 g, 3.61 mmol) in dimethylformamide (20 ml) was treated with diisopropyl ethyl amine (0.51 g, 3.97 mmol, 1.1 equiv.), O-(benzotriazol-1-yl)-N,N,N',N'-tetramethyluronium hexafluoro-phosphate (1.27 g, 3.97 mmol, 1.1 equiv.) and 4-amino-benzoic acid ethyl ester (0.65 g, 3.97 mmol, 1.1 equiv.). The mixture was stirred at room temperature overnight, then the solvent was evaporated and the residue purified by flash chromatography (heptane/ethyl acetate gradient) to afford 7-(4-ethoxycarbonyl-phenylcarbamoyl)-3,4-dihydro-2H-quinoline-1-carboxylic acid tert-butyl ester as a white solid, 1.1 g (70%). MS (ISP): m/e=423.1 (M−H).

A solution of 7-(4-ethoxycarbonyl-phenylcarbamoyl)-3,4-dihydro-2H-quinoline-1-carboxylic acid tert-butyl ester (1.1 g, 2.5 mmol) in trifluoroacetic acid (5 ml) was stirred at room temperature for 2 hours. The solvent was then removed and the residue redissolved in dichloromethane and washed with saturated sodium hydrogencarbonate. The organic layer was dried with $Na_2SO_4$ and evaporated. The residue was purified by flash chromatography (heptane/ethyl acetate gradient) to yield 4-[(1,2,3,4-tetrahydro-quinoline-7-carbonyl)-amino]-benzoic acid ethyl ester as a white solid, 790 mg (97%). MS (ISP): m/e=325.4 (M+H$^+$.); $\delta_H$ (300 MHz; CDCl$_3$) 8.59 (1H, s), 7.98 (2H, d), 7.77 (1H, s), 7.69 (2H, d), 7.48 (1H, d), 7.09 (1H, d), 4.37 (2H, q), 3.44 (2H, m), 2.79 (2H, t), 2.08 (2H, m), 1.40 (3H, t).

Step 5:

A solution of 4-[(1,2,3,4-tetrahydro-quinoline-7-carbonyl)-amino]-benzoic acid ethyl ester (140 mg, 0.43 mmol) in dichloromethane (5 ml) and pyridine (0.15 ml) was treated with 5-chloro-2-methoxy-benzenesulfonyl chloride (159 mg, 0.66 mmol, 1.5 equiv.) and stirred at room temperature for 17 hours. The solvent was then evaporated and the residue purified by flash chromatography (dichloromethane/ether 9:1) to yield 4-{[1-(5-chloro-2-methoxy-benzenesulfonyl)-1,2,3,4-tetrahydro-quinoline-7-carbonyl]-amino}-benzoic acid ethyl ester as a white foam, 227 mg (100%). MS (ISP): m/e=527.2 (M−H); $\delta_H$ (300 MHz; d6-DMSO) 10.5 (1H, s), 8.02 (1H, d), 7.96 (2H, d), 7.93 (2H, d), 7.85 (1H, d), 7.72 (1H, dd), 7.67 (1H, dd), 7.30 (1H, d), 7.23 (1H, d), 4.30 (2H, q), 3.78 (2H, m), 2.75 (2H, t), 1.74 (2H, m), 1.32 (3H, t).

Step 6:

4-{[1-(5-Chloro-2-methoxy-benzenesulfonyl)-1,2,3,4-tetrahydro-quinoline-7-carbonyl]-amino}-benzoic acid ethyl ester was hydrolyzed in analogy to what described before in example 40, step 5, yielding 4-{[1-(5-chloro-2-methoxy-benzenesulfonyl)-1,2,3,4-tetrahydro-quinoline-7-carbonyl]-amino}-benzoic acid, MS (ISP): m/e=499.0 (M−H).

Example 58

4-{[1-(3-Chloro-benzenesulfonyl)-1,2,3,4-tetrahydro-quinoline-7-carbonyl]-amino}-benzoic acid 4-{[1-(3-Chloro-benzenesulfonyl)-1,2,3,4-tetrahydro-quinoline-7-carbonyl]-amino}-benzoic acid, MS (ISP): m/e=469.0 (M−H), was prepared in analogy to example 57, steps 1 to 6. Step 5 was performed using 3-chloro-benzenesulfonyl chloride, yielding 4-{[1-(3-chloro-benzenesulfonyl)-1,2,3,4-tetrahydro-quinoline-7-carbonyl]-amino}-benzoic acid ethyl ester, which was hydrolyzed in step 6.

Example 59

4-{[1-(3-Trifluoromethyl-benzenesulfonyl)-1,2,3,4-tetrahydro-quinoline-7-carbonyl]-amino}-benzoic acid 4 4-{[1-(3-Trifluoromethyl-benzenesulfonyl)-1,2,3,4-tetrahydro-quinoline-7-carbonyl]-amino}-benzoic acid, MS (ISP): m/e=503.0 (M−H), was prepared in analogy to example 57, steps 1 to 6. Step 5 was performed using 3-trifluromethyl-benzenesulfonyl chloride, yielding 4-{[1-(3-trifluoromethyl-benzenesulfonyl)-1,2,3,4-tetrahydro-quinoline-7-carbonyl]-amino}-benzoic acid ethyl ester, which was hydrolyzed in step 6.

Example 60

4-{[1-(3-Fluoro-benzenesulfonyl)-1,2,3,4-tetrahydro-quinoline-7-carbonyl]-amino}-benzoic acid 4-{[1-(3-Fluoro-benzenesulfonyl)-1,2,3,4-tetrahydro-quinoline-7-carbonyl]-amino}-benzoic acid, MS (ISP): m/e=453.2 (M−H), was prepared in analogy to example 57, steps 1 to 6. Step 5 was performed using 3-fluoro-benzenesulfonyl chloride, yielding 4-{[1-(3-fluoro-benzenesulfonyl)-1,2,3,4-tetrahydro-quinoline-7-carbonyl]-amino}-benzoic acid ethyl ester, which was hydrolyzed in step 6.

Example 61

4-{[1-(5-Chloro-2-methoxy-benzenesulfonyl)-1H-indole-6-carbonyl]-amino}-benzoic acid 4-{[1-(5-Chloro-2-methoxy-benzenesulfonyl)-1H-indole-6-carbonyl]-amino}-benzoic acid was prepared as illustrated in scheme 16:

Scheme 16

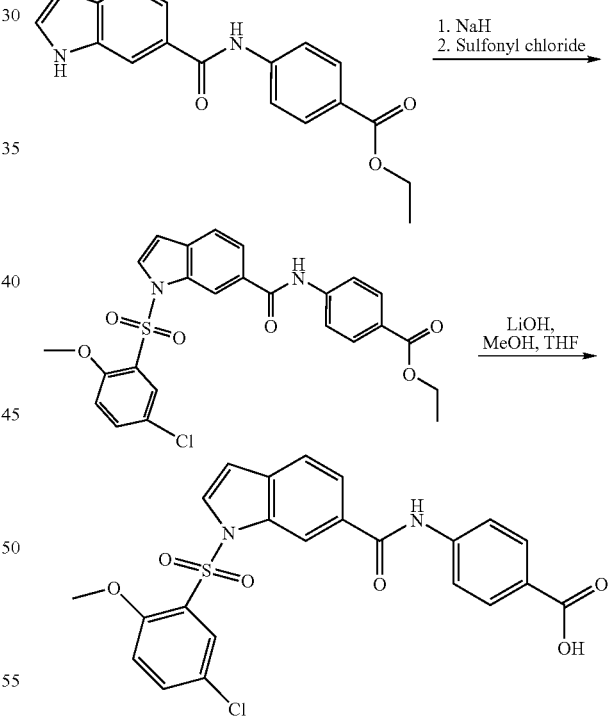

Step 1:

A solution of 4-[(1H-indole-6-carbonyl)-amino]-benzoic acid ethyl ester (100 mg, 0.32 mmol) in tetrahydrofuran (2 ml) was treated with NaH (55% dispersion in oil, 78 mg, 1 equiv.) and stirred at room temperature for 25'. The mixture was then treated with 5-chloro-2-methoxy-benzenesulfonyl chloride and stirred at room temperature for 4 hours. The reaction was quenched by adding 1N NH$_4$Cl. The aqueous phase was extracted with ethyl acetate and the combined organic layers dried with Na₂SO₄ and evaporated. The crude 4-{[1-(5-chloro-2-methoxy-benzenesulfonyl)-1H-indole-6-carbonyl]-amino}-benzoic acid ethyl ester, MS (ISP): m/e=511.3 (M−H), was used as such in the following reaction.

Step 2:
A solution of 4-{[1-(5-chloro-2-methoxy-benzenesulfonyl)-1H-indole-6-carbonyl]-amino}-benzoic acid ethyl ester (70 mg, 0.14 mmol) in tetrahydrofuran (1.5 ml) and methanol (0.5 ml) was treated with a 1N solution of LiOH in water (0.5 ml). The mixture was stirred at room temperature for 4 hours, then acidified with 1N HCl (0.5 ml). Methanol and tetrahydrofuran were evaporated and the residual slurry was extracted three times with ethyl acetate. The combined organic phases were dried with Na₂SO₄ and evaporated, and the residue purified by flash chromatography (dichloromethane/methanol gradient), to yield 4-{[1-(5-chloro-2-methoxy-benzenesulfonyl)-1H-indole-6-carbonyl]-amino}-benzoic acid as a light yellow solid, 17 mg (25%). MS (ISP): m/e=483.0 (M−H); δ$_H$ (300 MHz; d6-DMSO) 12.77 (1H, bs), 10.60 (1H, s), 8.34 (1H, s), 8.08 (1H, d), 7.91-7.97 (6H, m), 7.75-7.80 (2H, m), 7.23 (1H, d), 6.91 (1H, d), 3.70 (3H, s).

Example 62

4-{[1-(5-Chloro-2-methoxy-benzenesulfonyl)-4-methyl-2,3-dihydro-1H-indole-6-carbonyl]-amino}-benzoic acid The title compound was prepared as illustrated in scheme 4.

Step 1:
4-Methyl-ah-indole-6-carboxylic acid methyl ester was reduced to 4-methyl-2,3-dihydro-1H-indole-6-carboxylic acid methyl ester in analogy to example 34, step 1. Yellow solid, MS (ISP): m/e 192.1 (M+H).

Step 2:
4-Methyl-2,3-dihydro-1H-indole-6-carboxylic acid methyl ester was reacted with 5-chloro-2-methoxybenzenesulfonyl chloride in analogy to example 34, step 2, yielding 1-(5-chloro-2-methoxy-benzenesulfonyl)-4-methyl-2,3-dihydro-1H-indole-6-carboxylic acid methyl ester. Pink solid, MS (ISP): m/e 396.1 (M+H).

Step 3:
1-(5-Chloro-2-methoxy-benzenesulfonyl)-4-methyl-2,3-dihydro-1H-indole-6-carboxylic acid methyl ester was hydrolyzed in analogy to example 34, step 3, yielding 1-(5-chloro-2-methoxy-benzenesulfonyl)-4-methyl-2,3-dihydro-1H-indole-6-carboxylic acid. Light yellow solid, MS (ISP): m/e 382.2 (M+H).

Step 4:
A solution of 1-(5-chloro-2-methoxy-benzenesulfonyl)-4-methyl-2,3-dihydro-1H-indole-6-carboxylic acid (150 mg, 0.393 mmol), ethyl 4-aminobenzoate (130 mg, 0.786 mmol), 4-methylmorpholine (199 mg, 1.96 mmol), and O-(7-azabenzotriazol-1-yl)-N,N,N',N'-tetramethyluronium hexafluorophosphate (224 mg, 0.589 mmol) in N,N-dimethylformamide (1.5 mL) was stirred at room temperature for 15 min, then 4-(dimethylamino)pyridine (49 mg, 0.39 mmol) was added, and the solution was stirred at 60° C. for 18 h. After cooling, the reaction mixture was partitioned between water, heptane, and ethyl acetate. The organic layer was washed with brine, dried (MgSO₄), and evaporated. Chromatography (SiO₂, heptane-ethyl acetate gradient) produced 4-{[1-(5-chloro-2-methoxy-benzenesulfonyl)-4-methyl-2,3-dihydro-1H-indole-6-carbonyl]-amino}-benzoic acid ethyl ester (190 mg, 91%). White solid, MS (ISP): m/e 529.2 (M+H).

Step 5:
A suspension of 4-{[1-(5-chloro-2-methoxy-benzenesulfonyl)-4-methyl-2,3-dihydro-1H-indole-6-carbonyl]-amino}-benzoic acid ethyl ester (185 mg, 0.350 mmol) in ethanol (2 mL) and 3 M aq. potassium hydroxide solution (0.35 mL, 1.05 mmol) was heated at 50° C. for 18 h, then volatile material was removed by distillation. The residue was taken up in water (2 mL) and brought to pH 1 by addition of 2 M aq. hydrochloric acid solution. The precipitate was collected by filtration and dried, producing 4-{[1-(5-chloro-2-methoxy-benzenesulfonyl)-4-methyl-2,3-dihydro-1H-indole-6-carbonyl]-amino}-benzoic acid (139 mg, 76%). Off-white solid, MS (ISP): m/e 499.1 (M−H).

Preparation of 4-methyl-1H-indole-6-carboxylic acid methyl ester:
A solution of 4,5-dimethyl-3-nitrobenzoic acid (*Helv. Chim. Acta* 1980, 37, 385; 2.50 g, 12.8 mmol) and N,N-dimethylformamide dimethyl acetal (3.66 g, 30.7 mmol) in N,N-dimethylformamide (25 mL) was heated at 140° C. for 4 h, then volatile material was removed by distillation. The residue was taken up in tetrahydrofuran (10 mL) and methanol (10 mL), then Raney nickel (aqueous suspension, 1 mL) and hydrazine hydrate (1.85 g, 57.6 mmol) were added over 30 min in three portions at 50° C., and the reaction was kept at 50° C. for another 90 min. The reaction mixture was filtered through diatomaceous earth, the filtrate was dried (MgSO₄), and evaporated. Chromatography (SiO₂, heptane-ethyl acetate 2:1) produced 4-methyl-1H-indole-6-carboxylic acid methyl ester (1.68 g, 69%). White solid, MS (ISP): m/e 190.3 (M+H).

Example 63

4-{[1-(5-Chloro-2-methoxy-benzenesulfonyl)-4-methyl-2,3-dihydro-1H-indole-6-carbonyl]-amino}-2-fluoro-benzoic acid The title compound, MS (ISP): m/e 517.2 (M−H), was produced as described in example 62, steps 1-5. Step 4 was performed using ethyl 4-amino-2-fluorobenzoate and yielded 4-{[1-(5-chloro-2-methoxy-benzenesulfonyl)-4-methyl-2,3-dihydro-1H-indole-6-carbonyl]-amino}-2-fluoro-benzoic acid ethyl ester, which was hydrolyzed in step 5.

Example 64

2-Chloro-4-{[1-(5-chloro-2-methoxy-benzenesulfonyl)-4-methyl-2,3-dihydro-1H-indole-6-carbonyl]-amino}-benzoic acid The title compound, MS (ISP): m/e 533.0 (M−H), was produced as described in example 62, steps 1-5. Step 4 was performed using ethyl 4-amino-2-chlorobenzoate and yielded 2-chloro-4-{[1-(5-chloro-2-methoxy-benzenesulfonyl)-4-methyl-2,3-dihydro-1H-indole-6-carbonyl]-amino}-benzoic acid ethyl ester, which was hydrolyzed in step 5.

Example 65

4-{[1-(5-Chloro-2-methoxy-benzenesulfonyl)-2,3,4,5-tetrahydro-1H-benzo[b]azepine-8-carbonyl]-amino}-benzoic acid Step 1:
Borane tetrahydrofuran complex (1 M solution in tetrahydrofuran, 21 mL, 21 mmol) was added to a solution of 8-bromo-1,3,4,5-tetrahydro-benzo[b]azepin-2-one (prepared from 7-bromo-3,4-dihydro-2H-naphthalen-1-one in analogy with the general procedure described in *J Chem. Soc.*

(C) 1969, 183; 1.00 g, 4.17 mmol) in tetrahydrofuran, and the solution was heated at reflux for 2 h. After cooling, methanol (21 mL) was added, and volatile material was removed by distillation. The residue was taken up in 5% ethanolic sulfuric acid solution (12 mL) and heated at reflux for 2 h, then basified to pH 10 by addition of 2 M aq. sodium hydroxide solution and partitioned between water and ethyl acetate. The organic layer was dried (MgSO$_4$) and evaporated. Chromatography (SiO$_2$, heptane-ethyl acetate 2:1) yielded 8-bromo-2,3,4,5-tetrahydro-1H-benzo[b]azepine (865 mg, 92%). White solid, MS (ISP) m/e 226.1 (M+H).

Step 2:
8-Bromo-2,3,4,5-tetrahydro-1H-benzo[b]azepine was reacted with 5-chloro-2-methoxybenzenesulfonyl chloride in analogy to example 34, step 2, yielding 8-bromo-1-(5-chloro-2-methoxy-benzenesulfonyl)-2,3,4,5-tetrahydro-1H-benzo[b]azepine. Off-white solid, MS (ISP): m/e 430.2 (M+H).

Step 3
A solution of 8-bromo-1-(5-chloro-2-methoxy-benzenesulfonyl)-2,3,4,5-tetrahydro-1H-benzo[b]azepine (1.20 g, 2.78 mmol), triethylamine (703 mg, 6.96 mmol), and dichloro [1,1'-bis(diphenylphosphine)ferrocene]palladium(II) dichloromethane complex (120 mg, 0.278 mmol) in toluene (6 mL) and methanol (6 mL) was heated at 110° C. under a carbon monoxide atmosphere (100 bar) for 18 h, then the reaction mixture was concentrated. Chromatography of the residue (SiO$_2$, heptane-ethyl acetate 2:1) yielded 1-(5-chloro-2-methoxy-benzenesulfonyl)-2,3,4,5-tetrahydro-1H-benzo[b]azepine-8-carboxylic acid methyl ester (709 mg, 62%). White solid, MS (ISP): m/e 410.1 (M+H).

Step 4:
1-(5-Chloro-2-methoxy-benzenesulfonyl)-2,3,4,5-tetrahydro-1H-benzo[b]azepine-8-carboxylic acid methyl ester was hydrolyzed in analogy to example 34, step 3, yielding 1-(5-chloro-2-methoxy-benzenesulfonyl)-2,3,4,5-tetrahydro-1H-benzo[b]azepine-8-carboxylic acid. Light yellow solid, MS (ISP): m/e 394.1 (M–H).

Step 5:
1-(5-Chloro-2-methoxy-benzenesulfonyl)-2,3,4,5-tetrahydro-1H-benzo[b]azepine-8-carboxylic acid was reacted with ethyl 4-aminobenzoate in analogy to example 62, step 4, yielding 4-{[1-(5-chloro-2-methoxy-benzenesulfonyl)-2,3,4,5-tetrahydro-1H-benzo[b]azepine-8-carbonyl]-amino}-benzoic acid ethyl ester. Light brown solid, MS (ISP) 543.2 (M+H).

Step 6:
Hydrolysis of 4-{[1-(5-chloro-2-methoxy-benzenesulfonyl)-2,3,4,5-tetrahydro-1H-benzo[b]azepine-8-carbonyl]-amino}-benzoic acid ethyl ester in analogy to example 62, step 5 produced 4-{[1-(5-chloro-2-methoxy-benzenesulfonyl)-2,3,4,5-tetrahydro-1H-benzo[b]azepine-8-carbonyl]-amino}-benzoic acid. White solid, MS (ISP): m/e 515.3 (M+H).

Example 66

4-{[1-(5-Chloro-2-methoxy-benzenesulfonyl)-2,3,4,5-tetrahydro-1H-benzo[b]azepine-8-carbonyl]-amino}-2-fluoro-benzoic acid The title compound, MS (ISP): m/e 531.1 (M–H), was produced as described in example 65, steps 1-6. Step 5 was performed using ethyl 4-amino-2-fluorobenzoate and yielded 4-{[1-(5-chloro-2-methoxy-benzenesulfonyl)-2,3,4,5-tetrahydro-1H-benzo[b]azepine-8-carbonyl]-amino}-2-fluoro-benzoic acid ethyl ester, which was hydrolyzed in step 6.

Example 67

2-Chloro-4-{[1-(5-chloro-2-methoxy-benzenesulfonyl)-2,3,4,5-tetrahydro-1H-benzo[b]azepine-8-carbonyl]-amino}-benzoic acid The title compound, MS (ISP): m/e 547.1 (M–H), was produced as described in example 65, steps 1-6. Step 5 was performed using ethyl 4-amino-2-chlorobenzoate and yielded 2-chloro-4-{[1-(5-chloro-2-methoxy-benzenesulfonyl)-2,3,4,5-tetrahydro-1H-benzo[b]azepine-8-carbonyl]-amino}-benzoic acid ethyl ester, which was hydrolyzed in step 6.

Example 68

4-{[1-(5-Chloro-2-methoxy-benzenesulfonyl)-3-methyl-2,3-dihydro-1H-indole-6-carbonyl]-amino}-benzoic acid The title compound was prepared as illustrated in scheme 4.

Step 1:
3-Methyl-1H-indole-6-carboxylic acid methyl ester (*Bioorg. Med. Chem. Lett.* 1998, 8, 1867) was reduced to 3-methyl-2,3-dihydro-1H-indole-6-carboxylic acid methyl ester in analogy to example 34, step 1, which was used directly in the next step.

Step 2:
3-Methyl-2,3-dihydro-1H-indole-6-carboxylic acid methyl ester was reacted with 5-chloro-2-methoxybenzenesulfonyl chloride in analogy to example 34, step 2, yielding 1-(5-chloro-2-methoxy-benzenesulfonyl)-3-methyl-2,3-dihydro-1H-indole-6-carboxylic acid methyl ester. Off-white solid, MS (ISP): m/e 395.9 (M+H).

Step 3:
1-(5-Chloro-2-methoxy-benzenesulfonyl)-3-methyl-2,3-dihydro-1H-indole-6-carboxylic acid methyl ester was hydrolyzed in analogy to example 34, step 3, yielding 1-(5-chloro-2-methoxy-benzenesulfonyl)-3-methyl-2,3-dihydro-1H-indole-6-carboxylic acid. Light yellow solid, MS (ISP): m/e 379.9 (M–H).

Step 4:
1-(5-Chloro-2-methoxy-benzenesulfonyl)-3-methyl-2,3-dihydro-1H-indole-6-carboxylic acid was reacted with ethyl 4-aminobenzoate in analogy to example 62, step 4, yielding 4-{[1-(5-chloro-2-methoxy-benzenesulfonyl)-3-methyl-2,3-dihydro-1H-indole-6-carbonyl]-amino}-benzoic acid ethyl ester. White foam, MS (ISP) 529.1 (M+H).

Step 5:
Hydrolysis of 4-{[1-(5-chloro-2-methoxy-benzenesulfonyl)-3-methyl-2,3-dihydro-1H-indole-6-carbonyl]-amino}-benzoic acid ethyl ester in analogy to example 62, step 5 produced 4-{[1-(5-chloro-2-methoxy-benzenesulfonyl)-3-methyl-2,3-dihydro-1H-indole-6-carbonyl]-amino}-benzoic acid. White solid, MS (ISP): m/e 499.1 (M–H).

Example 69

4-{[1-(5-Chloro-2-methoxy-benzenesulfonyl)-3-methyl-2,3-dihydro-1H-indole-6-carbonyl]-amino}-2-fluoro-benzoic acid The title compound, MS (ISP): m/e 517.2 (M–H), was produced as described in example 68, steps 1-5. Step 4 was performed using ethyl 4-amino-2-fluorobenzoate and yielded 4-{[1-(5-chloro-2-methoxy-benzenesulfonyl)-3-methyl-2,3- dihydro-1H-indole-6-carbonyl]-amino}-2-fluoro-benzoic acid ethyl ester, which was hydrolyzed in step 5.

Example 70

2-Chloro-4-{[1-(5-chloro-2-methoxy-benzenesulfonyl)-3-methyl-2,3-dihydro-1H-indole-6-carbonyl]-amino}-benzoic acid The title compound, MS (ISP): m/e 533.0 (M–H), was produced as described in example 68, steps 1-5. Step 4 was performed using ethyl 4-amino-2-chlorobenzoate and yielded 2-chloro-4-{[1-(5-chloro-2-methoxy-benzenesulfonyl)-3-methyl-2,3-dihydro-1H-indole-6-carbonyl]-amino}-benzoic acid ethyl ester, which was hydrolyzed in step 5.

Example 71

4-{[1-(2-Methoxy-5-methyl-benzenesulfonyl)-1H-indole-6-carbonyl]-amino}-benzoic acid Step 1:

A solution of 1H-indole-6-carboxylic acid (1.00 g, 6.20 mmol), tert-butyl 4-aminobenzoate (1.20 g, 6.20 mmol), 4-methylmorpholine (3.14 g, 31.0 mmol), and O-(7-azabenzotriazol-1-yl)-N,N,N',N'-tetramethyluronium hexafluorophosphate (3.53 g, 9.31 mmol) in N,N-dimethylformamide (10 mL) was stirred at room temperature for 15 min, then 4-(dimethylamino)pyridine (758 mg, 6.20 mmol) was added, and the solution was stirred at 60° C. for 3 days. After cooling, the reaction mixture was partitioned between water, heptane, and ethyl acetate. The organic layer was washed with brine, dried (MgSO$_4$), and evaporated. Chromatography (SiO$_2$, heptane-ethyl acetate gradient) followed by trituration in dichloromethane yielded 4-[(1H-indole-6-carbonyl)-amino]-benzoic acid tert-butyl ester (629 mg, 30%). White solid, MS (ISP): m/e 337.2 (M+H).

Step 2:

A suspension of 4-[(1H-indole-6-carbonyl)-amino]-benzoic acid tert-butyl ester (200 mg, 0.595 mmol) and tetrabutylammonium hydrogensulfate (20 mg, 0.059 mmol) was treated with 50% aq. sodium hydroxide solution (0.30 mL, 7.4 mmol), then after 5 min 2-methoxy-5-methylbenzenesulfonyl chloride (0.197 mg, 0.892 mmol) was added, and the two-phase mixture was stirred for 1 h at room temperature. The reaction mixture was partitioned between water and ethyl acetate, the organic layer was washed with brine, dried (MgSO$_4$), and evaporated. Chromatography (SiO$_2$, heptane-ethyl acetate gradient) produced 4-{[1-(2-methoxy-5-methyl-benzenesulfonyl)-1H-indole-6-carbonyl]-amino}-benzoic acid tert-butyl ester (309 mg, 100%). Off-white solid, MS (ISP): m/e 521.3 (M+H).

Step 3:

A suspension of 4-{[1-(2-methoxy-5-methyl-benzenesulfonyl)-1H-indole-6-carbonyl]-amino}-benzoic acid tert-butyl ester (305 mg, 0.585 mmol) in hydrogen chloride solution (4 M in 1,4-dioxane, 5 mL) was stirred at room temperature for 16 h, then the precipitate was collected by filtration and washed with ethyl acetate, to afford 4-{[1-(2-methoxy-5-methyl-benzenesulfonyl)-1H-indole-6-carbonyl]-amino}-benzoic acid (211 mg, 78%). Pink solid, MS (ISP): m/e 463.1 (M–H).

Example 72

4-{[1-(3-Chloro-benzenesulfonyl)-1H-indole-6-carbonyl]-amino}-benzoic acid

The title compound, MS (ISP): m/e 453.1 (M–H), was produced as described in example 71, steps 1-3. Step 2 was performed using 3-chlorobenzenesulfonyl chloride and yielded 4-{[1-(3-chloro-benzenesulfonyl)-1H-indole-6-carbonyl]-amino}-benzoic acid tert-butyl ester, which was hydrolyzed in step 3.

Example 73

4-{[1-(3,5-Dimethyl-benzenesulfonyl)-1H-indole-6-carbonyl]-amino}-benzoic acid

The title compound, MS (ISP): m/e 447.1 (M–H), was produced as described in example 71, steps 1-3. Step 2 was performed using 3,5-dimethylbenzenesulfonyl chloride and yielded 4-{[1-(3,5-dimethyl-benzenesulfonyl)-1H-indole-6-carbonyl]-amino}-benzoic acid tert-butyl ester, which was hydrolyzed in step 3.

Example 74

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example 75

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 76

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example 77

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 78

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

What is claimed is:
1. A compound of formula (I):

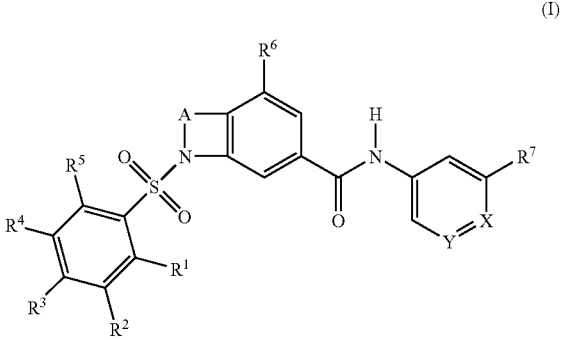

wherein
X is N or $CR^8$;
Y is N or $CR^9$;
A is —$C(R^{10}R^{11})C(R^{12}R^{13})$—, —$C(R^{10}R^{11})C(R^{12}R^{13})C(R^{14}R^{15})$—, —$C(R^{10}R^{11})C(R^{12}R^{13})C(R^{14}R^{15})C(R^{16}R^{17})$—, —$C(R^{10}R^{11})C(R^{12}R^{13})C(R^{14}R^{15})C(R^{16}R^{17})C(R^{18}R^{19})$— or —$C(R^{10})$=$C(R^{11})$—;
$R^1$, $R^2$, $R^3$, $R^4$ and $R^5$ independently from each other are hydrogen, halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-$S(O)_2$, $NH_2$—$S(O)_2$, N(H, lower-alkyl)-$S(O)_2$ or N(lower-alkyl)$_2$-$S(O)_2$, $NH_2$—C(O), N(H, lower-alkyl)-C(O), N(lower-alkyl)$_2$-C(O) or lower-alkoxy-C(O), wherein lower-alkyl is optionally substituted with hydroxy, lower-alkoxy, $NH_2$, N(H, lower-alkyl) or N(lower-alkyl)$_2$;
$R^6$ is hydrogen, halogen, lower-alkyl, lower-alkoxy, fluoro-lower-alkyl, fluoro-lower-alkoxy, hydroxy or hydroxy-lower-alkyl;
$R^7$ is hydrogen, halogen, hydroxy, cyano, lower-alkyl, lower-alkoxy, fluoro-lower-alkyl, fluoro-lower-alkoxy or hydroxy-lower-alkyl;
$R^8$ is hydrogen, halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-$S(O)_2$, $NH_2$—$S(O)_2$, N(H, lower-alkyl)-$S(O)_2$, N(lower-alkyl)$_2$-$S(O)_2$, $NH_2$—C(O), N(H, lower-alkyl)-C(O), N(lower-alkyl)$_2$-C(O), lower-alkoxy-C(O), COOH, 1H-tetrazolyl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, $SO_3H$, 3-hydroxy-isooxazolyl, 3-hydroxy-pyran-4-one-yl or $P(O)(OCH_2CH_3)$OH, wherein lower-alkyl is optionally substituted with hydroxy, $NH_2$, N(H, lower-alkyl) or N(lower-alkyl)$_2$, and wherein fluoro-lower-alkyl is optionally substituted with hydroxy;
$R^9$ is hydrogen, halogen, hydroxy, cyano, lower-alkyl, lower-alkoxy, fluoro-lower-alkyl, fluoro-lower-alkoxy or hydroxy-lower-alkyl;
$R^{10}$, $R^{11}$, $R^{12}$, $R^{13}$, $R^{14}$, $R^{15}$, $R^{16}$, $R^{17}$, $R^{18}$, $R^{19}$ independently from each other are hydrogen, halogen, hydroxy, lower-alkyl, lower-alkoxy, fluoro-lower-alkyl, fluoro-lower-alkoxy, hydroxy-lower-alkyl or cyano;
and pharmaceutically acceptable salts and esters thereof.

2. The compound according to claim 1, wherein $R^8$ is hydrogen, halogen, cyano, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H, lower-alkyl)-S(O)$_2$, N(lower-alkyl)$_2$-S(O)$_2$, NH$_2$—C(O), N(H, lower-alkyl)-C(O), N(lower-alkyl)$_2$-C(O), lower-alkoxy-C(O), COOH, 1H-tetrazol-2-yl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, SO$_3$H, 3-hydroxy-isooxazol, 3-hydroxy-pyran-4-one or P(O)(OCH$_2$CH$_3$)OH, wherein lower-alkyl is optionally substituted with hydroxy, NH$_2$, N(H, lower-alkyl) or N(lower-alkyl)$_2$, and wherein fluoro-lower-alkyl is optionally substituted with hydroxy.

3. The compound according to claim 1, wherein $R^1$, $R^2$, $R^3$, $R^4$ and $R^5$ independently from each other are hydrogen, halogen, lower-alkyl, fluoro-lower-alkyl, lower-alkoxy or fluoro-lower-alkoxy.

4. The compound according to claim 1, wherein $R^1$, $R^2$, $R^3$, $R^4$ and $R^5$ independently from each other are hydrogen, halogen, lower-alkyl, fluoro-lower-alkyl or lower-alkoxy.

5. The compound according to claim 1, wherein $R^5$ is hydrogen or lower-alkoxy.

6. The compound according to claim 1, wherein $R^2$ is hydrogen, halogen, lower-alkyl or fluoro-lower-alkyl.

7. The compound according to claim 1, wherein $R^3$ is hydrogen or halogen.

8. The compound according to claim 1, wherein $R^4$ is hydrogen, halogen, lower-alkyl or fluoro-lower-alkyl.

9. The compound according to claim 1, wherein $R^5$ is hydrogen or lower-alkoxy.

10. The compound according to claim 1, wherein $R^6$ is hydrogen, lower-alkyl or lower-alkoxy.

11. The compound according to claim 1, wherein $R^6$ is hydrogen or lower-alkoxy.

12. The compound according to claim 1, wherein $R^6$ is hydrogen.

13. The compound according to claim 1, wherein $R^7$ is hydrogen, halogen or fluoro-lower-alkyl.

14. The compound according to claim 1, wherein $R^7$ is hydrogen or halogen.

15. The compound according to claim 1, wherein X is $CR^8$ and $R^8$ is as defined in claim 1.

16. The compound according to claim 15, wherein $R^8$ is hydrogen, halogen, COOH, 1H-tetrazolyl, 4H-[1,2,4]oxadiazol-3-yl-5-one or fluoro-lower-alkyl which is substituted with hydroxy.

17. The compound according to claim 16, wherein $R^8$ is COOH or 4H-[1,2,4]oxadiazol-3-yl-5-one.

18. The compound according to claim 1, wherein Y is $CR^9$ and $R^9$ is as defined in claim 1.

19. The compound according to claim 18, wherein $R^9$ is hydrogen, halogen or fluoro-lower-alkyl.

20. The compound according to claim 19, wherein $R^9$ is hydrogen or halogen.

21. The compound according to claim 1, wherein A is —C(R$^{10}$R$^{11}$)C(R$^{12}$R$^{13}$)—, —C(R$^{10}$R$^{11}$)C(R$^{12}$R$^{13}$)C(R$^{14}$R$^{15}$)—, —C(R$^{10}$R$^{11}$)C(R$^{12}$R$^{13}$)C(R$^{14}$R$^{15}$)C(R$^{16}$R$^{17}$)— or —C(R$^{10}$)=C(R$^{11}$)—, and R$^{10}$, R$^{11}$, R$^{12}$, R$^{13}$, R$^{14}$, R$^{15}$, R$^{16}$, and R$^{17}$, are as defined in claim 1.

22. The compound according to claim 21, wherein R$^{10}$, R$^{11}$, R$^{12}$, R$^{13}$, R$^{14}$, R$^{15}$, R$^{16}$, and R$^{17}$, independently from each other are hydrogen or lower-alkyl.

23. The compound according to claim 1, wherein A is —C(R$^{10}$R$^{11}$)C(R$^{12}$R$^{13}$)—, —C(R$^{10}$R$^{11}$)C(R$^{12}$R$^{13}$)C(R$^{14}$R$^{15}$)— or —C(R$^{10}$)=C(R$^{11}$)—, and R$^{10}$, R$^{11}$, R$^{12}$, R$^{13}$, R$^{14}$ and R$^{15}$ are as defined in claim 1.

24. The compound according to claim 23, wherein R$^{10}$, R$^{11}$, R$^{12}$, R$^{13}$, R$^{14}$ and R$^{15}$ are hydrogen.

25. The compound according to claim 1, selected from the group consisting of

2-Chloro-4-{[1-(3-chloro-benzenesulfonyl)-2,3-dihydro-1H-indole-6-carbonyl]-amino}-benzoic acid;

2-Chloro-4-{[1-(5-chloro-2-methoxy-benzenesulfonyl)-2,3-dihydro-1H-indole-6-carbonyl]-amino}-benzoic acid;

2-Chloro-4-{[1-(3-trifluoromethyl-benzenesulfonyl)-2,3-dihydro-1H-indole-6-carbonyl]-amino}-benzoic acid;

2-Chloro-4-{[1-(3,4-dichloro-benzenesulfonyl)-2,3-dihydro-1H-indole-6-carbonyl]-amino}-benzoic acid;

2-Chloro-4-{[1-(3,5-dichloro-benzenesulfonyl)-2,3-dihydro-1H-indole-6-carbonyl]-amino}-benzoic acid;

2-Chloro-4-{[1-(3-fluoro-benzenesulfonyl)-2,3-dihydro-1H-indole-6-carbonyl]-amino}-benzoic acid;

2-Chloro-4-{[1-(2-methoxy-5-methyl-benzenesulfonyl)-2,3-dihydro-1H-indole-6-carbonyl]-amino}-benzoic acid;

2-Chloro-4-{[1-(4-difluoromethoxy-benzenesulfonyl)-2,3-dihydro-1H-indole-6-carbonyl]-amino}-benzoic acid;

4-{[1-(3-Chloro-benzenesulfonyl)-2,3-dihydro-1H-indole-6-carbonyl]-amino}-2-fluoro-benzoic acid;

2-Fluoro-4-{[1-(3-trifluoromethyl-benzenesulfonyl)-2,3-dihydro-1H-indole-6-carbonyl]-amino}-benzoic acid;

4-{[1-(3,4-Dichloro-benzenesulfonyl)-2,3-dihydro-1H-indole-6-carbonyl]-amino}-2-fluoro-benzoic acid;

4-{[1-(5-Chloro-2-methoxy-benzenesulfonyl)-2,3-dihydro-1H-indole-6-carbonyl]-amino}-2-fluoro-benzoic acid;

1-(3-Chloro-benzenesulfonyl)-2,3-dihydro-1H-indole-6-carboxylic acid [4-(1H-tetrazol-5-yl)-3-trifluoromethyl-phenyl]-amide;

2-Fluoro-4-{[4-methoxy-1-(3-trifluoromethyl-benzenesulfonyl)-2,3-dihydro-1H-indole-6-carbonyl]-amino}-benzoic acid;

4-{[1-(3-Chloro-benzenesulfonyl)-4-methoxy-2,3-dihydro-1H-indole-6-carbonyl]-amino}-2-fluoro-benzoic acid;

4-{[1-(3,4-Dichloro-benzenesulfonyl)-4-methoxy-2,3-dihydro-1H-indole-6-carbonyl]-amino}-2-fluoro-benzoic acid;

4-{[1-(5-Chloro-2-methoxy-benzenesulfonyl)-4-methoxy-2,3-dihydro-1H-indole-6-carbonyl]-amino}-2-fluoro-benzoic acid;

4-{[1-(3,5-Dichloro-benzenesulfonyl)-4-methoxy-2,3-dihydro-1H-indole-6-carbonyl]-amino}-2-fluoro-benzoic acid;

2-Fluoro-4-{[1-(3-fluoro-benzenesulfonyl)-4-methoxy-2,3-dihydro-1H-indole-6-carbonyl]-amino}-benzoic acid;

2-Fluoro-4-{[4-methoxy-1-(2-methoxy-5-methyl-benzenesulfonyl)-2,3-dihydro-1H-indole-6-carbonyl]-amino}-benzoic acid;

2-Chloro-4-{[4-methoxy-1-(3-trifluoromethyl-benzenesulfonyl)-2,3-dihydro-1H-indole-6-carbonyl]-amino}-benzoic acid;

2-Chloro-4-{[1-(5-chloro-2-methoxy-benzenesulfonyl)-4-methoxy-2,3-dihydro-1H-indole-6-carbonyl]-amino}-benzoic acid;

2-Chloro-4-{[1-(3,5-dichloro-benzenesulfonyl)-4-methoxy-2,3-dihydro-1H-indole-6-carbonyl]-amino}-benzoic acid;

2-Chloro-4-{[1-(3-fluoro-benzenesulfonyl)-4-methoxy-2,3-dihydro-1H-indole-6-carbonyl]-amino}-benzoic acid;
2-Chloro-4-{[1-(3-chloro-benzenesulfonyl)-4-methoxy-2,3-dihydro-1H-indole-6-carbonyl]-amino}-benzoic acid;
4-{[1-(3-Chloro-benzenesulfonyl)-4-methoxy-2,3-dihydro-1H-indole-6-carbonyl]-amino}-benzoic acid;
4-{[1-(5-Chloro-2-methoxy-benzenesulfonyl)-4-methoxy-2,3-dihydro-1H-indole-6-carbonyl]-amino}-benzoic acid;
4-{[4-Methoxy-1-(2-methoxy-5-methyl-benzenesulfonyl)-2,3-dihydro-1H-indole-6-carbonyl]-amino}-benzoic acid;
4-{[1-(3-Fluoro-benzenesulfonyl)-4-methoxy-2,3-dihydro-1H-indole-6-carbonyl]-amino}-benzoic acid;
4-{[1-(3,5-Dichloro-benzenesulfonyl)-2,3-dihydro-1H-indole-6-carbonyl]-amino}-benzoic acid;
4-{[1-(5-Chloro-2-methoxy-benzenesulfonyl)-2,3-dihydro-1H-indole-6-carbonyl]-amino}-benzoic acid;
4-{[1-(3-Trifluoromethoxy-benzenesulfonyl)-2,3-dihydro-1H-indole-6-carbonyl]-amino}-benzoic acid;
4-{[1-(3-Fluoro-benzenesulfonyl)-2,3-dihydro-1H-indole-6-carbonyl]-amino}-benzoic acid;
1-(5-Chloro-2-methoxy-benzenesulfonyl)-2,3-dihydro-1H-indole-6-carboxylic acid (4-chloro-phenyl)-amide;
1-(5-Chloro-2-methoxy-benzenesulfonyl)-2,3-dihydro-1H-indole-6-carboxylic acid phenylamide;
4-[(1-Benzenesulfonyl-2,3-dihydro-1H-indole-6-carbonyl)-amino]-benzoic acid;
1-(5-Chloro-2-methoxy-benzenesulfonyl)-2,3-dihydro-1H-indole-6-carboxylic acid [4-(1H-tetrazol-5-yl)-phenyl]-amide;
1-(5-Chloro-2-methoxy-benzenesulfonyl)-2,3-dihydro-1H-indole-6-carboxylic acid [4-(5-oxo-4,5-dihydro-[1,2,4]oxadiazol-3-yl)-phenyl]-amide;
1-(5-Chloro-2-methoxy-benzenesulfonyl)-2,3-dihydro-1H-indole-6-carboxylic acid [4-(2,2,2-trifluoro-1-hydroxy-ethyl)-phenyl]-amide;
2-Chloro-4-{[1-(3-fluoro-benzenesulfonyl)-1,2,3,4-tetrahydro-quinoline-7-carbonyl]-amino}-benzoic acid;
2-Chloro-4-{[1-(3,4-dichloro-benzenesulfonyl)-1,2,3,4-tetrahydro-quinoline-7-carbonyl]-amino}-benzoic acid;
2-Chloro-4-{[1-(3,5-dichloro-benzenesulfonyl)-1,2,3,4-tetrahydro-quinoline-7-carbonyl]-amino}-benzoic acid;
2-Chloro-4-{[1-(3-trifluoromethyl-benzenesulfonyl)-1,2,3,4-tetrahydro-quinoline-7-carbonyl]-amino}-benzoic acid;
2-Chloro-4-{[1-(4-difluoromethoxy-benzenesulfonyl)-1,2,3,4-tetrahydro-quinoline-7-carbonyl]-amino}-benzoic acid;
2-Chloro-4-{[1-(5-chloro-2-methoxy-benzenesulfonyl)-1,2,3,4-tetrahydro-quinoline-7-carbonyl]-amino}-benzoic acid;
2-Chloro-4-{[1-(2-methoxy-5-methyl-benzenesulfonyl)-1,2,3,4-tetrahydro-quinoline-7-carbonyl]-amino}-benzoic acid;
2-Chloro-4-{[1-(3-chloro-benzenesulfonyl)-1,2,3,4-tetrahydro-quinoline-7-carbonyl]-amino}-benzoic acid;
2-Fluoro-4-{[1-(3-fluoro-benzenesulfonyl)-1,2,3,4-tetrahydro-quinoline-7-carbonyl]-amino}-benzoic acid;
4-{[1-(3-Chloro-benzenesulfonyl)-1,2,3,4-tetrahydro-quinoline-7-carbonyl]-amino}-2-fluoro-benzoic acid;
2-Fluoro-4-{[1-(2-methoxy-5-methyl-benzenesulfonyl)-1,2,3,4-tetrahydro-quinoline-7-carbonyl]-amino}-benzoic acid;
4-{[1-(5-Chloro-2-methoxy-benzenesulfonyl)-1,2,3,4-tetrahydro-quinoline-7-carbonyl]-amino}-2-fluoro-benzoic acid;
4-{[1-(4-Difluoromethoxy-benzenesulfonyl)-1,2,3,4-tetrahydro-quinoline-7-carbonyl]-amino}-2-fluoro-benzoic acid;
4-{[1-(3,5-Dichloro-benzenesulfonyl)-1,2,3,4-tetrahydro-quinoline-7-carbonyl]-amino}-2-fluoro-benzoic acid;
2-Fluoro-4-{[1-(3-trifluoromethyl-benzenesulfonyl)-1,2,3,4-tetrahydro-quinoline-7-carbonyl]-amino}-benzoic acid;
4-{[1-(3,4-Dichloro-benzenesulfonyl)-1,2,3,4-tetrahydro-quinoline-7-carbonyl]-amino}-2-fluoro-benzoic acid;
1-(3-Chloro-benzenesulfonyl)-1,2,3,4-tetrahydro-quinoline-7-carboxylic acid [4-(1H-tetrazol-5-yl)-3-trifluoromethyl-phenyl]-amide;
4-{[1-(5-Chloro-2-methoxy-benzenesulfonyl)-1,2,3,4-tetrahydro-quinoline-7-carbonyl]-amino}-benzoic acid;
4-{[1-(3-Chloro-benzenesulfonyl)-1,2,3,4-tetrahydro-quinoline-7-carbonyl]-amino}-benzoic acid;
4-{[1-(3-Trifluoromethyl-benzenesulfonyl)-1,2,3,4-tetrahydro-quinoline-7-carbonyl]-amino}-benzoic acid;
4-{[1-(3-Fluoro-benzenesulfonyl)-1,2,3,4-tetrahydro-quinoline-7-carbonyl]-amino}-benzoic acid; and
4-{[1-(5-Chloro-2-methoxy-benzenesulfonyl)-1H-indole-6-carbonyl]-amino}-benzoic acid;
and pharmaceutically acceptable salts and esters thereof.

26. The compound according to claim 1, selected from the group consisting of
2-Chloro-4-{[1-(3,4-dichloro-benzenesulfonyl)-2,3-dihydro-1H-indole-6-carbonyl]-amino}-benzoic acid;
2-Chloro-4-{[1-(3,5-dichloro-benzenesulfonyl)-2,3-dihydro-1H-indole-6-carbonyl]-amino}-benzoic acid;
2-Fluoro-4-{[1-(3-trifluoromethyl-benzenesulfonyl)-2,3-dihydro-1H-indole-6-carbonyl]-amino}-benzoic acid;
4-{[1-(5-Chloro-2-methoxy-benzenesulfonyl)-2,3-dihydro-1H-indole-6-carbonyl]-amino}-benzoic acid;
1-(5-Chloro-2-methoxy-benzenesulfonyl)-2,3-dihydro-1H-indole-6-carboxylic acid [4-(1H-tetrazol-5-yl)-phenyl]-amide;
2-Chloro-4-{[1-(5-chloro-2-methoxy-benzenesulfonyl)-1,2,3,4-tetrahydro-quinoline-7-carbonyl]-amino}-benzoic acid;
2-Fluoro-4-{[1-(2-methoxy-5-methyl-benzenesulfonyl)-1,2,3,4-tetrahydro-quinoline-7-carbonyl]-amino}-benzoic acid;
4-{[1-(5-Chloro-2-methoxy-benzenesulfonyl)-1,2,3,4-tetrahydro-quinoline-7-carbonyl]-amino}-2-fluoro-benzoic acid;
4-{[1-(3,5-Dichloro-benzenesulfonyl)-1,2,3,4-tetrahydro-quinoline-7-carbonyl]-amino}-2-fluoro-benzoic acid;
4-{[1-(5-Chloro-2-methoxy-benzenesulfonyl)-1,2,3,4-tetrahydro-quinoline-7-carbonyl]-amino}-benzoic acid; and
4-{[1-(5-Chloro-2-methoxy-benzenesulfonyl)-1H-indole-6-carbonyl]-amino}-benzoic acid;
and pharmaceutically acceptable salts and esters thereof.

27. The compound according to claim 1, selected from the group consisting of
- 4-{[1-(5-Chloro-2-methoxy-benzenesulfonyl)-4-methyl-2,3-dihydro-1H-indole-6-carbonyl]-amino}-benzoic acid;
- 4-{[1-(5-Chloro-2-methoxy-benzenesulfonyl)-4-methyl-2,3-dihydro-1H-indole-6-carbonyl]-amino}-2-fluoro-benzoic acid;
- 2-Chloro-4-{[1-(5-chloro-2-methoxy-benzenesulfonyl)-4-methyl-2,3-dihydro-1H-indole-6-carbonyl]-amino}benzoic acid;
- 4-{[1-(5-Chloro-2-methoxy-benzenesulfonyl)-2,3,4,5-tetrahydro-1H-benzo[b]azepine-8-carbonyl]-amino}-benzoic acid;
- 4-{[1-(5-Chloro-2-methoxy-benzenesulfonyl)-2,3,4,5-tetrahydro-1H-benzo[b]azepine-8-carbonyl]-amino}-2-fluoro-benzoic acid;
- 2-Chloro-4-{[1-(5-chloro-2-methoxy-benzenesulfonyl)-2,3,4,5-tetrahydro-1H-benzo[b]azepine-8-carbonyl]-amino}-benzoic acid;
- 4-{[1-(5-Chloro-2-methoxy-benzenesulfonyl)-3-methyl-2,3-dihydro-1H-indole-6-carbonyl]-amino}-benzoic acid;
- 4-{[1-(5-Chloro-2-methoxy-benzenesulfonyl)-3-methyl-2,3-dihydro-1H-indole-6-carbonyl]-amino}-2-fluoro-benzoic acid;
- 2-Chloro-4-{[1-(5-chloro-2-methoxy-benzenesulfonyl)-3-methyl-2,3-dihydro-1H-indole-6-carbonyl]-amino}-benzoic acid;
- 4-{[1-(2-Methoxy-5-methyl-benzenesulfonyl)-1H-indole-6-carbonyl]-amino}-benzoic acid;
- 4-{[1-(3-Chloro-benzenesulfonyl)-1H-indole-6-carbonyl]-amino}-benzoic acid; and
- 4-{[1-(3,5-Dimethyl-benzenesulfonyl)-1H-indole-6-carbonyl]-amino}-benzoic acid;

and pharmaceutically acceptable salts and esters thereof.

28. A process for the manufacture of compounds of formula (I) according to claim 1, comprising the step of:
a) reacting a compound of formula (IV)

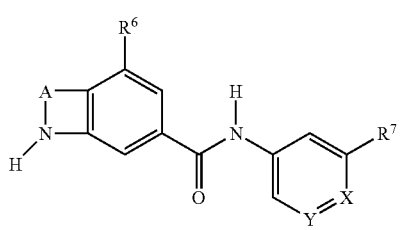

(IV)

with a compound of formula (V)

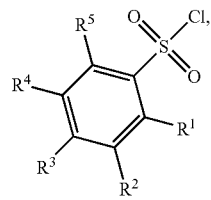

(V)

or
b) reacting a compound of formula (VI)

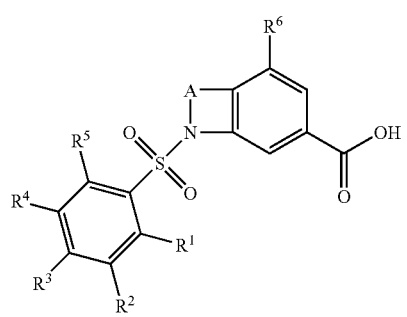

(VI)

with a compound of formula (VII)

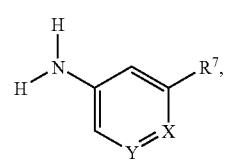

(VII)

wherein $R^1$, $R^2$, $R^3$, $R^4$, $R^5$, $R^6$, $R^7$, A, X and Y are as defined in any of claims 1-27.

29. A pharmaceutical composition, comprising a therapeutically effective amount of a compound according to claim 1 and a pharmaceutically acceptable carrier and/or adjuvant.

* * * * *

UNITED STATES PATENT AND TRADEMARK OFFICE
CERTIFICATE OF CORRECTION

| | | |
|---|---|---|
| PATENT NO. | : 7,713,996 B2 | Page 1 of 1 |
| APPLICATION NO. | : 11/519485 | |
| DATED | : May 11, 2010 | |
| INVENTOR(S) | : Jean Ackermann et al. | |

It is certified that error appears in the above-identified patent and that said Letters Patent is hereby corrected as shown below:

In Column 65, Claim 5, Line 22 delete:
    "The compound according to claim 1, wherein $R^5$ is hydrogen or lower-alkoxy."

And insert:
    --The compound according to claim 1, wherein $R^1$ is hydrogen or lower-alkoxy.--

Signed and Sealed this

Twenty-ninth Day of June, 2010

David J. Kappos
*Director of the United States Patent and Trademark Office*